(12) United States Patent
Kim et al.

(10) Patent No.: US 9,034,603 B2
(45) Date of Patent: May 19, 2015

(54) DRIED COMPOSITION FOR HOT-START PCR WITH LONG-TERM STABILITY

(75) Inventors: Seong-Youl Kim, Daejeon (KR); Hyun Bae Kim, Daejeon (KR); Hae-Joon Park, Seongnam-si (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 238 days.

(21) Appl. No.: 12/682,456

(22) PCT Filed: Oct. 28, 2008

(86) PCT No.: PCT/KR2008/006355
§ 371 (c)(1),
(2), (4) Date: Apr. 9, 2010

(87) PCT Pub. No.: WO2009/057931
PCT Pub. Date: May 7, 2009

(65) Prior Publication Data
US 2010/0209973 A1 Aug. 19, 2010

(30) Foreign Application Priority Data

Oct. 29, 2007 (KR) .................. 10-2007-0109055

(51) Int. Cl.
*C12Q 1/68* (2006.01)
(52) U.S. Cl.
CPC ..................... *C12Q 1/686* (2013.01)
(58) Field of Classification Search
None
See application file for complete search history.

(56) References Cited

U.S. PATENT DOCUMENTS

| 5,614,387 | A * | 3/1997 | Shen et al. ............... 435/91.2 |
| 5,700,590 | A * | 12/1997 | Masor et al. ............... 426/656 |
| 6,951,744 | B2 * | 10/2005 | Clark et al. ............... 435/91.2 |
| 2003/0049655 | A1 * | 3/2003 | Clark et al. ............... 435/6 |
| 2006/0057617 | A1 | 3/2006 | Clark et al. |
| 2008/0050737 | A1 * | 2/2008 | Arieli et al. ............... 435/6 |

FOREIGN PATENT DOCUMENTS

KR 1020000055626 A 9/2000

OTHER PUBLICATIONS

Fratamico et al. (2005) Canada J of Microbiol vol. 51:515-522.*
M. Kramer et al.: "Enzymatic Amplification of DNA by PCR: Standard Procedures and Optimization," Current Protocols in Molecular Biology, vol. S56, Unit 15, 14 pages, 2001.
Bassam and Caetano-Anolles, "Automated 'Hot Start' PCR using mineral oil and paraffin wax," BioTechniques 14(1):3 pages, 1993.
Horton et al., "AmpliGrease: 'Hot Start' PCR using petroleum jelly," BioTechniques 16:42-43, 1994.
Kaijalainen et al., "An alternative hot start technique for PCR in small volumes using beads of wax-embedded reaction components dried in trehalose," Nucleic Acids Research 21(12):2959-2960, 1993.
Pomp and Medrano, "Organic solvents as facilitators of polymerase chain reaction," BioTechniques 10(1):58-59, 1991.
Sharkey et al., "Antibodies as thermolabile switches: high temperature triggering for the polymerase chain reaction," BioTechnology 12:506-509, 1994.
Wainwright and Seifert, "Paraffin beads can replace mineral oil as an evaporation barrier in PCR," BioTechniques 14(1):35-36, 1993.

* cited by examiner

*Primary Examiner* — Suchira Pande
(74) *Attorney, Agent, or Firm* — Rothwell, Figg, Ernst & Manbeck, P.C.

(57) ABSTRACT

The present invention relates to a dried composition for hot-start PCR, more precisely a dried composition for hot-start PCR with improved stability and long-term storagability which is characteristically prepared by the steps of preparing a reaction mixture by mixing an aqueous solution containing reaction buffer, $MgCl_2$, 4 types of dNTPs, DNA polymerase with pyrophosphate and pyrophosphatase in a reaction tube; and drying the reaction mixture prepared above, a preparation method of the same and a method for amplifying nucleic acid using the same. The dried composition for hot-start PCR is added with pyrophosphate and pyrophosphatase together before drying, so that it can have improved stability and long-term storagability as well as convenience in use, compared with the conventional compositions for hot-start PCR. Therefore, this composition can be effectively used for hot-start PCR, multiplex PCR or real-time quantitative PCR.

16 Claims, 59 Drawing Sheets

Slope:-3.645270
Intercept:45.113503
R2:0.993671

SEQUENCE LISTING

```
<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagaatccgc ataccaggaa                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagcagcatt ttggaataac c                                                  21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 3
gccccagctg ctcaccatcg cta                                               23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcttcctac agtactcccc tgc                                               23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggccactgac aaccaccctt aacc                                              24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgctctgc cgcttcacgc                                                   20

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccggataaa aacgtcgatg acatttgc                                          28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatgacgcat cctcacgata atatccgc                                          28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
ccatgattca gtgtgcccgt ctgg                                          24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgaacgtcgc gcagagaaac agg                                           23

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcacagaagc tattatgcgt ccccagg                                       27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcttcctcgt gcatcgagct attcgg                                        26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttgttcctt tgccgcgaga atgg                                          24

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcctttgcct cgctatacat ttctaaatcg ccttg                              35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
gatgatcaac tggctttcca aactcgtatt cgtca         35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgctgaacac accagtgtaa gggatgttta tgacg         35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agcaattcag atctctcacc taccaaacaa tgccc         35

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggctgattga ccggcagatt a         21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcgggtatag gttttattga tggc         24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gattgctctt aggtctggcc cctc         24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
gtcctgcttg cttacctcgc ttagt                                      25
```

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gtgttatctc ctaggttggc tctg                                       24
```

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
caagtggctc ctgacctgga gtc                                        23
```

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
acctgatttc cttactgcct ctggc                                      25
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
tggatgtggt gttcccaat                                             19
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gttcaggcaa ccgttttga                                             19
```

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

```
ctcataccga gttgcatcca acg                                        23
```

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccaatcactc accaacctct tgt                                               23

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agcaggatga agaggaatat gataaa                                            26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tcctggctat cgctggatgt gtctgc                                            26

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggaggaac agagagacgt taatg                                             25

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tccctcttgt gagcccaatg                                                   20

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tgaggaacca cacgccacga agc                                               23

```
<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaactgatga gcgatccgaa tag                                               23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccaccactga ttagcgaatg c                                                 21
```

DRIED COMPOSITION FOR HOT-START PCR WITH LONG-TERM STABILITY

CROSS REFERENCE TO RELATED APPLICATIONS

This application is a 35 U.S.C. §371 National Phase Entry Application from PCT/KR2008/006355, filed Oct. 28, 2008, and designating the United States, which claims priority under 35 U.S.C. §119 to Korean Patent Application No. 10-2007-0109055 filed Oct. 29, 2007, which is incorporated herein in its entirety.

FIELD OF THE INVENTION

The present invention relates to a dried composition for hot-start PCR with long-term stability and a use of the same, more precisely, a dried composition for hot-start PCR which is stabilized and has a long-term storagability (shelf-life) by adding a required amount of polyols, inorganic pyrophosphate (referred as "PPi" hereinafter), and pyrophosphatase (referred as "PPase" hereinafter) to the conventional PCR composition.

DESCRIPTION OF THE RELATED ART

Specificity of PCR is determined by high stringency of a primer binding to a target gene sequence. All the ingredients necessary for gene amplification are mixed at room temperature before predenaturation. Thus, during this mixing, low stringency priming occurs. The polymerase retains its enzyme activity at a low temperature, so when priming occurs, a PCR product might be generated. Therefore, this low stringency priming is another critical cause of non-specific amplification along with complexity of target DNA sequence and low reaction temperature. Non-specific amplification consumes primers and other ingredients limited in concentrations while PCR cycles repeat, suggesting that a non-specific reaction itself acts like a competitive inhibitor. Non-specific amplification causes a serious problem particularly in detection of a target DNA with a low copy number, in amplification of a DNA sample at a low concentration, and in multiplex PCR using different primers at a time.

In an effort to overcome the said problem of PCR, "hot-start PCR" has been developed. Hot-start PCR is a kind of PCR to obtain a more pure PCR product, which allows high temperature mixing of each reactant, so that PCR specificity can be increased by preventing low stringency priming frequently occurring at room temperature and oligomerization of a non-specific primer.

The simplest way to perform hot-start PCR is to open the hot reaction tube and add necessary ingredients therein. However, this method might expose the reaction mixture to contamination, form aerosol, and cause evaporation. Another way to perform hot-start PCR is to generate a physical barrier between necessary ingredients, for example between a primer and a template. As an electro-physical barrier, paraffin wax has been generally used. Precisely, a reaction mixture is covered with paraffin wax, and when the wax is hardened, reagents (starting reagents) are loaded thereon, to which mineral oil is added. Then, the temperature of PCR machine is raised to 70° C.-90° C. Then, the wax is dissolved and the reaction mixture and starting reagents are mixed, leading to PCR. As explained, dissolution of the wax and mixing of the ingredients occur precisely at high temperatures. So, according to this method, high stringency priming is facilitated, simultaneous amplification of different DNA samples is also facilitated, and long-term storagability of the reaction mixture is secured due to the wax and oil layer. However, the said method is troublesome and takes a long time (Bassan, B. J. and Caentno-Anolles, G., Biotechniques, 14:30-34, 1993). In addition, mineral oil used as an evaporation barrier can contaminate PCR samples, which are presented as non-DNA-containing bands, making quantitative PCR data analysis difficult. Therefore, to improve this method, it has been proposed to use paraffin beads alone for hot-start PCR. Paraffin beads form a solid layer up to 55° C. So, a primer does not mix well with a template DNA at room temperature and only when the reaction temperature is higher than the melting point of paraffin, a primer is mixed with a template DNA, suggesting that it might increase PCR specificity. Paraffin exists at the bottom of the micro-centrifuge tube, so sample collection is easy and costs little. Therefore, paraffin beads are expected to be a promising candidate for improving hot-start PCR (Wainwright, L. A. and Seifert, H. S., Biotechniques, 14:34-36, 1993).

Another hot-start PCR method is characterized by using petroleum jelly such as AmpliGrease instead of paraffin wax. This method is similar to the above method using wax and oil. Precisely, a reaction mixture is separated into two layers, a bottom mix and top mix. Petroleum jelly is added between the two mixes to prevent the two mixes from being mixed at room temperature. Petroleum jelly begins to melt at a lower temperature (approximate melting point: 50° C.) than the melting point of wax and is not hardened again by cooling, which is the difference from the conventional method using wax (Horton, R. M., Hoppe, B. L. and Conti-Tronconi, Biotechniques, 16:42-43, 1994). However, this method has disadvantages when the amount of sample is large. That is, when a sample is used in excess, the bottom mix and top mix do not mix well because of the difference in density between the two mixes. So, this method is only effective in the reaction with a small volume of sample.

Other methods are used such as using reaction beads prepared by coating a reaction mixture dried over trehalose solution with wax (Kaijalainen, S. et al., Nucleic Acids Res., 212959-2960, 1993) or adding different organic solvents such as PEG, DMSO, Glycerol, etc, used as PCR accelerators, to a reaction mixture to increase hot-start PCR efficiency (Pomp, D. et al., Biotechniques, 10:58-59, 1991).

As explained hereinbefore, studies and attempts have been made for successful hot-start PCR and the necessity of hot-start PCR has been well recognized. Nevertheless, hot-start PCR is still limited in use and cannot be applied to diverse fields of experiments, taking into consideration economical aspects and limited skills. Unfortunately, the result of hot-start PCR using paraffin beads has not been as successful as the result of the conventional PCR. The recent hot-start PCR is only useful with Taq DNA polymerase (Enneth, G., Christy, J., Atwood, S. M., and Daiss, J. L. 1994, Biotechnology, 12; 506-509). That is, to perform hot-start PCR with other polymerases, each thermostable polymerase specific antibody has to be separately constructed, having a long preparation time and high costs.

To overcome the said problem, hot-start PCR using PPi and thermostable PPase has been developed (Korean Patent No. 10-0292883 and U.S. Pat. No. 6,951,744). Particularly, this method is characterized when a polymerase reaction at room temperature is suppressed by adding PPi strongly binding to magnesium ions essential for DNA polymerization and then PPase is reacted at high temperature to eliminate PPi, from which a reaction is started. This method is applicable regardless of types of polymerase and has an advantage of maintaining a constant reaction temperature by continuous elimination of PPi generated from dNTP during a polymerase reaction. But, once hot-start PCR master mix is prepared by this method, pyrophosphatase starts decomposing PPi slowly from $Mg^{2+}$ even at a low temperature, so that DNA is activated, resulting in the decrease of hot-start PCR effect. Furthermore, PPase is very unstable. So, once it is added to PCR master mix, it loses its activity at room temperature or at 4° C. So, this kind of PCR master mix cannot be stored at room temperature or at 4° C. and must be stored at −20° C. To avoid the said problem, PPase must be separately stored in a different container and when it is added to a reaction, it must be separately added with PPi, causing inconvenience, compared with the conventional PCR master mix generally used, and problems in reproducibility.

SUMMARY OF THE INVENTION

It is an object of the present invention, to overcome the said problems, to provide a dried composition for hot-start PCR having improved reproducibility, stability and long-term storagability and accordingly having improved applicability in diverse gene diagnosis and tests, and a method for producing the same.

DETAILED DESCRIPTION OF THE PREFERRED EMBODIMENTS

The present inventors completed this invention by confirming that the dried composition for hot start-PCR prepared by adding PPi and PPase to PCR reaction mixture comprising reaction buffer, $MgCl_2$, 4 types of dNTPs and DNA polymerase and drying thereof has more advantages of eliminating a non-specific product, increased reproducibility and stability, simple storage and long-term storagability and convenience in use, compared with the conventional composition for PCR.

The dried composition for hot-start PCR of the present invention is prepared by drying the reaction mixture comprising reaction buffer, $MgCl_2$, 4 types of dNTPs, DNA polymerase, PPi and PPase in a reaction tube. The reaction mixture may further comprise primers, probes, nucleic acid templates, and fluorescent dyes.

Any PPase in the market can be used as the PPase of the present invention without limitation, which is preferably exemplified by Tte-inorganic pyrophosphatase (SibEnzyme Ltd.) originated from *E. coli* in which *Thermus thermophilus* B35 originated inorganic pyrophosphatase gene is cloned and Pto-inorganic pyrophosphatase (Bioneer corporation, republic of Korea) originated from *E. coli* in which *Picrophilus torridus* originated inorganic pyrophosphatase gene is cloned. 1 unit of Pto-inorganic pyrophosphatase is defined as the amount of the enzyme necessary for producing 40 nmole of phosphate from pyrophosphate for 1 minute. The reaction is performed by using Tris-HCl (pH 7.5), 5 mM $MgCl_2$, and 2.0 mM PPi with the total reaction volume of 0.5 Ml at 70° C. for 10 minutes.

The fluorescent dye herein is selected from the group consisting of SyBr Green, EtBr and HRdye.

The reaction buffer herein is preferably 10 mM Tris-HCl, 40 mM KCl, pH 9. The content of PPi in the PCR composition is preferably 0.3-5.0 mM, more preferably 0.95-3.0 mM, and most preferably 2.0 mM. If the content of PPi is higher than 5.0 mM, the concentration of PPase needs to increase proportionately. Then, yield of the PCR product will decrease. If the content of PPi is lower than 0.3 mM, $Mg^{2+}$ arresting activity of the PCR composition will be reduced, resulting in the unsatisfactory inhibition effect on the non-specific reaction product produced by non-specific priming. The content of PPase in the PCR composition is preferably more than 30 to 200 mU per 20 μl of PCR mixture, more preferably 50-100 mU and most preferably about 80 mU. If the content of PPase is higher than 200 mM per 20 μl of PCR mixture, the confirmation of the result is only possible at over concentration when high copy number DNA is used as a template, compared with when low copy number DNA is used as a template, and reactivity is also reduced, resulting in the decrease of the PCR product. If the content of PPase is lower than 30 mU per 20 μl of PCR mixture, the non-specific PCR product is produced (see FIG. 3). The 4 types of dNTPs herein are dATP, dTTP, dGTP and dCTP. Any DNA polymerase known to those skilled in the art can be used in this invention without limitation and particularly the polymerase having the activity of 5'→3' exonuclease, the polymerase having the activity of 3'→5' exonuclease, and the polymerase having none of the activities of 5'→3' exonuclease and 3'→5' exonuclease can be used independently or together. The polymerase having the activity of 5'→3' exonuclease is exemplified by Taq DNA polymerase. The polymerase having the activity of 3'→5' exonuclease is exemplified by Pfu DNA polymerase or TLA DNA polymerase (Bioneer corporation, republic of Korea). The polymerase having none of the activities of 5'→3' exonuclease and 3'→5' exonuclease is exemplified by Top DNA polymerase (Bioneer corporation, republic of Korea). The content of DNA polymerase in the PCR composition is 0.1-10 U (unit), preferably 0.5-2 U, and more preferably 1 U. Taq, Pfu, Top and TLA DNA polymerases have the characteristics as shown in Table 1.

TABLE 1

|  | Taq. DNA polymerase | Pfu DNA polymerase | Top DNA polymerase | TLA DNA polymerase |
| --- | --- | --- | --- | --- |
| 5'->3' exonuclease activity | YES | NO | NO | NO |
| 3'->5' exonuclease activity | NO | YES | NO | YES |
| Terminal transferase activity | YES | NO | YES | NO |
| Error rate ($\times 10^{-6}$) | 4.91 | 1.90 | Not confirmed | Not confirmed |
| Fragment size | ≤10 kbp | ≤5 kbp | ≤10 kbp | ≤15 kbp |
| Optimum activity temperature (° C.) | 72 | 72 | 72 | 72 |
| Half life (min, at 95° C.) | 80 | Not confirmed | Not confirmed | Not confirmed |
| $MgCl_2$ (mM) | 1.5 | — | 1.5 | 1.0 |
| $MgSO_4$ (mM) | — | 2.0 | — | — |

TABLE 1-continued

|  | Taq. DNA polymerase | Pfu DNA polymerase | Top DNA polymerase | TLA DNA polymerase |
|---|---|---|---|---|
| KCl (mM) | 40 | 10 | 30 | 70 |
| Optimum pH (at 25° C.) | 9.0 | 8.8 | 9.0 | 9.0 |

The stabilized dried composition for PCR of the present invention may further comprise a dye and/or polyols which are not reactive to nucleic acid for the convenience in experiments, for the prevention of contamination by PCR product, for the stabilization of DNA polymerase and dNTPs and for the improvement of reactivity.

Herein, the "non-reactive dye" is selected among those dyes which do not affect PCR reaction, which is exemplified by soluble dye such as rhodamine, tamra, lax, bromophenol blue, xylene cyanole, bromocresol red, and cresol red, among which xylene cyanole is more preferred. The preferable content of such non-reactive dye in the whole composition is 0.0001-0.01 weight % and more preferably 0.001-0.005 weight % and most preferably 0.001-0.003 weight %. If the content of the non-reactive dye is less than 0.0001 weight %, which means the content of the dye is too low to analyze PCR product by electrophoresis on agarose gel. That is, it is very difficult to observe the sample movement by the naked eye. If the content of the non-reactive dye is higher than 0.01 weight %, such a high content of a soluble dye will act as a reaction inhibitor during PCR. In addition, such a high concentration interrupts the sample movement during electrophoresis after sedimentation to agarose gel.

Polyols can be used as an additional stabilizer for the stabilization of the dried composition of the present invention, which can be one or more compounds selected from the group consisting of glucose, glycerol, mannitol, galacsitol, glucitol, and sorbitol. The content of the polyol is preferably 10-500 mM and more preferably 50-300 mM. If the content is higher than 500 mM, it is hardly prepared as a water-soluble solution because of the solubility of a soluble polymer itself. Besides, under such a high concentration, mixing is not satisfactory because of high viscosity, the volume of the dried product is bigger than necessary, and dissolution in sterilized distilled water and gene solution for PCR is difficult. In addition, a soluble polymer at high concentration can act as a reaction inhibitor. On the contrary, if the content is less than 10 mM, the target enzyme and surface water molecules could not be coated fully and thereby could not be protected properly. Therefore, under such a low concentration, the stabilization effect of enzyme is not expected, drying is not properly performed because viscosity of the solution is too low so that the solution spreads at the whole bottom of the tube, and the enzyme is not fully protected. In this invention, in addition to the polyols, gelatin, bovine serum albumin, Thesit or PEG-8000 can be used as a stabilizer.

Drying can be performed by one of the conventional methods such as drying at room temperature, drying at elevated temperature (40-60° C.), freeze drying and vacuum drying. Any drying process can be used without limitation as long as no component of the composition is damaged. Drying method can be determined according to the kind and the amount of an enzyme. In this invention, freeze drying or vacuum drying using vacuum centrifugation can be used.

The composition of the present invention can be used without limitation not only for the conventional PCR but also for any nucleic acid amplification methods such as multiplex PCR, real-time PCR, and real-time quantitative PCR.

PPase used in this invention is a thermo-stable enzyme which is stable even at high temperature of at least 70° C. So, it is stable during the whole processes of PCR. PPase is activated at the temperature where Taq DNA polymerase is reacted. So, $Mg^{2+}$ isolated by PPase can be properly used for PCR by the action of Taq DNA polymerase, which results in the inhibition of the production of a non-specific PCR product. That is, only the target product can be produced. Therefore, the stabilized dried composition for hot-start PCR of the present invention comprising PPi and PPase could overcome the problems of the conventional master mix solution for hot-start PCR and not only has improved stability but also has ability to amplify target selectively, indicating precise amplification can be achieved.

The stabilized dried composition for hot-start PCR of the present invention has the following advantages, compared with the conventional PCR compositions:

1) Every component of PCR reaction mixture herein is mixed together and this mixture is dried before use. So, the mixing process is not necessary during PCR, which is advantageous in preventing an error by mixing. Other advantages are prevention of ineffectiveness of hot-start by PPase, inhibition of a non-specific PCR product, convenience in experiments, prevention of contamination by PCR product, stabilization of DNA polymerase and dNTPs, and improvement of reactivity.

2) A non-reactive dye or an additional stabilizer is added to nucleic acid, resulting in the improvement of usability and stability as well as having a long-term storagability.

3) The composition can be applied to general PCR processes and does not need long-time pre-treatment at high temperatures.

4) The dried composition for hot-start PCR of the present invention is more economical than the conventional PCR composition.

5) It is capable of preventing the generation of PCR product by low stringency priming, so that it can be effectively used for multiplex PCR using diverse samples simultaneously.

The present invention also provides a preparation method of the dried composition for hot-start PCR.

The preparation method of the present invention includes the steps of preparing a reaction mixture by mixing a reaction buffer, $MgCl_2$, 4 types of dNTPs, DNA polymerase, pyrophosphate and pyrophosphatase; and drying the reaction mixture.

The content of the pyrophosphate in the final reaction mixture is 0.3-5 mM, and more preferably 0.95-3.0 mM. The content of the pyrophosphatase is 30-200 mU/20 μl and more preferably 50-100 mU. DNA polymerase is one or more enzymes selected from the group consisting of the polymerase having the activity of 5'→3' exonuclease, the polymerase having the activity of 3'→5' exonuclease, and the polymerase having none of the activities of 5'→3' exonuclease and 3'→5' exonuclease.

The reaction mixture may further comprise one or more components selected from the group consisting of primers or probes, a fluorescent dye binding to DNA, template nucleic acid, a dye non-reactive to nucleic acid, polyol, gelatin, bovine serum albumin, Thesit and PEG-8000. The fluorescent dye is selected from the group consisting of SyBr Green, EtBr and HRdye. The dye is selected from the group consisting of rhodamine, tamra, lax, bromophenol blue, xylene cyanole, bromocresol red, and cresol red.

The present invention also provides a kit for hot-start PCR composed of the said dried composition for hot-start PCR. The kit can be prepared by the conventional construction method for PCR kit.

The present invention also provides a method for amplifying nucleic acid using the said dried composition for hot-start PCR.

The method comprise the following steps; mixing a sample comprising template nucleic acid and the dried composition for hot-start PCR; inducing a reaction to amplify the reaction mixture; and analyzing the amplified product of the template nucleic acid. At this time, PCR is performed by multiplex PCR, real-time PCR or real-time quantitative PCR.

Advantageous Effect

As explained hereinbefore, the dried composition for hot-start PCR of the present invention has improved stability at room temperature and long-term storagability, compared with the conventional compositions, so that it is stored at room temperature over a long period and has reproducibility. In addition, the composition includes every necessary component, so that it can be effectively used for not only multiplex PCR but also real-time quantitative PCR.

BRIEF DESCRIPTION OF THE DRAWINGS

The application of the preferred embodiments of the present invention is best understood with reference to the accompanying drawings, wherein.

EXAMPLES

Figure 1:
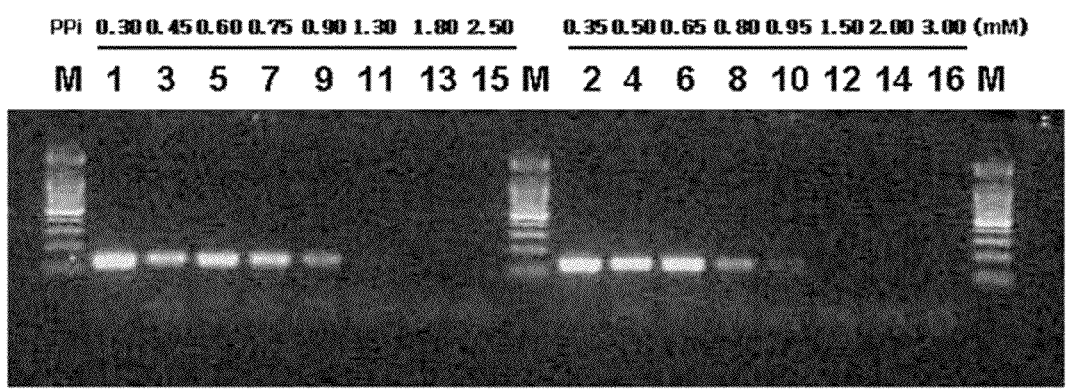
FIG. 1 is a photograph illustrating the result of agarose gel electrophoresis, in which PPi concentration that can inhibit PCR reaction is presented. Lane 1-lane 16 presents the results over different PPi concentrations of respectively 0.30 mM, 0.35 mM, 0.45 mM, 0.50 mM, 0.60 mM, 0.65 mM, 0.75 mM, 0.80 mM, 0.90 mM, 0.95 mM, 1.30 mM, 1.50 mM, 1.80 mM, 2.00 mM, 2.50 mM and 3.00 mM. M indicates 100 bp DNA size ladder marker (Bioneer corporation, republic of Korea).

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Concentration of PPi to Inhibit PCR

In the previous patent application (Korean Patent Application No: 10-1999-0004361), the present inventors investigated PPi concentration capable of inhibiting PCR reaction using *Yersinia pestis* genomic DNA having a low copy number as a template. And in this invention, the present inventors tried to determine PPi concentration capable of inhibiting low stringency priming not only with a target DNA having a low copy number but also with a target DNA having a high copy number.

First, the premix (10 mM Tris-HCl pH 9.0, 40 mM KCl, 1.5 mM $MgCl_2$, each 250 μM of 4 types of dNTPs, 1 U Taq DNA polymerase and a stabilizer, Bioneer corporation, republic of Korea) containing Taq DNA polymerase was used. 5.0 ng of lambda DNA was used as a template DNA. L137_F primer represented by SEQ. ID. NO: 1 generating 137 bp long PCR product and L137_R primer represented by SEQ. ID. NO: 2 were used respectively for PCR by 10 pmole per 20 μl reaction. PPi was added at different concentrations of 0.30, 0.35, 0.45, 0.50, 0.60, 0.65, 0.75, 0.80, 0.90, 0.95, 1.30, 1.50, 1.80, 2.0, 2.5 and 3.00 mM.

PCR was performed as follows; predenaturation at 94° C. for 5 minutes, denaturation at 94° C. for 30 seconds, annealing at 53° C. for 40 seconds, extension at 72° C. for 40 seconds, 36 cycles from denaturation to extension, and final extension at 72° C. for 5 minutes. The result of PCR was confirmed by electrophoresis using 0.5×TBE buffer (Trizma base, Boric Acid and 0.5 M EDTA, pH 8.0) containing 2.0% agarose.

As a result, an amplified product was not generated from PCR using lambda DNA having a high copy number when at least 0.95 mM of PPi was added (see lanes 10-16, FIG. 1). The above result indicates that PCR reaction can be interrupted by a certain amount of PPi, and at this time when a target DNA has a high copy number, at least 0.95 mM of PPi, more preferably at least 2.0 mM of PPi is required to inhibit the reaction. As PPi concentration decreases, PCR reaction inhibition effect decreases.

Example 2

PPase Activity Recovering PCR Reaction at High PPi Concentration

In the previous patent document (Korean Patent Application No: 10-1999-0004361), the present inventors investigated PPase activity to recover PCR reaction using *Yersinia pestis* genomic DNA having a low copy number as a template DNA.

And in this invention, the present inventors tried to determine PPase concentration capable of recovering PCR reaction inhibited by PPi not only with a target DNA having a low copy number but also with a target DNA having a high copy number.

First, the premix (10 mM Tris-HCl pH 9.0, 40 mM KCl, 1.5 mM $MgCl_2$, each 250 μM of 4 types of dNTPs, 1 U Taq DNA polymerase and polyol, Bioneer corporation, republic of Korea) containing Taq DNA polymerase and the premix (10 mM Tris-HCl pH 9.0, 40 mM KCl, 1.5 mM $MgCl_2$, each 250

μM of 4 types of dNTPs, 1 U Pfu DNA polymerase, 0.01% Tween 20 and polyol, Bioneer corporation, republic of Korea) containing Pfu DNA polymerase were prepared. 2.5 ng of lambda DNA was used as a template DNA. L137_F primer represented by SEQ. ID. NO: 1 generating 137 bp long PCR product and L137_R primer represented by SEQ. ID. NO: 2 were used respectively for PCR by 10 pmole per 20 μl reaction. PPi was added to inhibit PCR reaction at the concentration of 1.0 mM. To recover PCR reaction inhibited by PPi, PPase (SibEnzyme Ltd.) was added at different concentrations of 200, 100, 50, 25, 12.5, 6.3, 3.2, 1.6, 0.8, 0.4, 0.2 and 0.1 mU per 20 μl reaction respectively. PCR and electrophoresis were performed in the same manner as described in Example 1.

Figure 2:
FIG. 2 is a photograph illustrating the result of agarose gel electrophoresis, in which PPase activity recovering PCR reaction at high PPi concentration is presented. Lane 1-lane 16 presents the results of the reactions using Taq DNA polymerase. Lane 1 and lane 2 indicate negative controls not-treated with PPi and PPase, lane 3 and lane 4 indicate the cases only treated with 1.0 mM of PPi, and lane 5-lane 16 illustrate the results of PCR performed commonly in the presence of 1.0 mM PPi but with different PPase concentrations of 200, 100, 50, 25, 12.5, 6.3, 3.2, 1.6, 0.8, 0.4, 0.2, and 0.1 mU stepwise. Lane 17-lane 32 illustrate the results of the reactions using Pfu DNA polymerase. Lane 17 and lane 18 indicate negative controls not-treated with PPi and PPase, lane 19 and lane 20 indicate the cases only treated with 1.0 mM of PPi, and lane 21-lane 32 illustrate the results of PCR performed commonly in the presence of 1.0 mM PPi but with different PPase concentrations of 200, 100, 50, 25, 12.5, 6.3, 3.2, 1.6, 0.8, 0.4, 0.2, and 0.1 mU stepwise. M indicates 100 bp DNA size ladder marker.

As a result, when 3.2 mU-200 mU of PPase was treated, both PCRs respectively using Taq DNA polymerase and Pfu DNA polymerase were recovered to generate amplified products. In particular, when PPase was treated at the concentration of 12.5 mU-100 mU, PCR reactivity was almost the same as that of the control not-treated with PPi and PPase (FIG. 2). This result indicates that PPase can effectively recover the PCR reaction inhibited by PPi, suggesting that PCR reactivity can be increased which has been inhibited by PPi in order to suppress the generation of a non-specific PCR product during hot-start PCR.

Example 3

Measurement of PPase Activity Recovering PCR Reaction at Low PPi Concentration

The premix (10 mM Tris-HCl pH 9.0, 40 mM KCl, 1.5 mM MgCl$_2$, each 250 μM of 4 types of dNTPs, 1 U Taq DNA polymerase and polyol) containing Taq DNA polymerase was used. 2.0 ng of human genomic DNA was used as a template DNA. P65 primer represented by SEQ. ID. NO: 20 generating 1.5 kbp long PCR product and p83 primer represented by SEQ. ID. NO: 21 were used respectively for PCR by 10 pmole per 20 μl reaction. PPi was added to inhibit PCR reaction at the concentration of 0.15-0.25 mM. To recover PCR reaction inhibited by 0.25 mM of PPi, PPase (SibEnzyme Ltd.) was added at different concentrations of 300, 200, 100, 50 and 10 mU per 20 μl reaction respectively. PCR and electrophoresis were performed in the same manner as described in Example 1.

Figure 3:
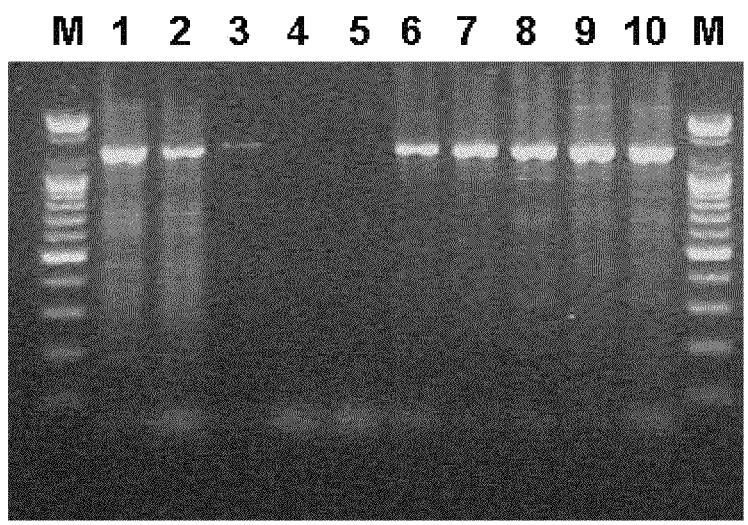
FIG. 3 is a photograph illustrating the result of agarose gel electrophoresis, in which PPase activity recovering PCR reaction at low PPi concentration is presented. Lane 1 and lane 2 indicate negative controls not-treated with PPi and PPase. Lane 3-lane 5 indicate the results of the reactions performed with 0.15, 0.2, and 0.25 mM of PPi stepwise. Lane 6-lane 10 illustrate the results of PCR performed commonly with 0.25 mM of PPi but with different PPase concentrations of 300, 200, 100, 50 and 10 mU stepwise. M indicates 100 bp DNA size ladder marker.

As a result, a non-specific reaction product was generated in the negative control (lanes 1 and 2, FIG. 3). When 0.15 mM of PPi was treated, Mg$^{2+}$ was not completely captured, so that a small amount of the amplified product was generated (lane 3, FIG. 3). When PPi was treated at equal amount for each PCR, when PPase concentration was over 300 mU, the amplified product was significantly reduced by the decrease of PCR reactivity. In the meantime, when PPase was added up to 50 mU, the non-specific reaction product was not inhibited and the target-specific product was not increased (lanes 6-10, FIG. 3).

Example 4

Multiplex PCR Using PPi and PPase

To confirm the hot-start effect in the amplified products generated at the said PPi and PPase concentrations, multiplex PCR was performed. To do so, 2.0 mM PPi and 60 mU or 80 mU PPase (SibEnzyme Ltd.) were added to the premix (10 mM Tris-HCl pH 9.0, 40 mM KCl, 1.5 mM MgCl$_2$, 4 dNTPs (250 μM each), 1 U Taq DNA polymerase, 0.01% Tween 20 and polyol) (AccuPower® PCR PreMix, Bioneer corporation, republic of Korea), which was then dried (referred as 'premix 1' and 'premix 3' hereinafter). And 2.0 mM PPi, primer and 60 mU or 80 mU PPase (SibEnzyme Ltd.) were added to the said premix, which was then dried (referred as 'premix 2' and 'premix 4' hereinafter). As a control, AccuPower® PCR PreMix (Bioneer corporation, republic of Korea) or AccuPower® Hotstart PCR PreMix (Bioneer corporation, republic of Korea) (10 mM Tris-HCl pH 9.0, 40 mM KCl, 1.5 mM MgCl$_2$, 4 dNTPs (250 μM each), 0.01% Tween 20 and polyol, containing 20n mAb and 0.25 U Taq DNA polymerase per 20 min reaction mixture) was used.

2.0 mM PPi and 60 mU or 80 mU PPase (SibEnzyme Ltd.) were added to the conventional premix (10 mM Tris-HCl pH 9.0, 40 mM KCl, 1.5 mM MgCl$_2$, 4 dNTPs (250 μM each), 1 U Taq DNA polymerase, 1 U Pfu DNA polymerase, 0.01% Tween 20 and a stabilizer) (AccuPower® HL PCR PreMix, Bioneer corporation, republic of Korea), which was then dried (referred as 'premix 5' and 'premix 7' hereinafter). And 2.0 mM PPi, primer and 60 mU or 80 mU PPase (SibEnzyme Ltd.) were added to the said premix, which was then dried (referred as 'premix 6' and 'premix 8' hereinafter). As a control, AccuPower® HL PCR PreMix (Bioneer corporation, republic of Korea) was used (Table 2).

At this time, 5 ng of human genomic DNA was used as a template DNA and the primer set comprising p53 primer (SEQ. ID. NO: 3) and p55 primer (SEQ. ID. NO: 4) generating 211 bp PCR product and the primer set comprising p55 primer (SEQ. ID. NO: 4) and p63 primer (SEQ. ID. NO: 5) generating 447 bp PCR product were used at the concentration of 5 pmol per 20 μl reaction.

TABLE 2

|  | Premix 1 | Premix 2 | Premix 3 | Premix 4 | Premix 5 | Premix 6 | Premix 7 | Premix 8 |
| --- | --- | --- | --- | --- | --- | --- | --- | --- |
| PPi(mM) | 2.0 | 2.0 | 2.0 | 2.0 | 2.0 | 2.0 | 2.0 | 2.0 |
| PPase(mU) | 60 | 60 | 80 | 80 | 60 | 60 | 80 | 80 |
| Primer | x | ○ | x | ○ | x | ○ | x | ○ |
| Common component | 10 mM TrisHCl pH 9.0, 40 mM KCl, 1.5 mM MgCl$_2$, dNTPs, 1 U Taq polymerase, 0.01% Tween 20, stabilizer | | | | 10 mM TrisHCl pH 9.0, 40 mM KCl, 1.5 mM MgCl$_2$, dNTPs, 1 U Taq and Pfu DNA polymerase, 0.01% Tween 20, stabilizer | | | |

Figure 4:
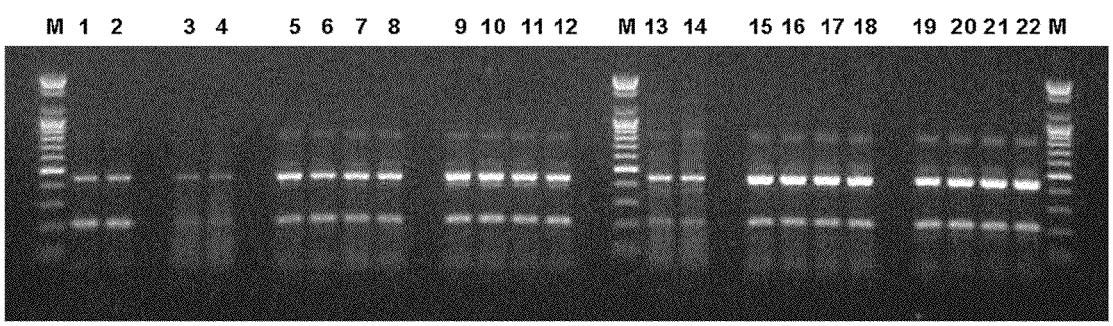
FIG. 4 is a photograph of agarose gel electrophoresis illustrating the result of multiplex PCR induced after a 2-hour pre-reaction of dried PCR premix containing PPi and PPase at 25° C. Lane 1 and lane 2 illustrate the results of PCR with AccuPower® Hotstart PCR PreMix (Bioneer corporation, republic of Korea). Lane 3 and lane 4 illustrate the results of PCR with AccuPower® PCR PreMix (Bioneer corporation, republic of Korea). Lane 5 and lane 6 illustrate the results of PCR performed after adding primers to PCR premix 1. Lane 7 and lane 8 illustrate the results of the reactions with PCR premix 2. Lane 9 and lane 10 indicate the results of the reactions induced after adding primers to PCR premix 3. Lane 11 and lane 12 illustrate the results of the reactions with PCR premix 4. Lane 13 and lane 14 illustrate the results of reactions with AccuPower® HL PCR PreMix (Bioneer corporation, republic of Korea). Lane 15 and lane 16 illustrate the results of PCR induced after adding primers to PCR premix 5. Lane 17 and lane 18 illustrate the results of PCR with premix 6. Lane 19 and lane 20 illustrate the results of the reactions performed after adding primers to premix 7. Lane 21 and lane 22 illustrate the results of PCR with premix 8. M indicates 100 bp DNA size ladder marker.
Figure 5:
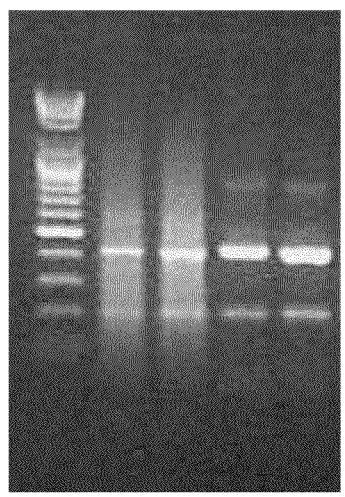
FIG. 5 is a photograph of agarose gel electrophoresis illustrating the result of multiplex PCR induced after a 2-hour pre-reaction of dried PCR premix containing PPi and PPase at 37° C. Lane 1 and lane 2 illustrate the results of PCR with AccuPower® HL PCR PreMix (Bioneer corporation, republic of Korea). Lane 3 and lane 4 illustrate the results of PCR with the premix prepared by adding 2.0 mM PPi and 80 mU PPase to AccuPower® HL PCR PreMix. M indicates 100 bp DNA size ladder marker.

To confirm the hot-start effect, the reaction mixture was left at 25° C. for 2 hours (FIG. 4) or at 37° C. for one hour (FIG. 5). Then, PCR was performed as follows; predenaturation at 94° C. for 5 minutes, denaturation at 95° C. for 15 seconds, annealing at 62° C. for 30 seconds, extension at 72° C. for 40 seconds, 35 cycles from denaturation to extension, and final extension at 72° C. for 5 minutes. In the meantime, the control PCR with AccuPower® Hotstart PCR PreMix (Bioneer corporation, republic of Korea) was performed as follows; staying at 25° C. for 2 hour, predenaturation at 95° C. for 15 minutes, denaturation at 95° C. for 15 seconds, annealing at 62° C. for 30 seconds, extension at 72° C. for 40 seconds, 35 cycles from denaturation to extension, and final extension at 72° C. for 5 minutes. The result of PCR was confirmed by electrophoresis using 0.5×TBE buffer containing 2.0% agarose.

From the result of PCR using Taq DNA polymerase, it was confirmed that both the dried premix containing PPi, PPase and primer and the premix first added with PPi and PPase and then dried before added with primer demonstrated high PCR reactivity and high specificity (lanes 5-12, FIG. 4), unlike the control AccuPower® PCR PreMix demonstrating low PCR reactivity and smeared band (lanes 3 and 4, FIG. 4). From the comparison with AccuPower® Hotstart PCR PreMix (Bioneer corporation, republic of Korea) (lanes 1 and 2, FIG. 4) using monoclonal antibody against DNA polymerase, it was also confirmed that the said premixes exhibited high PCR reactivity and reaction specificity. From the result of PCR using Taq DNA polymerase and Pfu DNA polymerase, it was also confirmed that the premix dried after added with PPi, PPase and primer and the premix added with PPi and PPase and dried before added with primer demonstrated higher PCR reactivity and specificity (lanes 15-22, FIG. 4 or lanes 3 and 4, FIG. 5) than AccuPower® HL PCR premix showed (lanes 13 and 14, FIG. 4). The smeared band was significantly reduced with those premixes.

Therefore, PPase used in this invention was confirmed to recover PCR reaction inhibited by PPi efficiently, suggesting that the non-specific PCR product was inhibited but PCR reactivity was increased which means it is advantageous for hot-start PCR. In particular, a target DNA could be specifically amplified even at a low temperature where a non-specific PCR product was easily generated. Inhibition of non-specific amplification and increase of PCR reactivity were also confirmed in various other PCR products (FIG. 4 and FIG. 5).

Example 5

Stability of the Dried Premix Containing PPi and PPase

To investigate thermo-stability of the dried premix, 2.0 mM PPi and 80 mU PPase (SibEnzyme Ltd.) were added to AccuPower® HL PCR PreMix (Bioneer corporation, republic of Korea), followed by drying to prepare the dried premix. The premix not containing 2.0 mM PPi and 80 mU PPase (SibEnzyme Ltd.) was used for the control. Drying was performed with 10 µl of 2× solution for 20 µl reaction in super centra evaporator at room temperature under vacuum condition for 30 minutes. At this time, 5 ng of human genomic DNA was used as a template DNA and the primer set comprising p53 primer represented by SEQ. ID. NO: 3 and p55 primer represented by SEQ. ID. NO: 4 generating 211 bp PCR product and the primer set comprising p55 primer represented by SEQ. ID. NO: 4 and p63 primer represented by SEQ. ID. NO: 5 generating 447 bp PCR product were used at the concentration of 5 pmol per 20 µl reaction.

Figure 6:
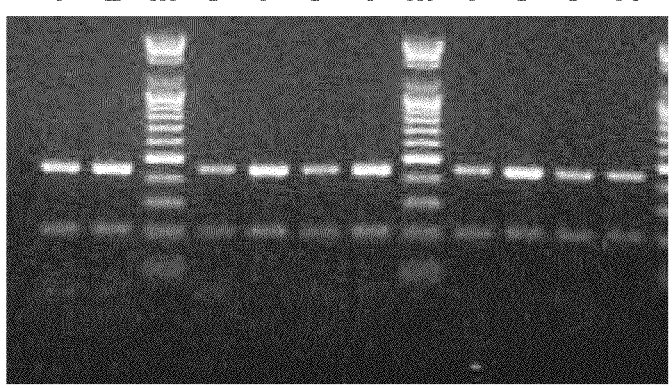
FIG. 6 is a photograph illustrating the result of agarose gel electrophoresis, in which time-course stability of dried premix comprising PPi, PPase, Taq DNA polymerase and Pfu DNA polymerase at the reaction temperature of 50° C. is presented. Lanes 1, 3, 5, 7 and 9 illustrate the results of PCR with the composition of the present invention performed in a 50° C. reactor and left therein for 0, 1, 2, 3, and 4 days. Lanes 2, 4, 6, 8 and 10 illustrate the results of PCR with AccuPower® HL PCR PreMix performed in a 50° C. reactor and left therein for 0, 1, 2, 3, and 4 days.

The dried composition prepared above was left in a 50° C. reactor. Sampling was performed from day 0 to day 4 every day. The obtained samples were stored in a refrigerator until used for PCR. PCR and electrophoresis were performed in the same manner as described in Example 1 to confirm the PCR product. As a result, the premix of the present invention containing 2.0 mM of PPi and 80 mU of PPase and the control premix have demonstrated PCR reactivity until day 4 since they were left at 50° C. (FIG. 6).

The stability was compared between the conventional master mix and the dried premix of the present invention. To do so, hot-start master mix solution was prepared, which stood at room temperature (25° C.-30° C.) for a while, followed by the stability test. The dried composition of the present invention was tested for stability at 50° C. over the time. The composition of 20 µl of the premix was as follows: 10 mM Tris-HCL pH 9.0, 40 mM KCl, 1.5 mM $MgCl_2$, 4 dNTPs (250 µM each), 1 U Taq DNA polymerase, 0.01% Tween 20, a stabilizer, 2 mM PPi and 500 U PPase.

After a while, PCR was performed as follows: one cycle at 30° C. for 4 hours, one cycle at 94° C. for 5 minutes, and then at 94° C. for 20 seconds, at 55° C. for 40 seconds and at 72° C. for 1 minute, which was repeated 32 cycles, followed by final extension at 72° C. for 5 minutes. The one cycle performed at 37° C. for 4 hours was to confirm the generation of the non-specific binding. 10 ng of human genomic DNA was used as a template to target p53 gene. The primer set of p75 (SEQ. ID. NO: 22)/P73 (SEQ. ID. NO: 23) was used for lane 1, the primer set of P55 (SEQ. ID. NO: 4)/P53 (SEQ. ID. NO: 3) was used for lane 2, the primer set of P55 (SEQ. ID. NO: 4)/P63 (SEQ. ID. NO: 5) was used for lane 3, the primer set of p75 (SEQ. ID. NO: 22)/p83 (SEQ. ID. NO: 21) was used for lane 4, the primer set of p55 (SEQ. ID. NO: 4)/p73 (SEQ. ID. NO: 23) was used for lane 5, the primer set of p65 (SEQ. ID. NO: 20)/p83 (SEQ. ID. NO: 21) was used for lane 6, the primer set of p55 (SEQ. ID. NO: 4)/p83 (SEQ. ID. NO: 21) was used for lane 7. The results are shown in FIG. 7 and FIG. 8.

Figure 7:
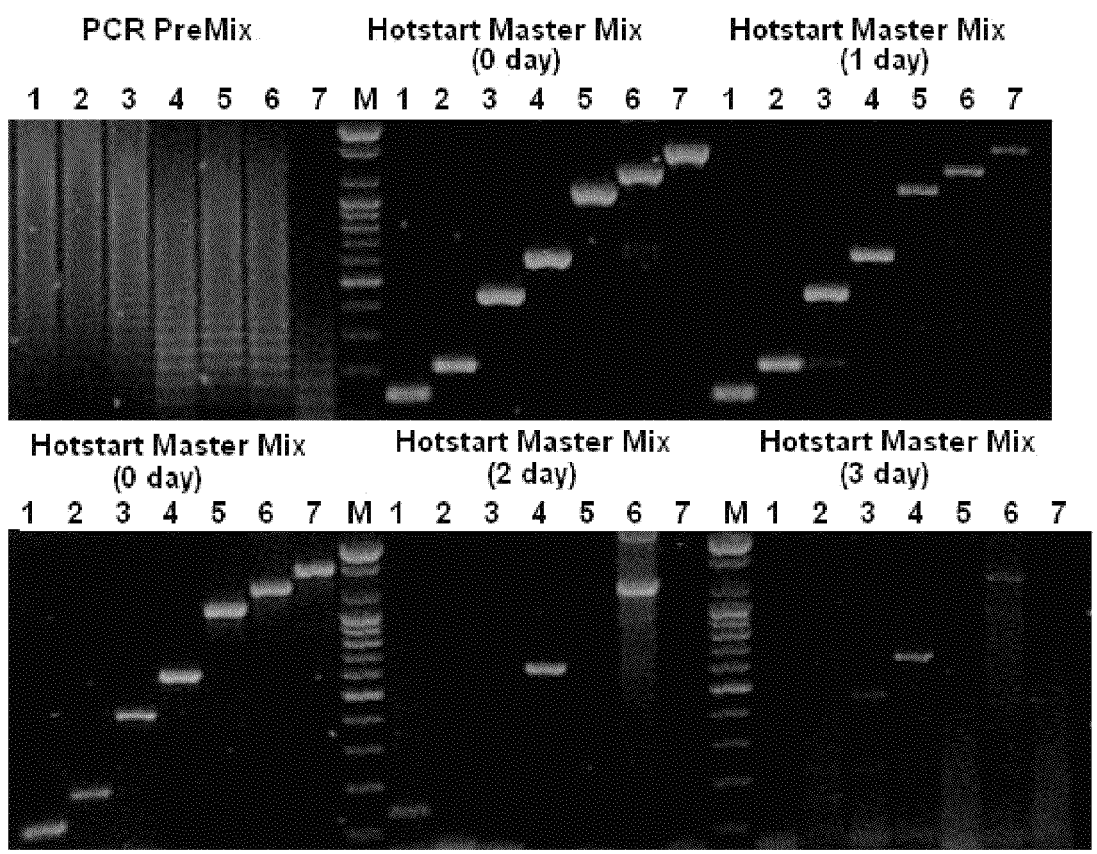
FIG. 7 illustrates the stability of hot-start master mix solution.
Figure 8:
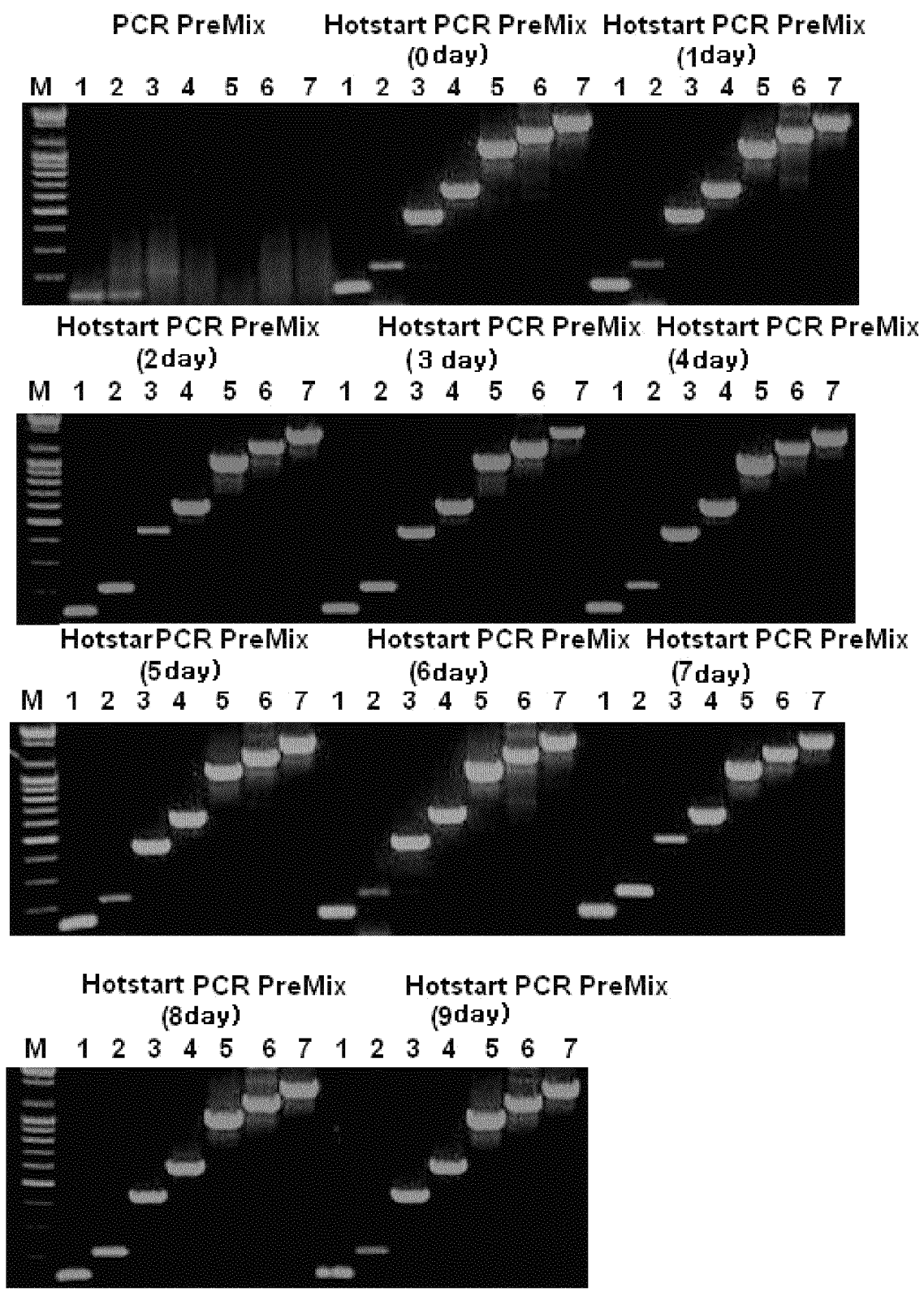
FIG. 8 illustrates the stability of the dried composition of the present invention. Lanes 1, 2, 3, 4, 5, 6, 7 and M indicate 139 bp, 211 bp, 447 bp, 618 bp, 1082 bp, 1296 bp, 1561 bp, and 100 bp DNA size ladder markers, respectively.

As shown in FIG. 7 and FIG. 8, the dried composition for hot-start PCR of the present invention retained reactivity even after being left for 9 days at 50° C. However, the conventional hot-start master mix solution did not have reactivity from the 2nd day after being left at room temperature without exhibiting the hot-start effect.

Example 6

Long PCR with the Dried Premix Containing PPi and PPase

PCR was performed using lambda DNA as a template with the dried premix containing PPi and PPase (SibEnzyme Ltd.) to produce the amplified products in different lengths. To do so, the dried compositions for hot-start PCR were prepared in the same manner as described in Example 5, that is 2.0 mM PPi and 80 mU PPase were commonly added to 1) the premix containing Taq DNA polymerase (comprising 10 mM Tris-HCl pH 9.0, 40 mM KCl, 1.5 mM $MgCl_2$, 4 dNTPs (250 µM each), 1 U Taq DNA polymerase, 0.01% Tween 20 and a stabilizer), 2) the premix containing Pfu DNA polymerase (comprising 10 mM Tris-HCl pH 9.0, 40 mM KCl, 1.5 mM $MgCl_2$, 4 dNTPs (250 µM each), 1 U Pfu DNA polymerase, 0.01% Tween 20 and a stabilizer), and 3) the premix containing both of Taq DNA polymerase and Pfu DNA polymerase (comprising 10 mM Tris-HCl pH 9.0, 40 mM KCl, 1.5 mM $MgCl_2$, 4 dNTPs (250 µM each), 1 U Taq DNA polymerase, 1 U Pfu DNA polymerase, 0.01% Tween 20 and a stabilizer).

20 ng of lambda DNA was used as a template DNA. To produce 500 bp-15.0 kbp products, L303050-F represented by SEQ. ID. NO: 6 was used as a forward primer and reverse primers represented by SEQ. ID. NO: 7-NO: 13 to produce 500 bp, 1 kbp, 2 kbp, 5.0 kbp, 10.0 kbp, 12.0 kbp and 15 kbp products were used. To produce 20.0 kbp product, the primer set composed of the primers represented by SEQ. ID. NO: 14 and NO: 15 was used. And also, to produce 30.0 kbp product, the primer set composed of the primers represented by SEQ. ID. NO: 16 and NO: 17 was used.

Reaction mixtures each containing Taq DNA polymerase and Taq DNA polymerase/Pfu DNA polymerase were left at 37° C. for 2 hours, followed by PCR as follows: predenaturation at 94° C. for 5 minutes, denaturation at 94° C. for 30 seconds, annealing & extension at 68° C. for minutes, 28 cycles from denaturation to extension, and final extension at 72° C. for 10 minutes. In the meantime, PCR with the premix containing Pfu DNA polymerase only was performed as follows; predenaturation at 94° C. for 5 minutes, denaturation at 94° C. for 30 seconds, annealing & extension at 68° C. for 20 minutes, 28 cycles from denaturation to extension, and final extension at 72° C. for 10 minutes. The result of PCR was confirmed by electrophoresis using 0.5×TBE buffer containing 1.0% agarose.

Figure 9:
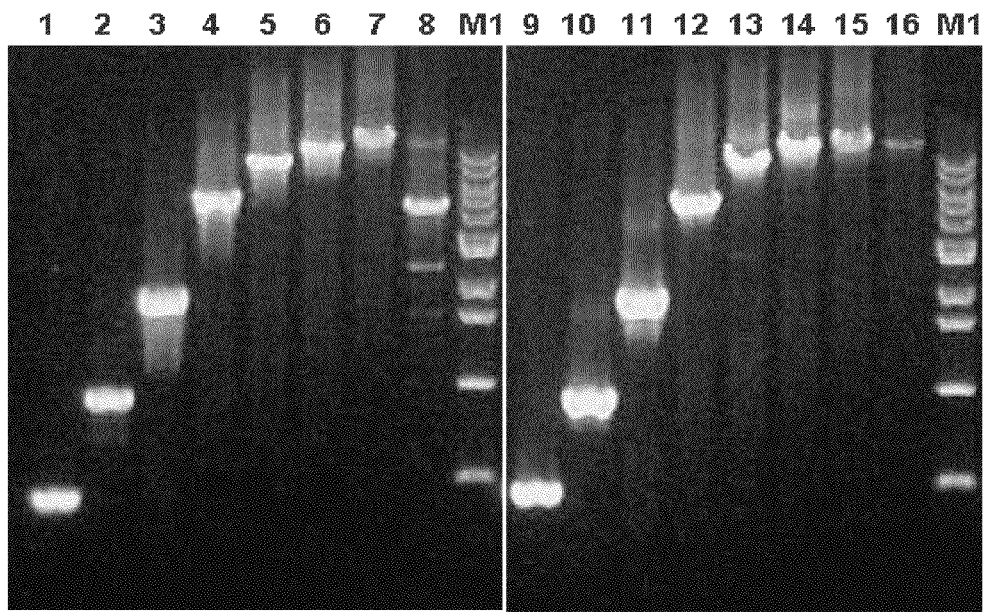
FIG. 9 is a photograph of agarose gel electrophoresis illustrating the result of Long kb PCR using lambda DNA with the dried premix containing PPi, PPase and Taq DNA polymerase and the dried premix containing Taq DNA polymerase only. Lane 1-lane 8 illustrate the results of Long kb PCR with the premix containing Taq DNA polymerase. Lane 9-lane 16 illustrate the results of Long kb PCR with the premix containing 2.0 mM PPi and 80 mU PPase and Taq DNA polymerase. Lane 1 and lane 9, lane 2 and lane 10, lane 3 and lane 11, lane 4 and lane 12, lane 5 and lane 13, lane 6 and lane 14, lane 7 and lane 15, lane 8 and lane 16 indicate the PCR results with the amplified products of respectively 500 bp, 1.0 kbp, 2.0 kbp, 5.0 kbp, 8.0 kbp, 10.0 kbp, 12.0 kbp, and 15.0 kbp. M1 indicates 1 kb DNA size ladder marker.
Figure 10:
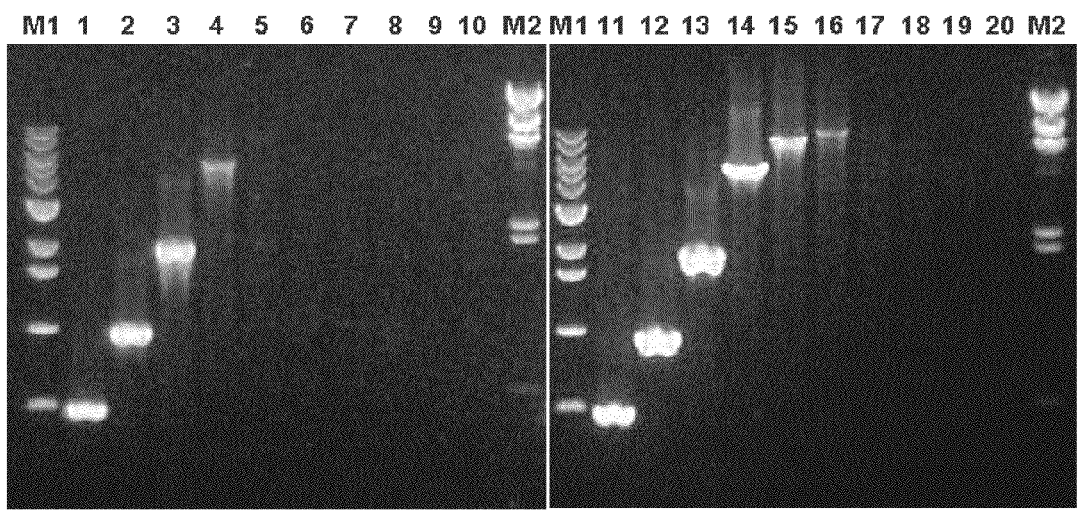
FIG. 10 is a photograph of agarose gel electrophoresis illustrating the result of Long kb PCR using lambda DNA with the dried premix containing PPi, PPase and Pfu DNA polymerase and the dried premix containing Pfu DNA polymerase only. Lane 1-lane 10 illustrate the results of Long kb PCR with the premix containing Pfu DNA polymerase. Lane 11-lane 20 illustrate the results of Long kb PCR with the premix containing 2.0 mM PPi and 80 mU PPase and Pfu DNA polymerase. Lane 1 and lane 11, lane 2 and lane 12, lane 3 and lane 13, lane 4 and lane 14, lane 5 and lane 15, lane 6 and lane 16, lane 7 and lane 17, lane 8 and lane 18, lane 9 and lane 19, and lane 10 and lane 20 indicate the PCR results with the amplified products of respectively 500 bp, 1.0 kbp, 2.0 kbp, 5.0 kbp, 8.0 kbp, 10.0 kbp, 12.0 kbp, 15.0 kbp, 20.0 kbp, and 30.0 kbp. M1 indicates 1 kb DNA size ladder marker and M2 indicates lambda/Hind III ladder marker.
Figure 11:
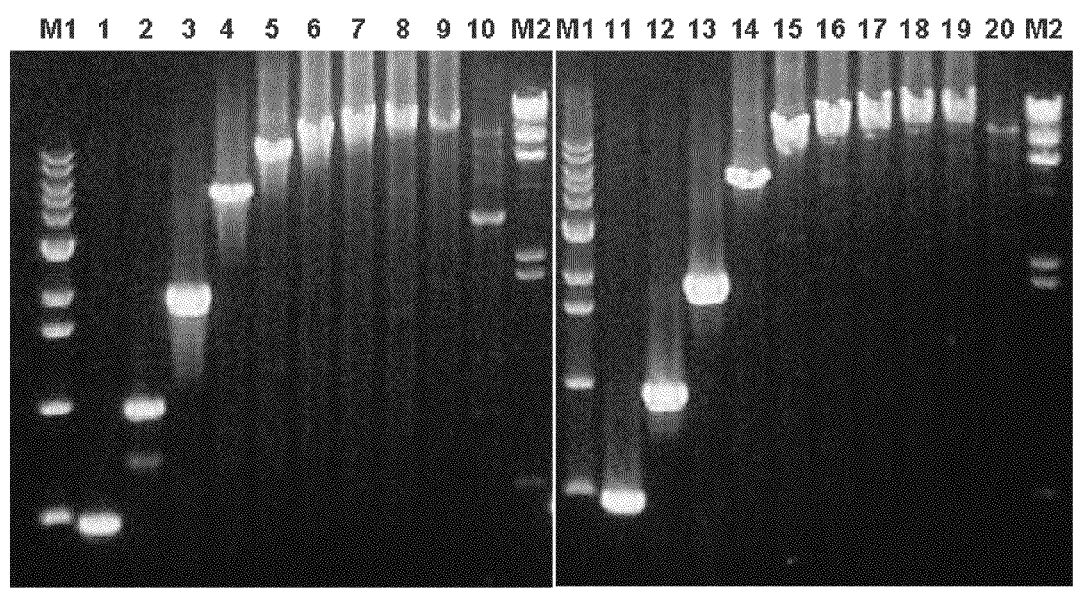
FIG. 11 is a photograph of agarose gel electrophoresis illustrating the result of Long kb PCR using lambda DNA with the dried premix containing PPi, PPase, Taq DNA polymerase and Pfu DNA polymerase and the dried premix containing Taq DNA polymerase and Pfu DNA polymerase. Lane 1-lane 10 illustrate the results of Long kb PCR with the premix containing Taq DNA polymerase and Pfu DNA polymerase and lane 11-lane 20 illustrate the results of Long kb PCR with the premix containing 2.0 mM PPi, 80 mU PPase, Taq DNA polymerase and Pfu DNA polymerase. Descriptions of each lane and size ladder marker are same as given in FIG. 10.

As a result, the premix containing 2.0 mM PPi, 80 mU PPase and Taq DNA polymerase demonstrated high PCR reactivity to amplify 500 bp-15.0 kbp DNA under every condition. In particular, significant inhibition of a non-specific reaction and high PCR reactivity, the hot-start effect, were confirmed with 15 kbp amplified product (FIG. 9). When PCR was performed with the premix containing Pfu DNA polymerase, reactivity was confirmed up to 5.0 kb, however when PCR was performed with the premix containing 2.0 mM PPi, 80 mU PPase and Pfu DNA polymerase, reactivity was confirmed up to 10.0 kb. That is, when PPi and PPase were treated together, significant inhibition of a non-specific reaction and high PCR reactivity, the hot-start effect, were confirmed (FIG. 10). It was also confirmed that when PCR was performed with the premix containing 2.0 mM PPi, 80 mU PPase, Taq DNA polymerase and Pfu DNA polymerase and when PCR was performed with the premix containing Taq DNA polymerase and Pfu DNA polymerase, reactivity was all confirmed up to 20.0 kb. Particularly, when PPi and PPase were treated together to generate 1.0 kb product, the non-specific reaction was eliminated (FIG. 11). That is, significant inhibition of a non-specific reaction and high PCR reactivity, the hot-start effect, were confirmed.

Example 7

Real-Time PCR Using Hot-Start Reactant Containing PPi and PPase

To investigate the hot-start effect of PCR composition containing PPi and PPase (SibEnzyme Ltd.) by real time PCR, a fluorescent material (Greenstar™, Bioneer corporation, republic of Korea) was added to 2×PCR premix solution (comprising 10 mM Tris-HCl pH 9.0, 50 mM KCl, 2.0 mM MgCl$_2$, 4 dNTPs (250 μM each), 1 U Taq DNA polymerase, 0.01% Tween 20 and a stabilizer) by 0.25× per 20 μl reaction, to which PPi and PPase were added respectively by 2.0 mM and 80 mU. For the control, a fluorescent material (Greenstar™, Bioneer corporation, republic of Korea) was added to 2×PCR premix solution (comprising 10 mM Tris-HCl pH 9.0, 50 mM KCl, 2.0 mM MgCl$_2$, 4 dNTPs (250 μM each), 1 U Taq DNA polymerase, 0.01% Tween 20 and a stabilizer) by 0.25× per 20 μl reaction. The above fluorescent material facilitates simple analysis without sequence specific fluorescent probe, simply by measuring fluorescence generated in double-stranded DNA produced during DNA amplification after intercalation of the fluorescent material.

1 ng of lambda DNA was used as a template DNA. L90_F primer represented by SEQ. ID. NO: 18 and L90_R primer represented by SEQ. ID. NO: 19 generating 90 bp PCR product were used respectively at the concentration of 10 pmol per 20 μl reaction. PCR was performed by using ABI 7500 Fast system (Applied Biosystems) as follows; predenaturation at 94° C. for 5 minutes, denaturation at 95° C. for 10 seconds, annealing at 60° C. for 15 seconds simultaneously with extension (40 cycles). After dissociation step, the melting curve of the amplified product was made to confirm PCR reactivity and specificity.

Figure 12:
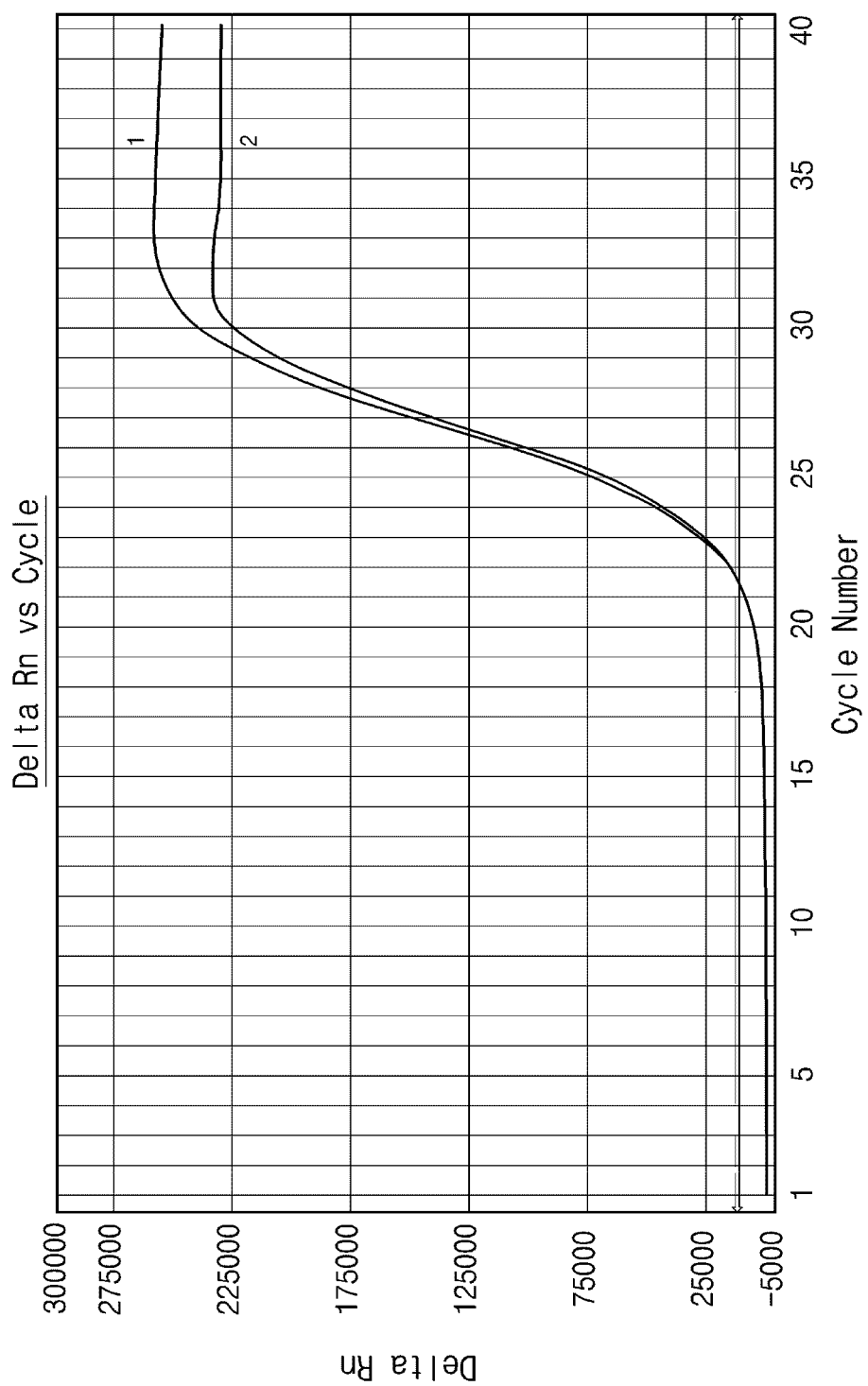
FIG. 12 is a graph presenting the curve illustrating the fluorescence measured by real-time PCR with the premix solution containing Taq DNA polymerase, PPi, PPase, and a fluorescent material (SyBr Green) and with the premix solution containing Taq DNA polymerase and a fluorescent material. In this graph, the horizontal axis presents a reaction cycle and the axis of ordinates indicates fluorescence measured according to the reaction cycle. Blue line 1 is the curve illustrating fluorescence detected in the experimental group and red line 2 is the curve illustrating fluorescence detected in the control group.

As a result, as shown in FIG. 12, threshold cycles (Ct) of line 1 and line 2 were both 21.19. So, PCR reactivity of real time quantitative PCR was equal whether PPi or PPase were treated or not.

Figure 13:
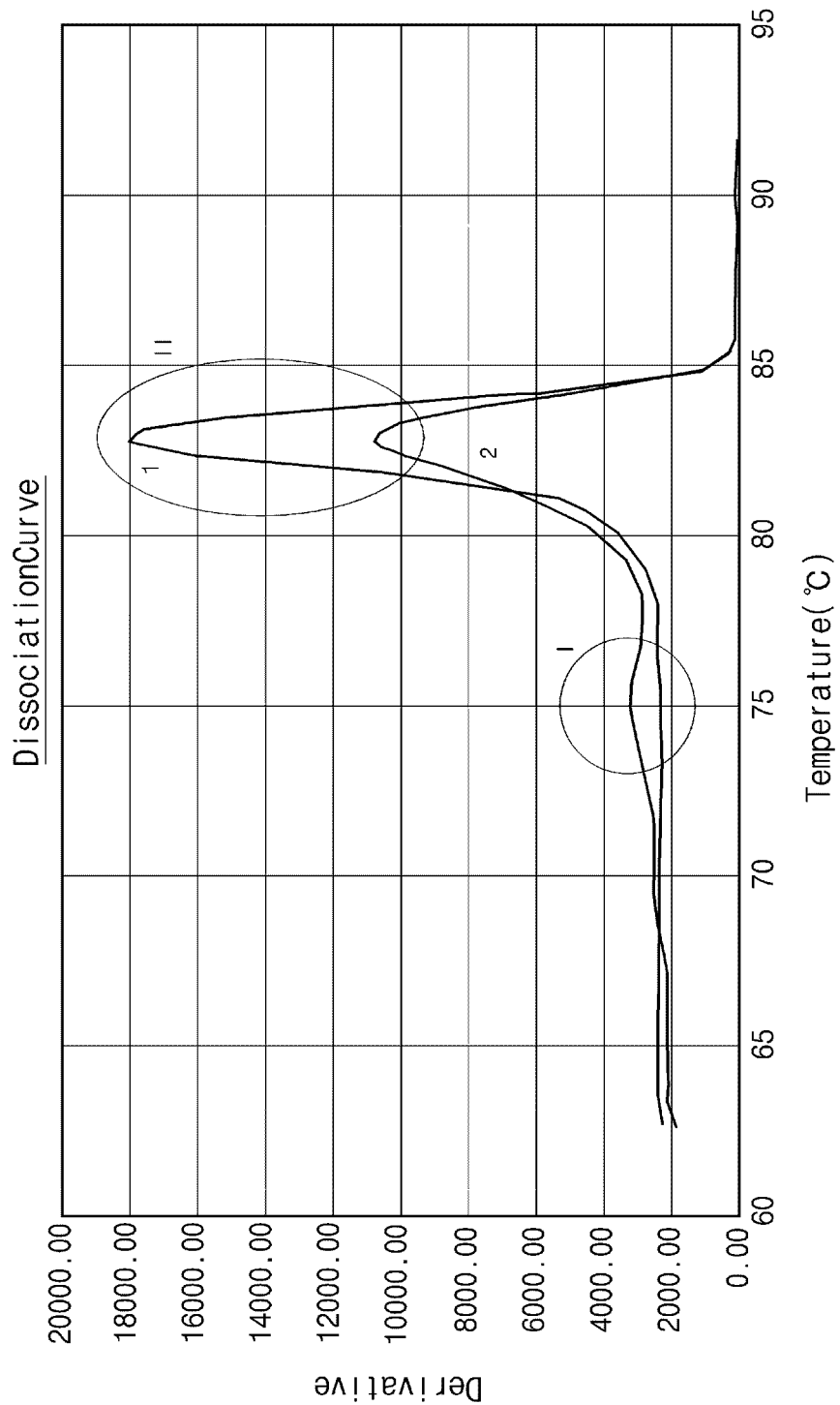
FIG. 13 is a graph presenting the melting curve using the fluorescence curve confirmed by real-time PCR which illustrates each PCR with the premix solution containing Taq DNA polymerase, PPi, PPase, and a fluorescent material (Greenstar™) and with the premix solution containing Taq DNA polymerase and a fluorescent material. In this graph, the horizontal axis illustrates the temperature changes and the axis of ordinates illustrates fluorescence measured according to the temperature rise. Red line 1 is the melting curve of the experimental group and light green line 2 is the melting curve of the control group.

As shown in FIG. 13, one clear fluorescent peak was observed in line 1 from PCR with PPi and PPase, indicating an accurate amplified product was generated. In the meantime, two amplified products were confirmed by two fluorescent peaks in line 2 from PCR without PPi and PPase, which means another small sized primer dimer amplified product was generated except the target product. Melting temperatures (Tm) of the target PCR products of the experimental group (line 1) and the control (line 2) were both 82.8° C. Melting temperature (Tm) of the primer dimer band was a little lower than that, which was 75° C.

From the above results, it was confirmed that PPase used in this invention recovered PCR reaction inhibited by PPi in real-time PCR, so it could inhibit non-specific PCR production, but increase PCR reactivity. On the contrary, in the control, primer dimer was generated in addition to the target PCR product, indicating low specificity.

Example 8

Real-Time Quantitative PCR Using Hot-Start Reactant Containing PPi and PPase

Hot-start effect by PPi and PPase was examined by real-time quantitative PCR. A fluorescent material (Greenstar™, Bioneer corporation, republic of Korea) was added to 2×PCR premix solution (comprising 10 mM Tris-HCl pH 9.0, 50 mM KCl, 2.0 mM MgCl$_2$, 4 dNTPs (250 μM each), 1 U Taq DNA polymerase, 0.01% Tween 20 and polyol) by 0.25× per 20 μl reaction, to which 2.0 mM PPi and 80 mU PPase (SibEnzyme Ltd.) were added, resulting in the preparation of composition 1. A fluorescent material (Greenstar™, Bioneer corporation, republic of Korea) was added to 2×PCR premix solution (comprising 10 mM Tris-HCl pH 9.0, 50 mM KCl, 2.0 mM MgCl$_2$, 4 dNTPs (250 μM each), 1 U Taq DNA polymerase, 0.01% Tween 20 and polyol) by 0.25× per 20 μl reaction, to which 0.5 mM PPi and 0.3 mU PPase (SibEnzyme Ltd.) were added, resulting in the preparation of composition 2. For the control, the fluorescent material was added to the 2×PCR premix solution by 0.25× per 20 μl reaction.

Figure 14:
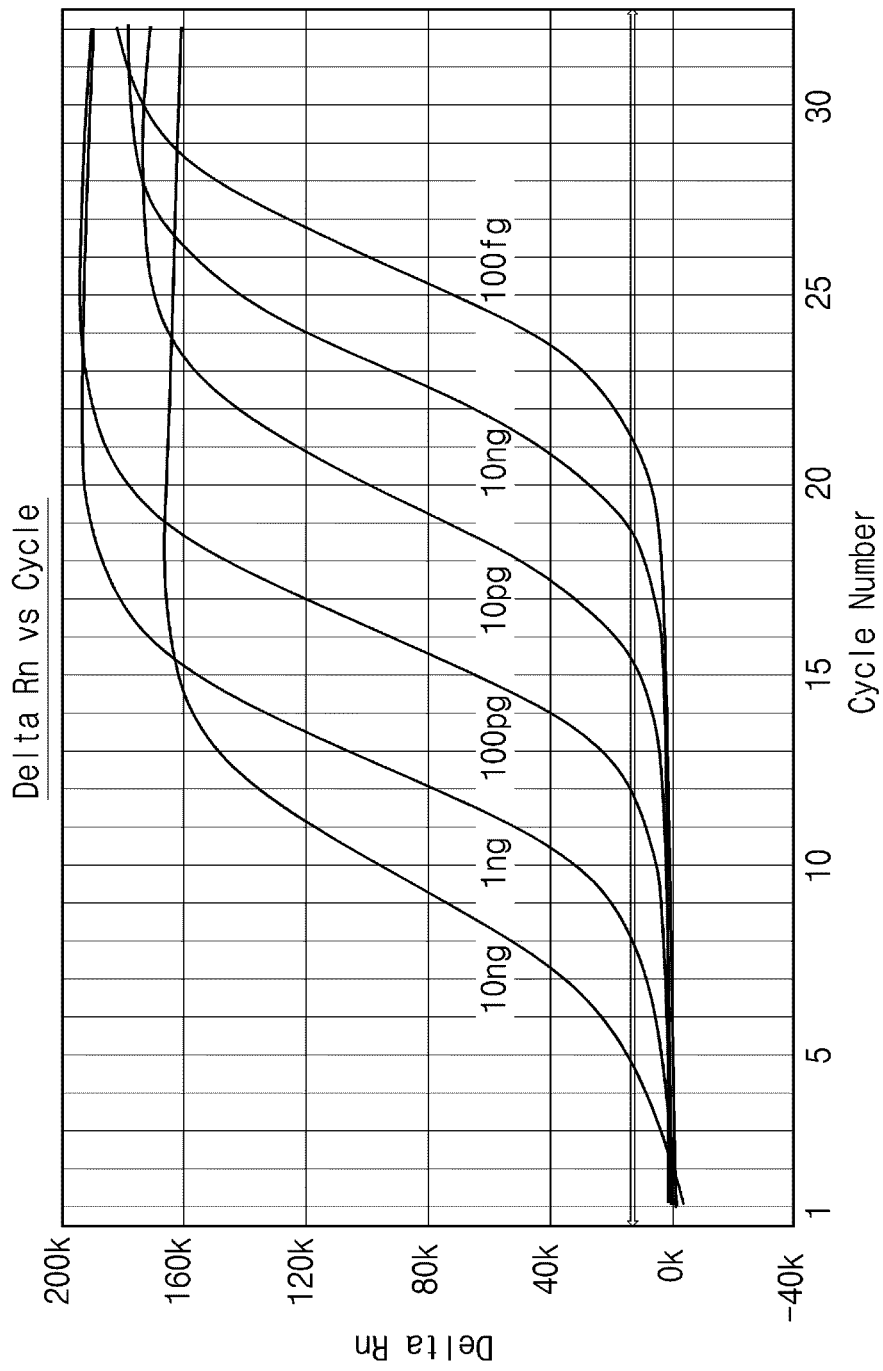
FIG. 14 is a graph illustrating the result of real-time quantitative PCR with the premix solution containing Taq DNA polymerase and a fluorescent material (Greenstar™). In this graph, the horizontal axis illustrates the reaction cycle (referred as "Cy." hereinafter) and the axis of ordinates illustrated fluorescence measured over the reaction cycle. Each curve illustrates the result of fluorescence measurement by real-time quantitative PCR with 10 ng, 1 ng, 100 pg, 10 pg, 1 pg or 100 fg of lambda DNA.
Figure 15:
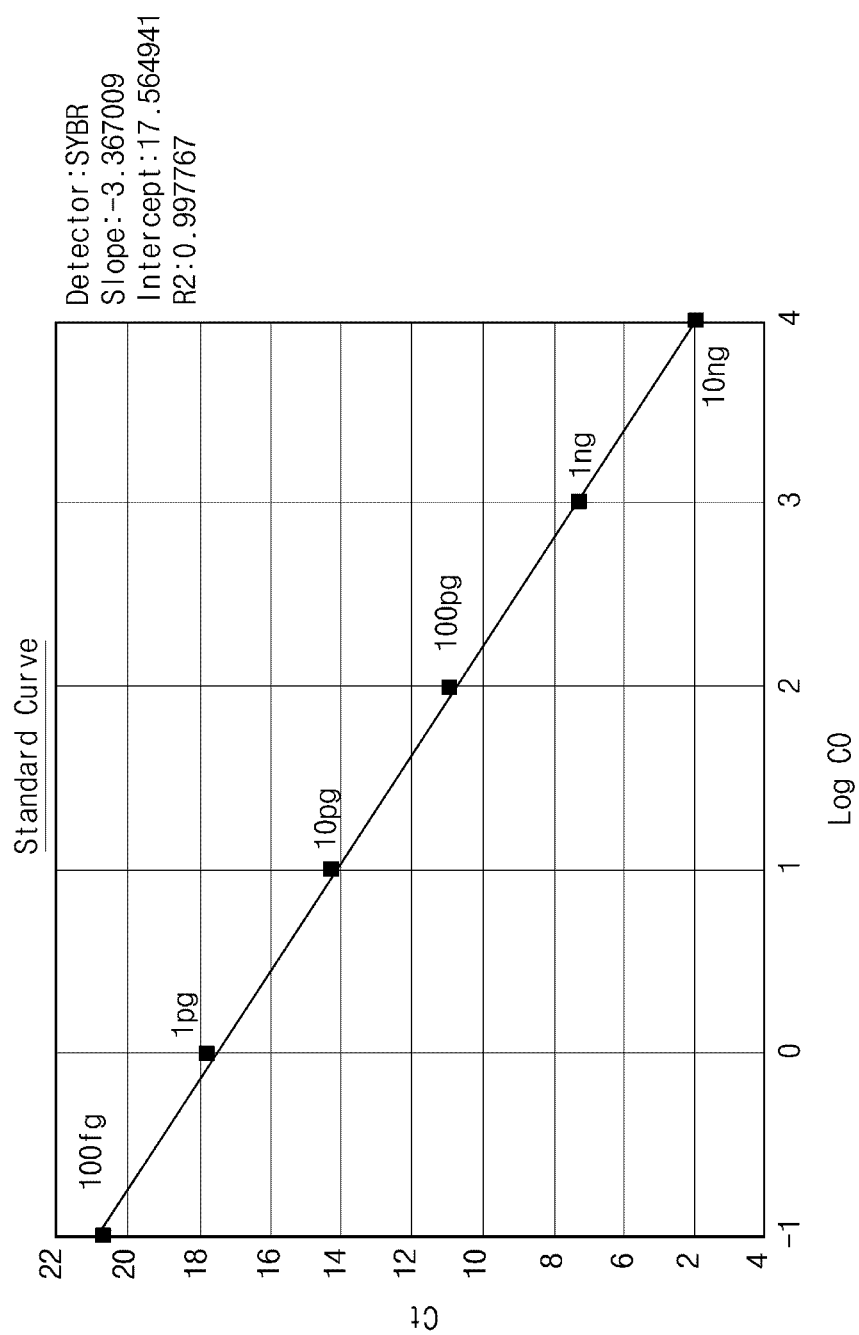
FIG. 15 is a graph illustrating the linearity of the quantitative curve made by using fluorescence curve according to the concentrations diluted stepwise in FIG. 14. In this graph, the horizontal axis indicates Log substituted numbers for the fluorescence measured and the axis of ordinates indicates the reaction cycles. Curves indicate the results of quantitative analysis with different concentrations of lambda DNA of 100 fg, 1 pg, 10 pg, 100 pg, 1 ng and 10 ng stepwise from the right top to the left bottom. According to the quantitative curve, efficiency of PCR was 98% and linearity of PCR was 0.9977.

The template DNA, lambda DNA, was diluted stepwise by 10-fold each time to 6 orders of 10 ng, 1 ng, 100 pg, 10 pg, 1 pg, and 100 fg. L90_F primer represented by SEQ. ID. NO: 18 and L90_R primer represented by SEQ. ID. NO: 19 generating 90 bp product were used at the concentration of 10 pmole per 20 μl reaction. PCR and melting curve drawing were performed in the same manner as described in Example 7. PCR efficiency (referred as "E" hereinafter) for the serially diluted templates and PCR linearity (referred as "R^2" hereinafter) were investigated and compared to confirm the hot-start effect (FIG. 14 and FIG. 15).

Figure 16:
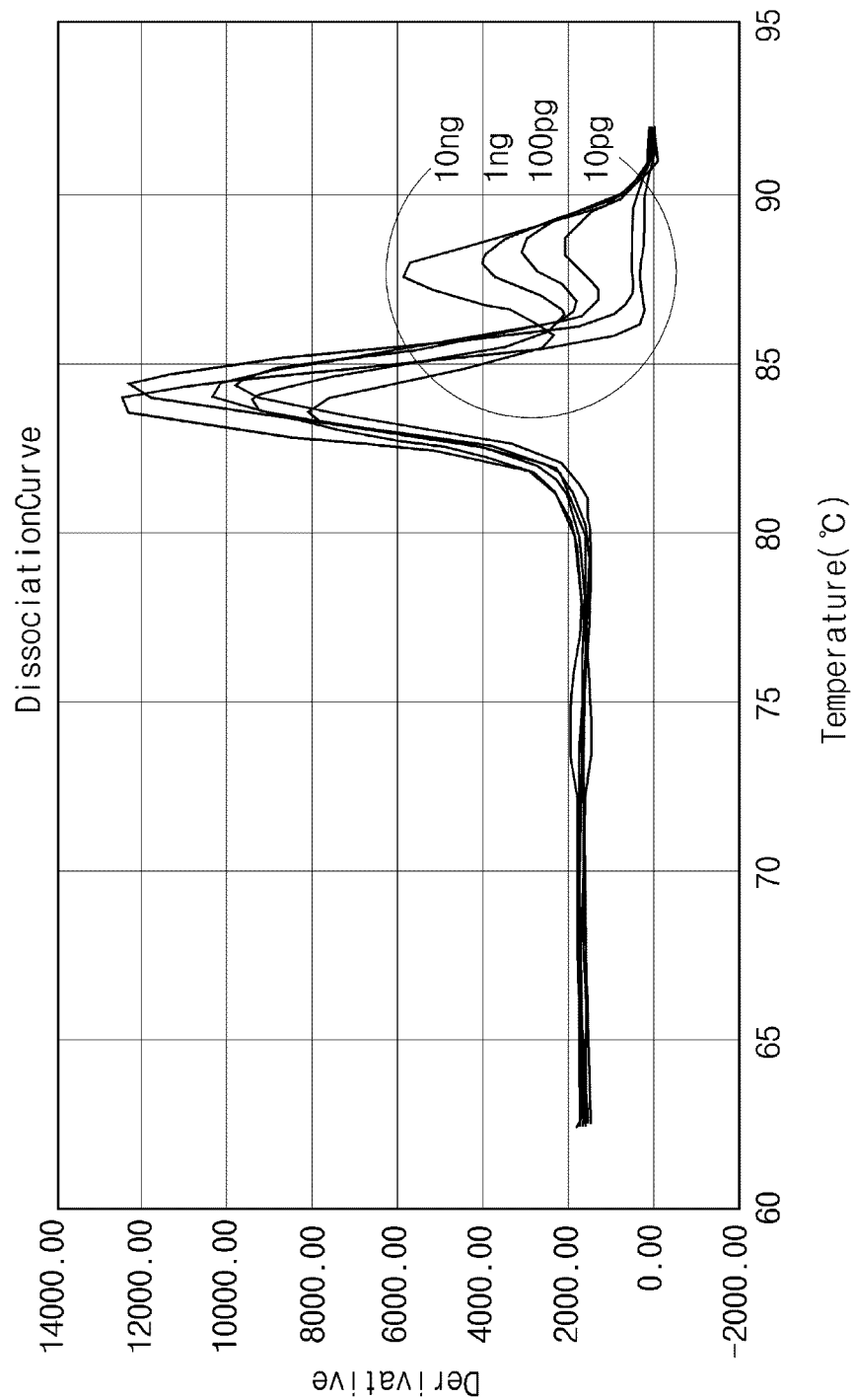
FIG. 16 is a graph illustrating the melting curve made by using the fluorescence graph of FIG. 14. In this graph, the horizontal axis indicates the temperature changes and the axis of ordinates indicates the fluorescence measured over the temperature rise.
Figure 17:
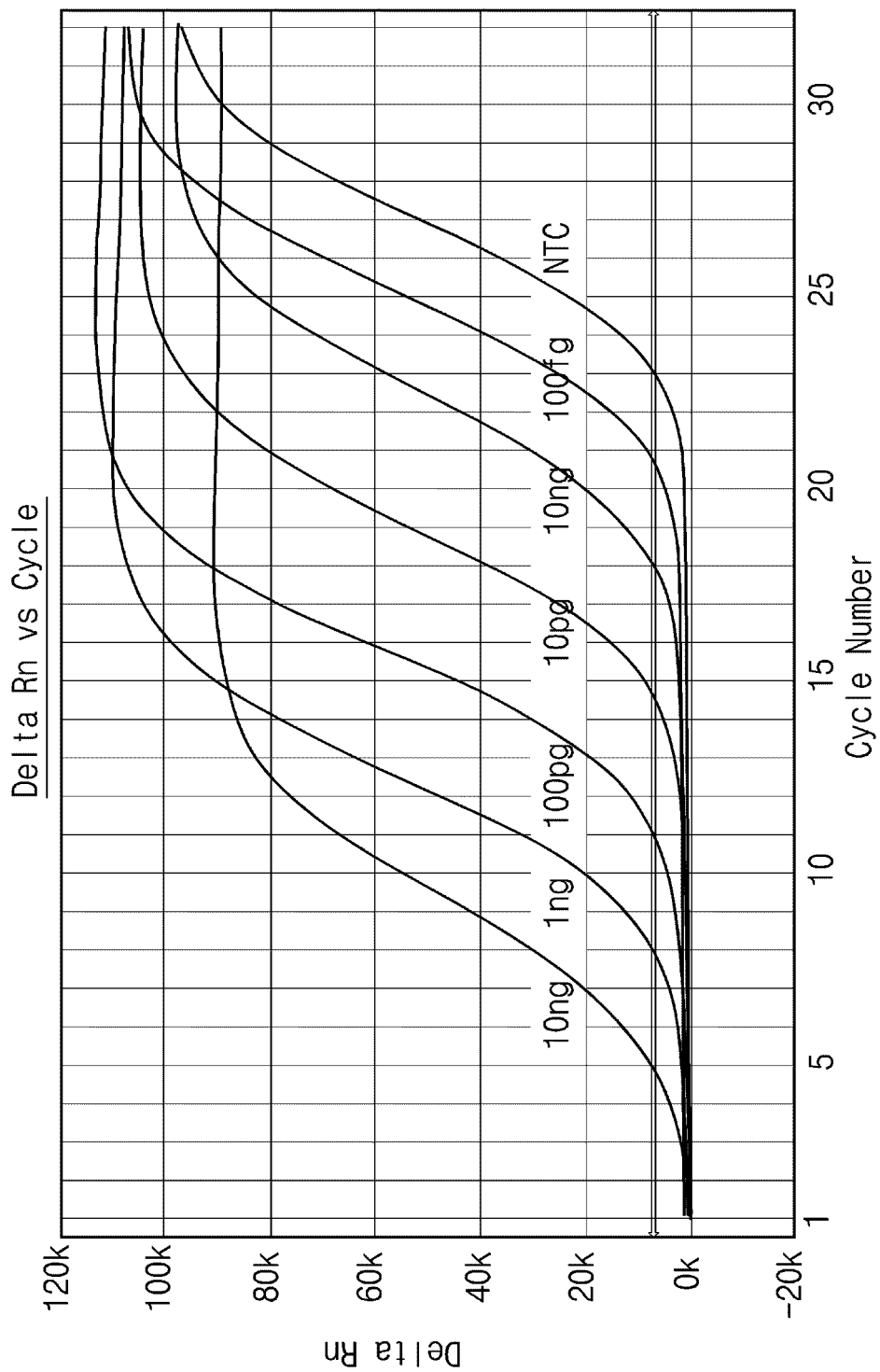
FIG. 17 is a graph illustrating the result of real-time quantitative PCR with the premix solution containing Taq DNA polymerase, a fluorescent material (Greenstar™), 0.5 mM PPi and 0.3 mU PPase. In this graph, the horizontal axis and the axis of ordinates are the same as described in FIG. 14.
Figure 18:
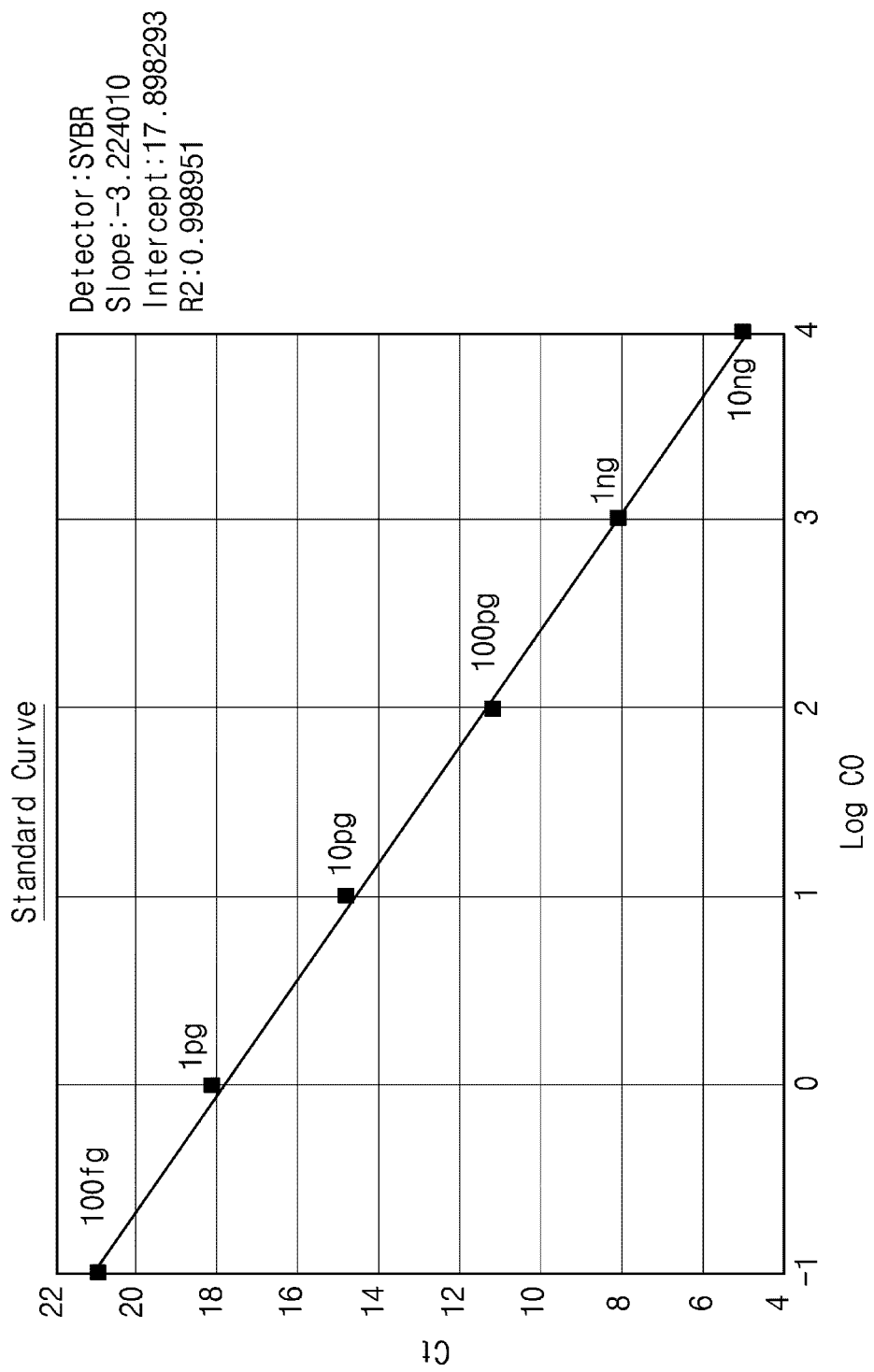
FIG. 18 is a graph illustrating the linearity of the quantitative curve made by using fluorescence curve according to the concentrations diluted stepwise in FIG. 17. In this graph, the horizontal axis and the axis of ordinates are the same as described in FIG. 15. According to the quantitative curve, efficiency of PCR was 104% and linearity of PCR was 0.9989.

As shown in FIG. 16, a fluorescent peak was observed at 87.5° C. in the control, unlike the fluorescent peak confirmed at 75° C. in FIG. 13. That is, the fluorescent peak presenting the target PCR product was the one observed at the melting temperature (Tm) of 82.8° C. and the other fluorescent peak observed at the melting temperature of 87.5° C. presented a non-specific reaction product. From the top to the bottom in the melting curve, the concentration of lambda DNA was diluted stepwise from 10 ng, 1 ng, 100 pg and 10 pg. The results of real-time quantitative PCR shown in FIG. 14 and FIG. 15 indicate that a non-specific reaction product was generated. Therefore, these results could not be considered as precise quantitative PCR results (FIG. 17 and FIG. 18).

Figure 19:
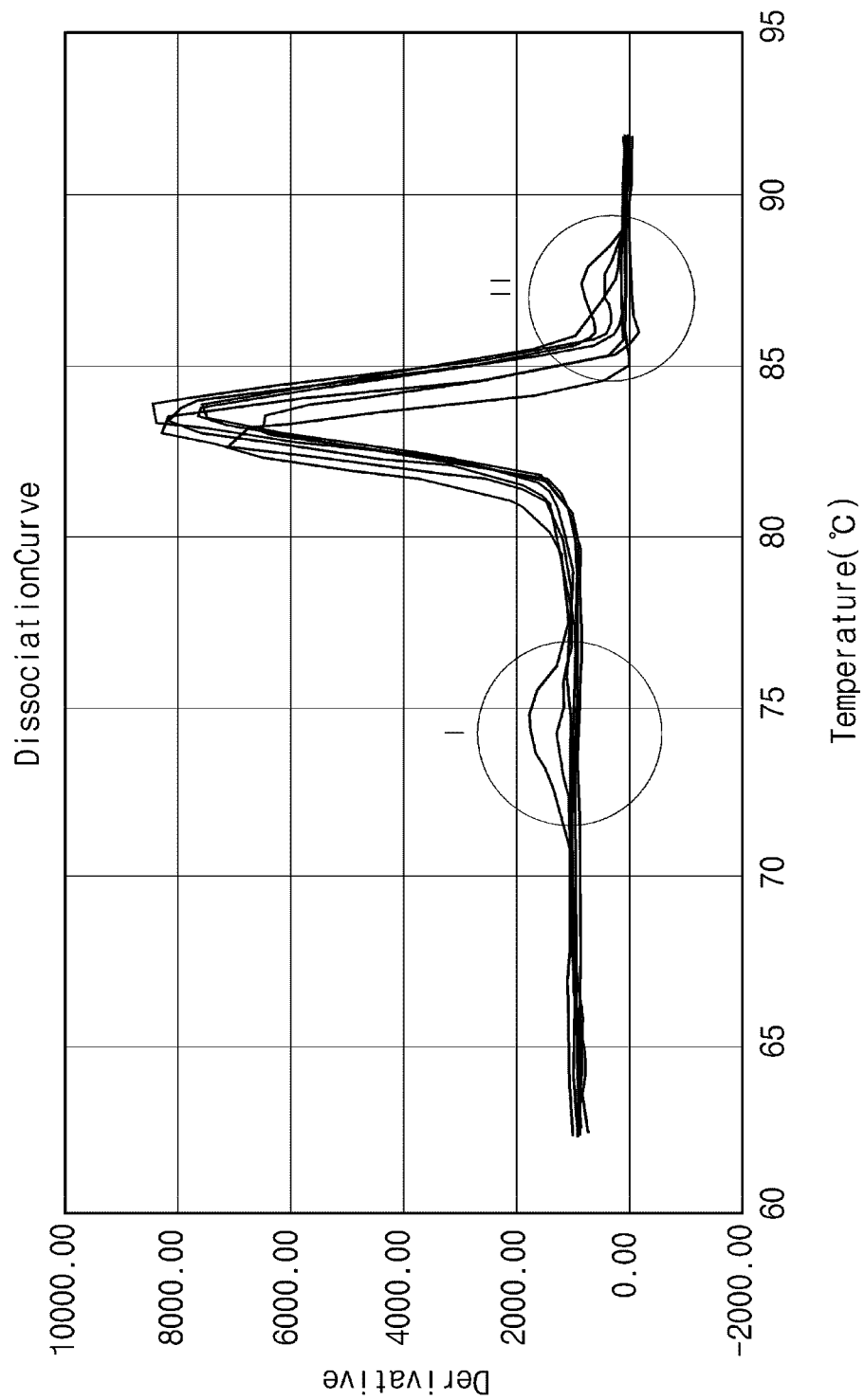
FIG. 19 is a graph illustrating the melting curve made by using the fluorescence graph of FIG. 17. In this graph, the horizontal axis are the temperature changes and the axis of ordinates indicates the fluorescence measured over the temperature rise.
Figure 20:
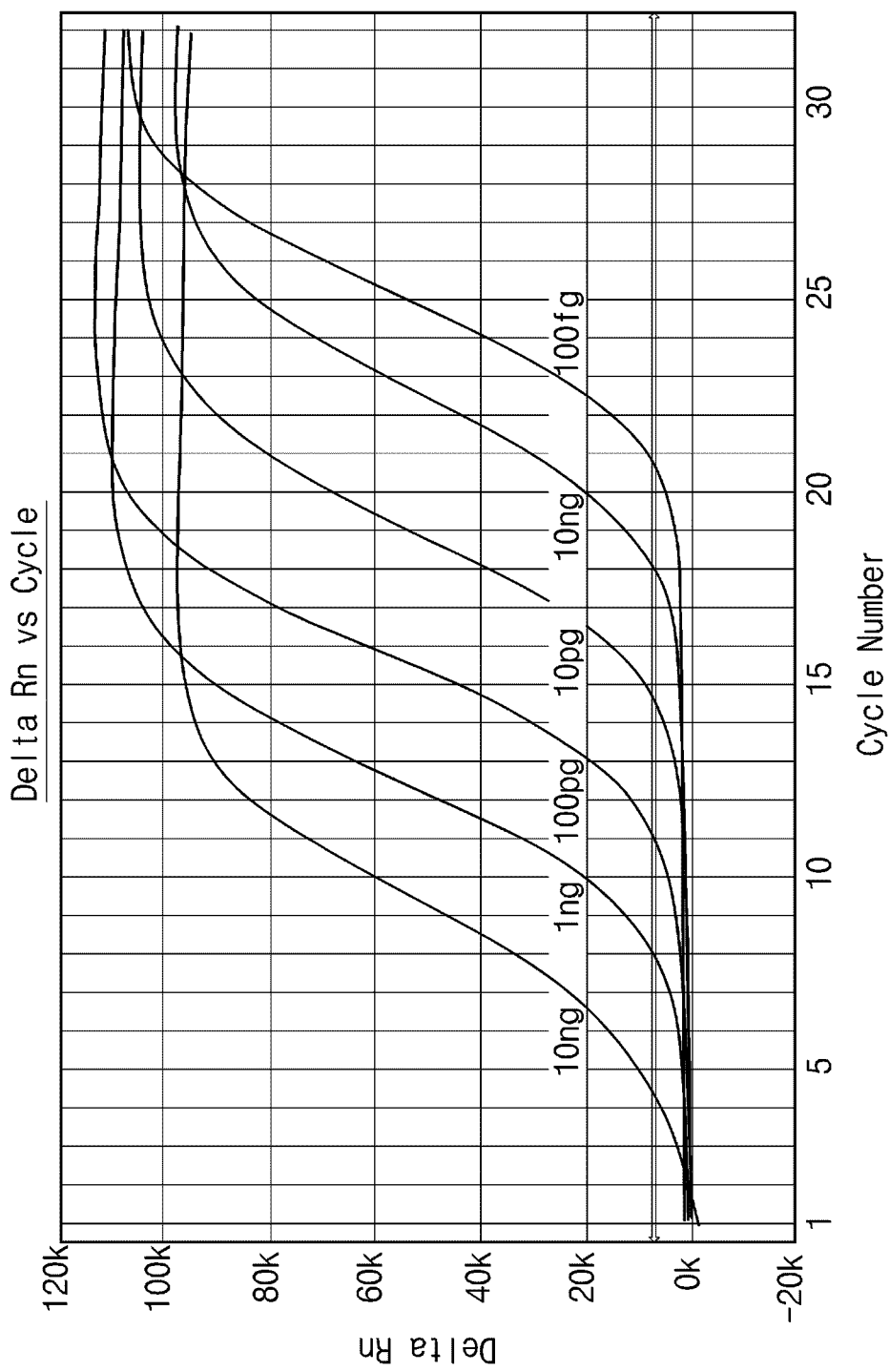
FIG. 20 is a graph illustrating the result of real-time quantitative PCR with the premix solution containing Taq DNA polymerase, a fluorescent material (Greenstar™), 2.0 mM PPi and 80 mU PPase. In this graph, the horizontal axis and the axis of ordinates are the same as described in FIG. 14.
Figure 21:
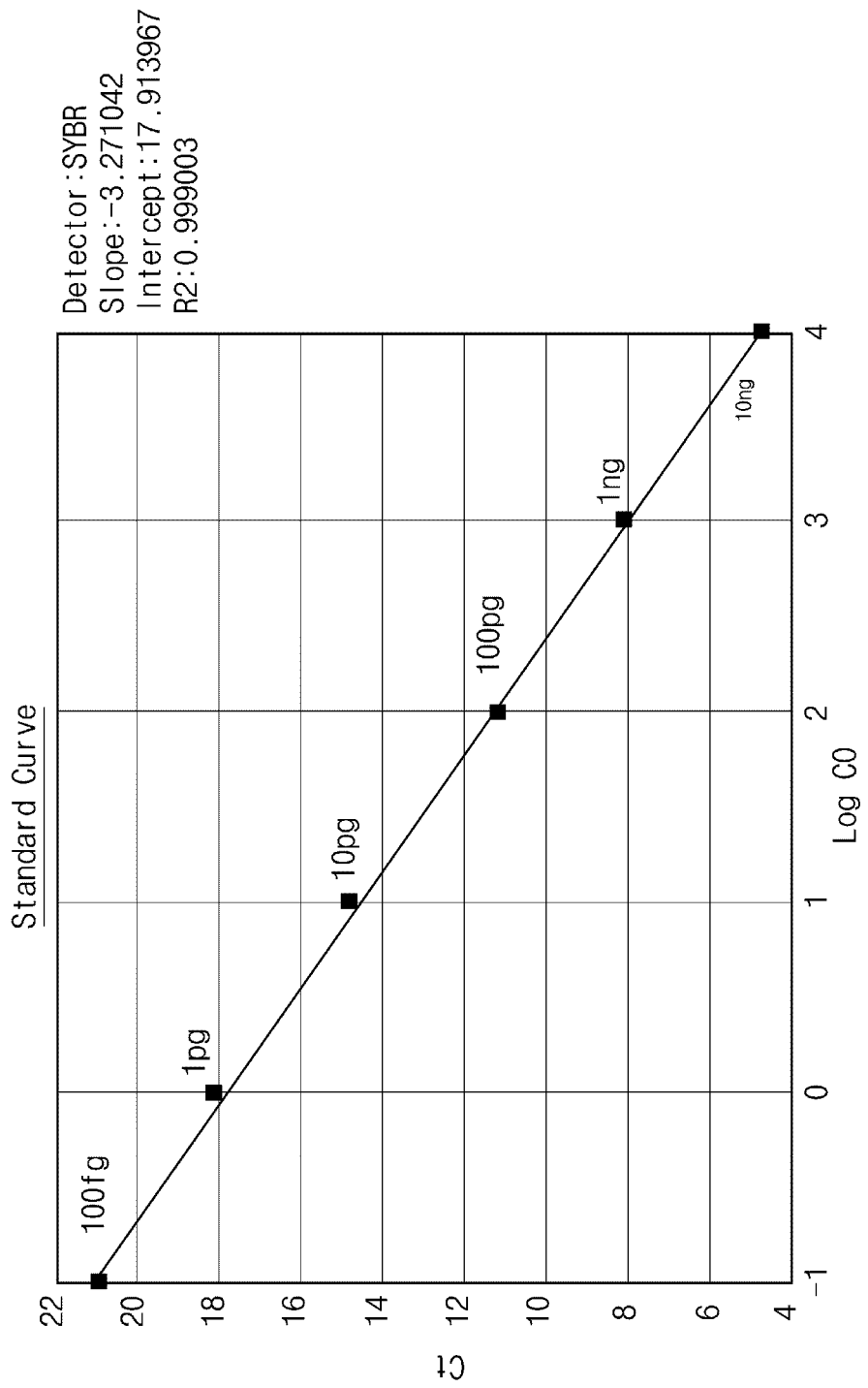
FIG. 21 is a graph illustrating the linearity of the quantitative curve made by using fluorescence curve according to the concentrations diluted stepwise in FIG. 20. In this graph, the horizontal axis and the axis of ordinates indicate the same as described in FIG. 15. According to the quantitative curve, efficiency of PCR was 100% and linearity of PCR was 0.9999.

As shown in FIG. 19, when composition 2 was used, three fluorescent peaks were observed. One was the peak observed at the melting temperature (Tm) of 82.8° C. which indicates the target product, another peak was observed at the melting temperature (Tm) of 75° C. which indicates primer dimmer (FIG. 19, "I") and the last one was observed at the melting temperature (Tm) of 87.5° C. which indicates the non-specific amplification product (FIG. 19, "II") that was bigger than the target product. Compared with the results in FIG. 16, the size of the peak presented by "II" was rather reduced, indicating the hot-start effect. But, primer dimer and the non-specific amplification product were still generated. The results of real-time quantitative PCR shown in FIG. 17 and FIG. 18 indicate that the non-specific amplification product and primer dimer were also generated. Therefore, these results could not be considered as precise quantitative PCR results (FIGS. 20 and 21).

Figure 22:
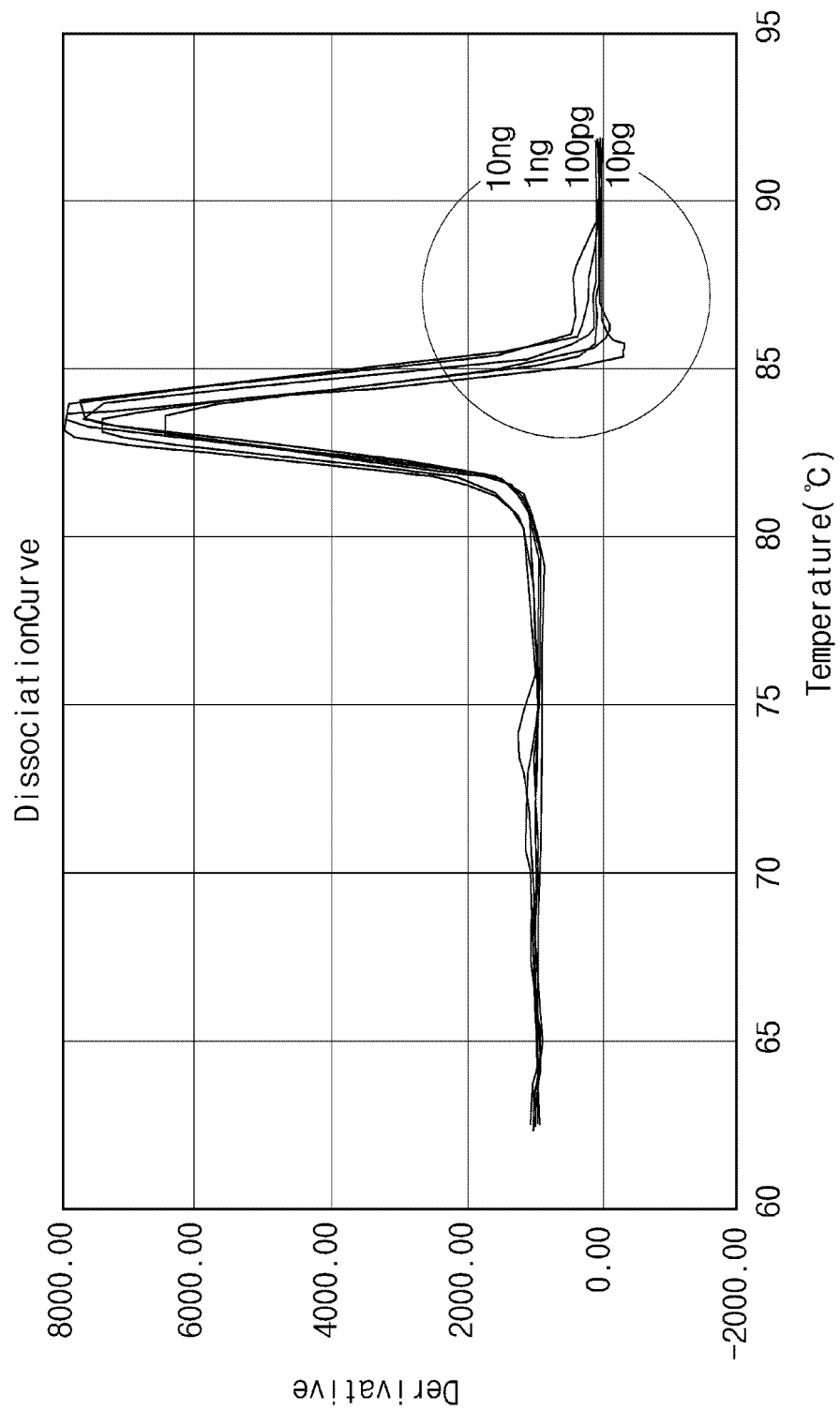
FIG. 22 is a graph illustrating the melting curve made by using the fluorescence graph of FIG. 20. In this graph, the horizontal axis indicates the temperature changes and the axis of ordinates indicates the fluorescence measured over the temperature rise.

As shown in FIG. 22, only one fluorescent peak was observed at the melting temperature of 82.8° C. when composition 1 was used, suggesting that the exact target product was generated. In the melting curve, the concentrations of lambda DNA were 10 ng, 1 ng, 100 pg and 10 pg serially from the top to the bottom. FIG. 20 and FIG. 21 illustrate the results of real-time quantitative PCR indicating the specific reaction products which mean the exact targets were amplified. That is, the hot-start effect by PPi and PPase was also observed in real-time qPCR. Compared with the composition 2 containing PPi and PPase (Korean Patent Application No: 10-1999-0004361), the composition 1 did not produce primer dimer and minimized the production of a non-specific amplification product.

Figure 23:
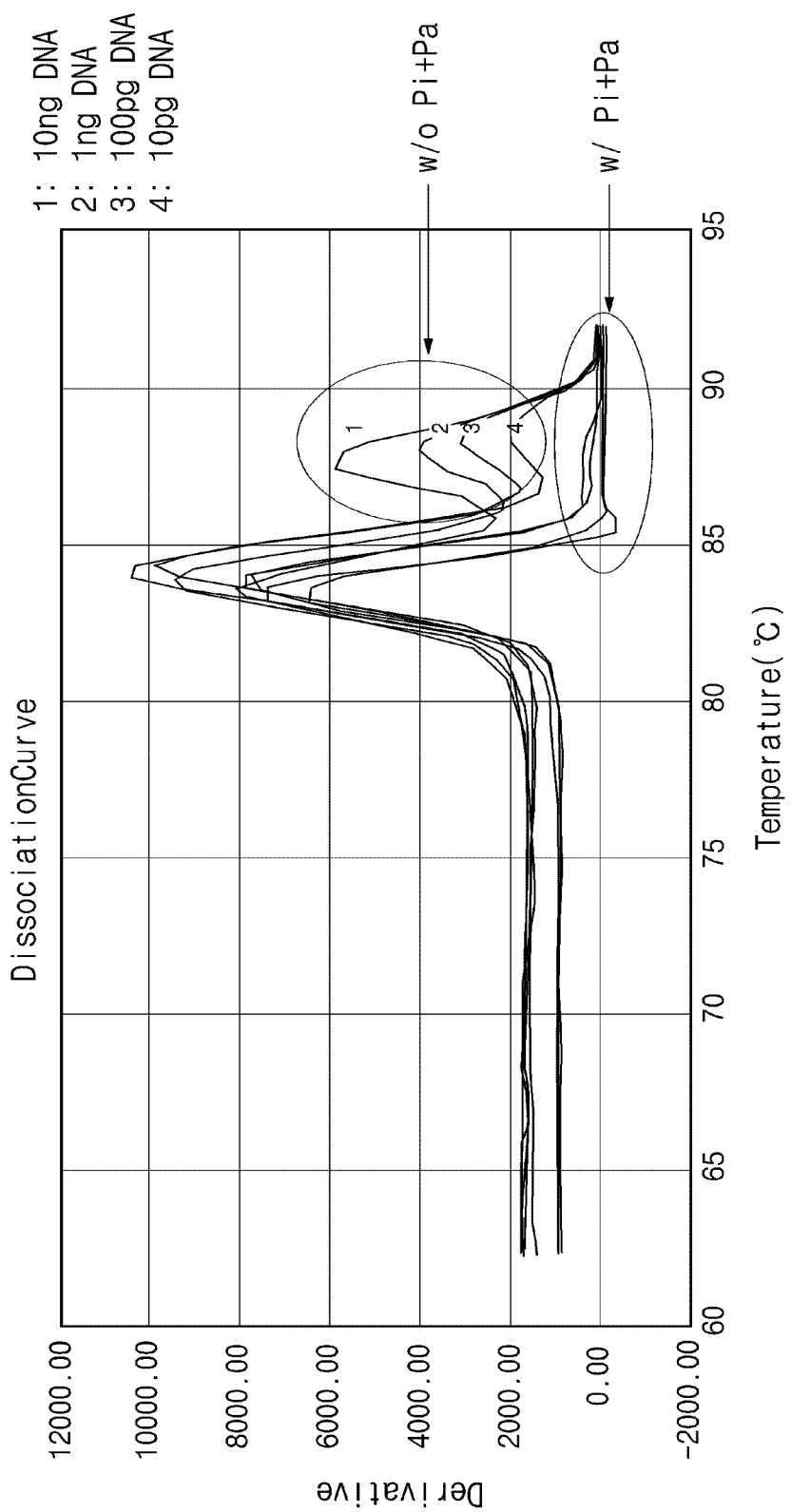
FIG. 23 is a graph illustrating the comparison by overlapping the melting curve of FIG. 16 over the melting curve of FIG. 22.

FIG. 23 is a graph illustrating the comparison by overlapping the melting curve of FIG. 16 over the melting curve of FIG. 22. The horizontal axis indicates the temperature changes and the axis of ordinates presents fluorescence measured over the temperature rise. w/o (without) PPi+PPase indicates the melting curve resulted from real-time quantitative PCR using 2×PCR Premix solution. In this graph, lines 1-4 indicate fluorescent peaks demonstrating the non-specific amplification products at the concentrations of 10 ng, 1 ng, 100 pg and 10 pg stepwise. w/(with) PPi+PPase indicates the melting curve resulted from real-time quantitative PCR using 2×PCR Premix solution containing 2.0 mM PPi and 80 mU PPase per 20 μl reaction, suggesting that a non-specific amplification product was not generated.

Example 9

PCR Using the Dried Premix Containing Top DNA Polymerase, PPi and PPase

PCR was performed using human DNA as a template with the dried premix containing Top DNA polymerase, PPi and PPase in order to amplify products in diverse lengths. To do so, 1) the dried composition of the premix containing Top DNA polymerase, PPi and PPase (SibEnzyme Ltd.) (comprising 10 mM Tris-HCl pH 9.0, 40 mM KCl, 1.5 mM $MgCl_2$, 4 dNTPs (250 μM each), 1 U Top DNA polymerase, 0.01% Tween 20, 2.0 mM PPi, 80 mU PPase and a stabilizer) and 2) the dried composition of the premix containing Top DNA polymerase (comprising 10 mM Tris-HCl pH 9.0, 40 mM KCl, 1.5 mM $MgCl_2$, 4 dNTPs (250 μM each), 1 U Top DNA polymerase, 0.01% Tween 20, and a stabilizer) were prepared.

10 ng of human DNA was used as a template DNA. To amplify 139 bp product, the primer set composed of the forward primer represented by SEQ. ID. NO: 22 and the reverse primer represented by SEQ. ID. NO: 23 was used (lanes 1 and 8, FIG. 24). To amplify 211 bp product, the primer set composed of the forward primer represented by SEQ. ID. NO: 4 and the reverse primer represented by SEQ. ID. NO: 3 was used (lanes 2 and 9, FIG. 24). To amplify 447 bp product, the primer set composed of the forward primer represented by SEQ. ID. NO: 4 and the reverse primer represented by SEQ. ID. NO: 5 was used (lanes 3 and 10, FIG. 24). To amplify 618 bp product, the primer set composed of the forward primer represented by SEQ. ID. NO: 22 and the reverse primer represented by SEQ. ID. NO: 21 was used (lanes 4 and 11, FIG. 24). To amplify 1.082 bp product, the primer set composed of the forward primer represented by SEQ. ID. NO: 4 and the reverse primer represented by SEQ. ID. NO: 23 was used (lanes 5 and 12, FIG. 24). To amplify 1,296 bp product, the primer set composed of the forward primer represented by SEQ. ID. NO: 20 and the reverse primer represented by SEQ. ID. NO: 21 was used (lanes 6 and 13, FIG. 24). To amplify 1,561 bp product, the primer set composed of the forward primer represented by SEQ. ID. NO: 4 and the reverse primer represented by SEQ. ID. NO: 21 was used (lanes 7 and 14, FIG. 24).

The reaction mixture was left at 37° C. for 4 hours before PCR. PCR was then performed as follows: predenaturation at 94° C. for 5 minutes, denaturation at 94° C. for 20 seconds, annealing at 55° C. for 40 seconds, extension at 72° C. for 40 seconds, 33 cycles from denaturation to extension, and final extension at 72° C. for 5 minutes. The result of PCR was confirmed by electrophoresis using 0.5×TBE buffer containing 1.6% agarose.

Figure 24:
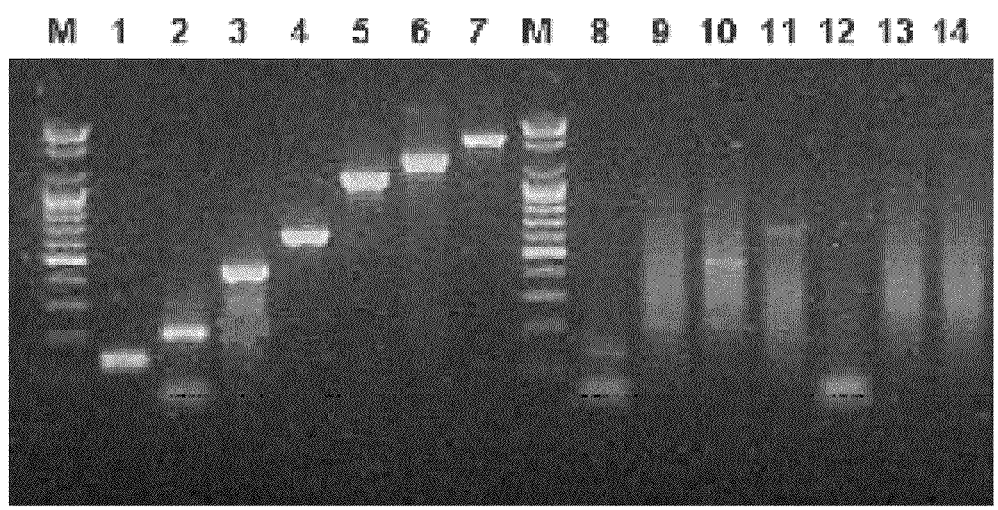
FIG. 24 is a photograph of agarose gel electrophoresis illustrating the result of Long kb PCR using human DNA with the premix containing PPi, PPase, and Top DNA polymerase and with the premix containing Top DNA polymerase only. Lane 1-lane 7 illustrate the results of Long kb PCR using the premix containing PPi, PPase and Top DNA polymerase and lane 8-lane 16 illustrate the results of Long kb PCR using the premix containing Top DNA polymerase only.
Figure 25:
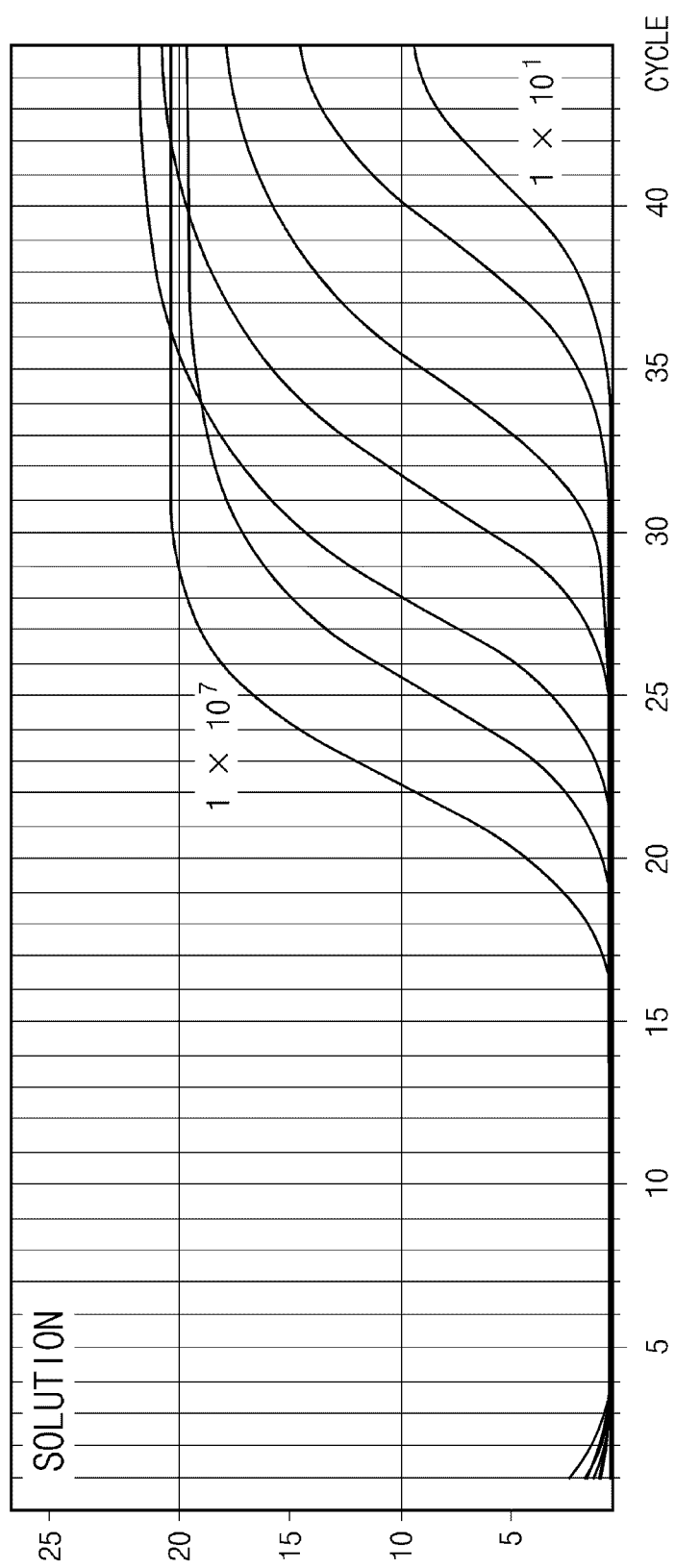
FIG. 25-FIG. 31 are graphs illustrating the results of real-time PCR with samples obtained from the dried premix composition of the present invention stored at 50° C. every 1-2 days until the 9$^{th}$ day from preparation. For the control group, a solution having the same composition as the dried premix for the experimental group was prepared prior to the experiment.
Figure 26:
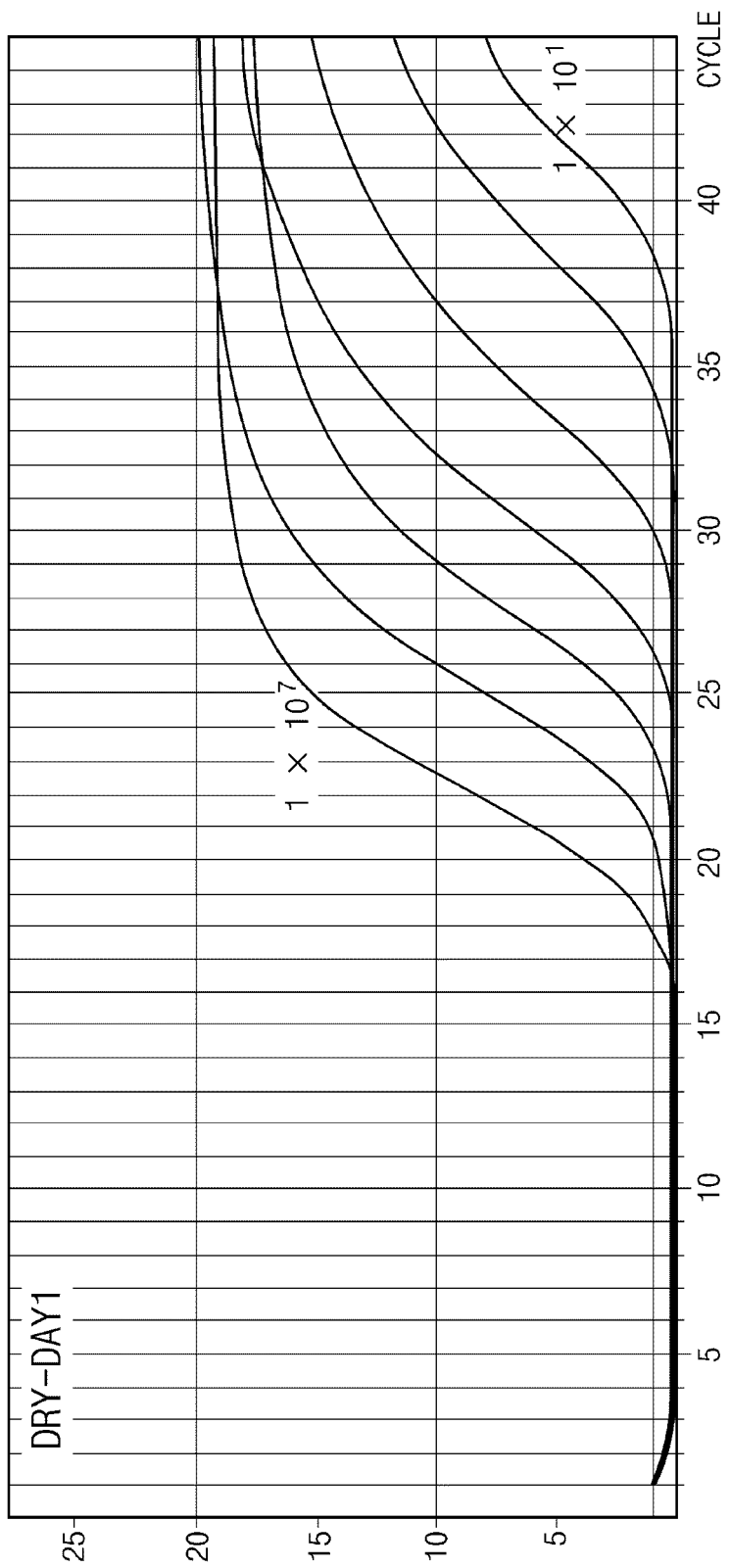
Figure 27:
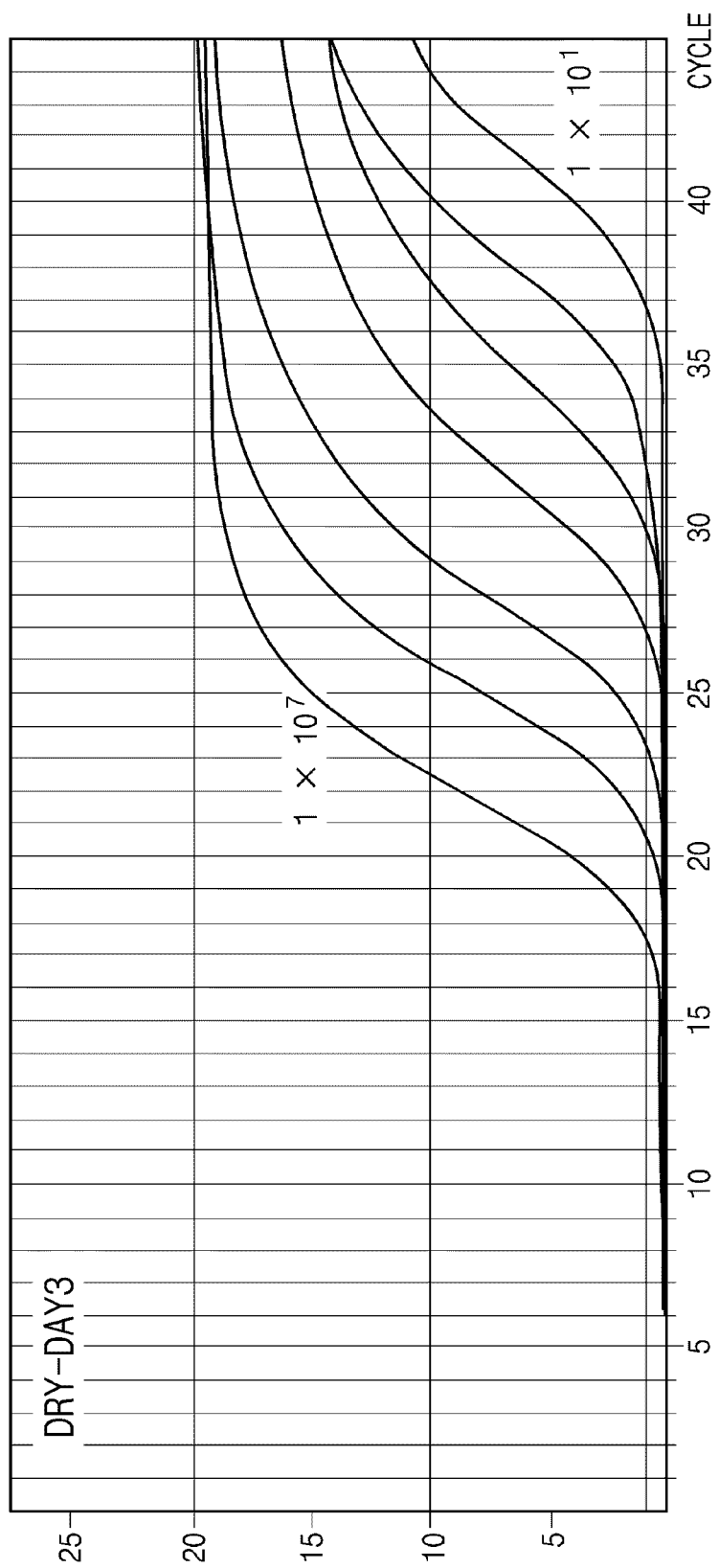
Figure 28:
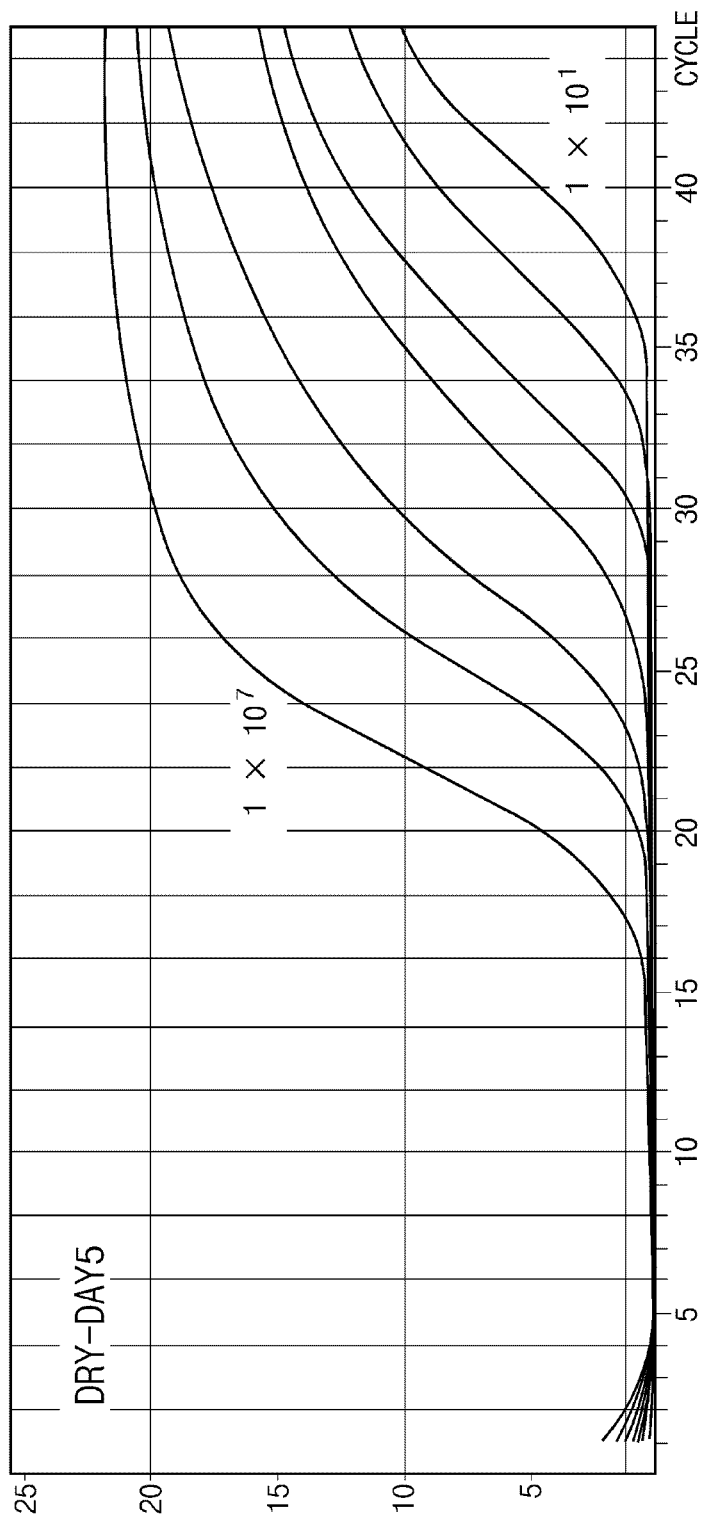
Figure 29:
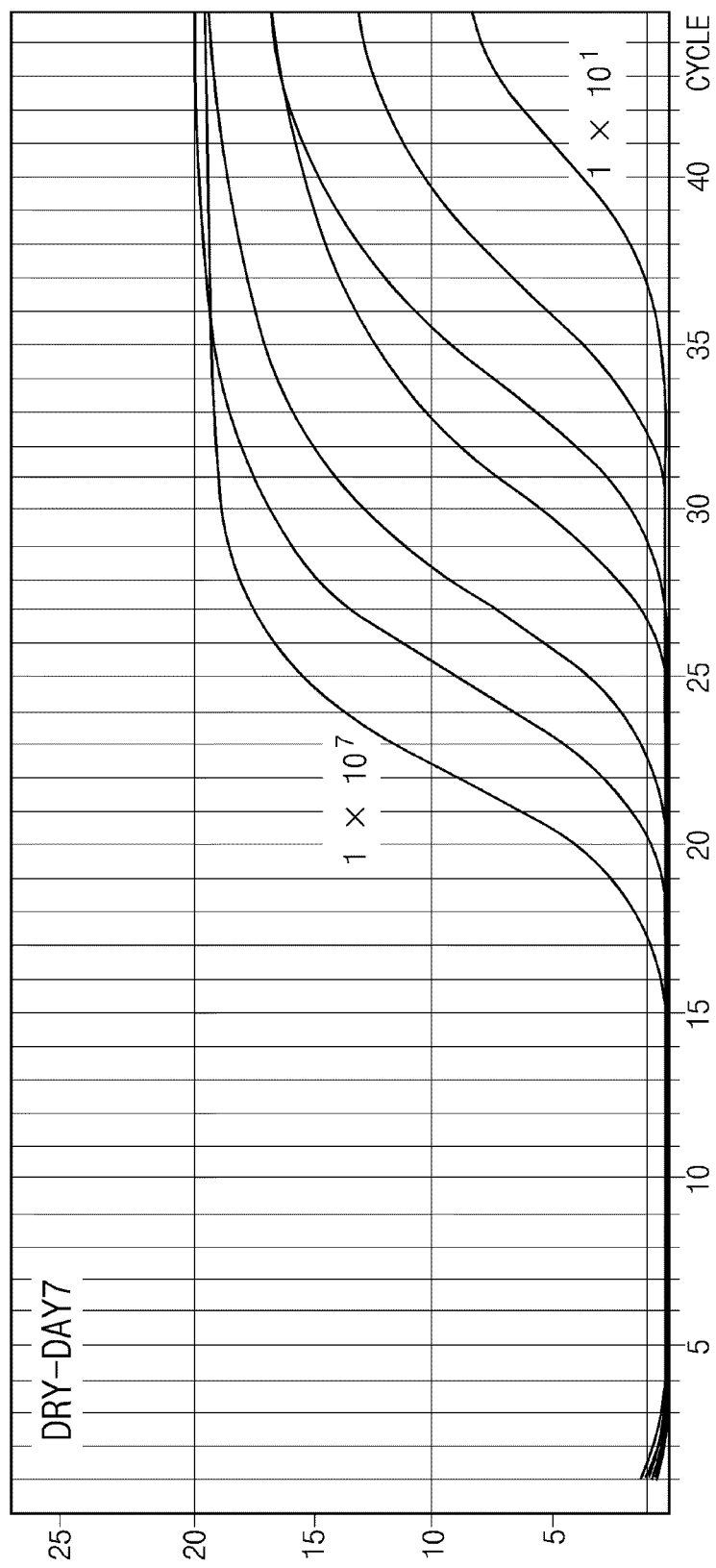
Figure 30:
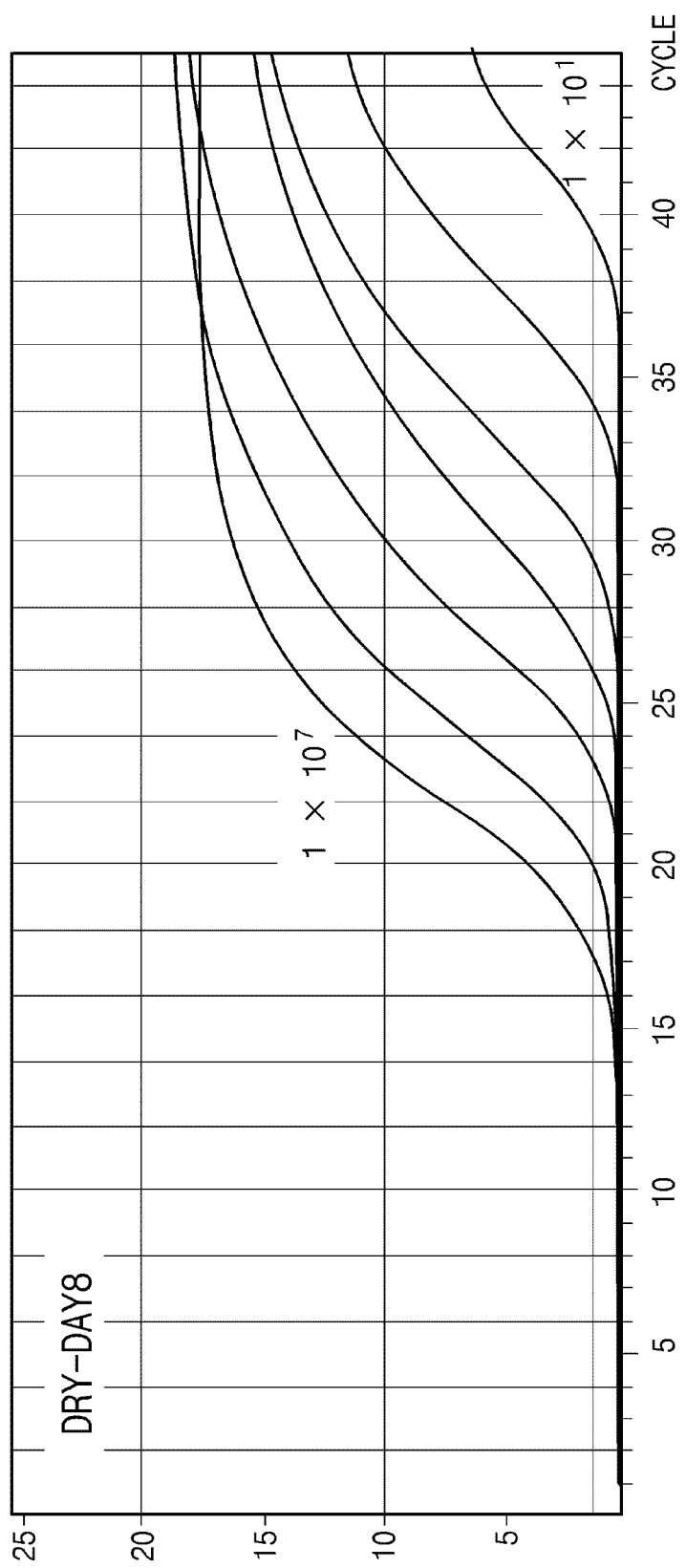
Figure 31:
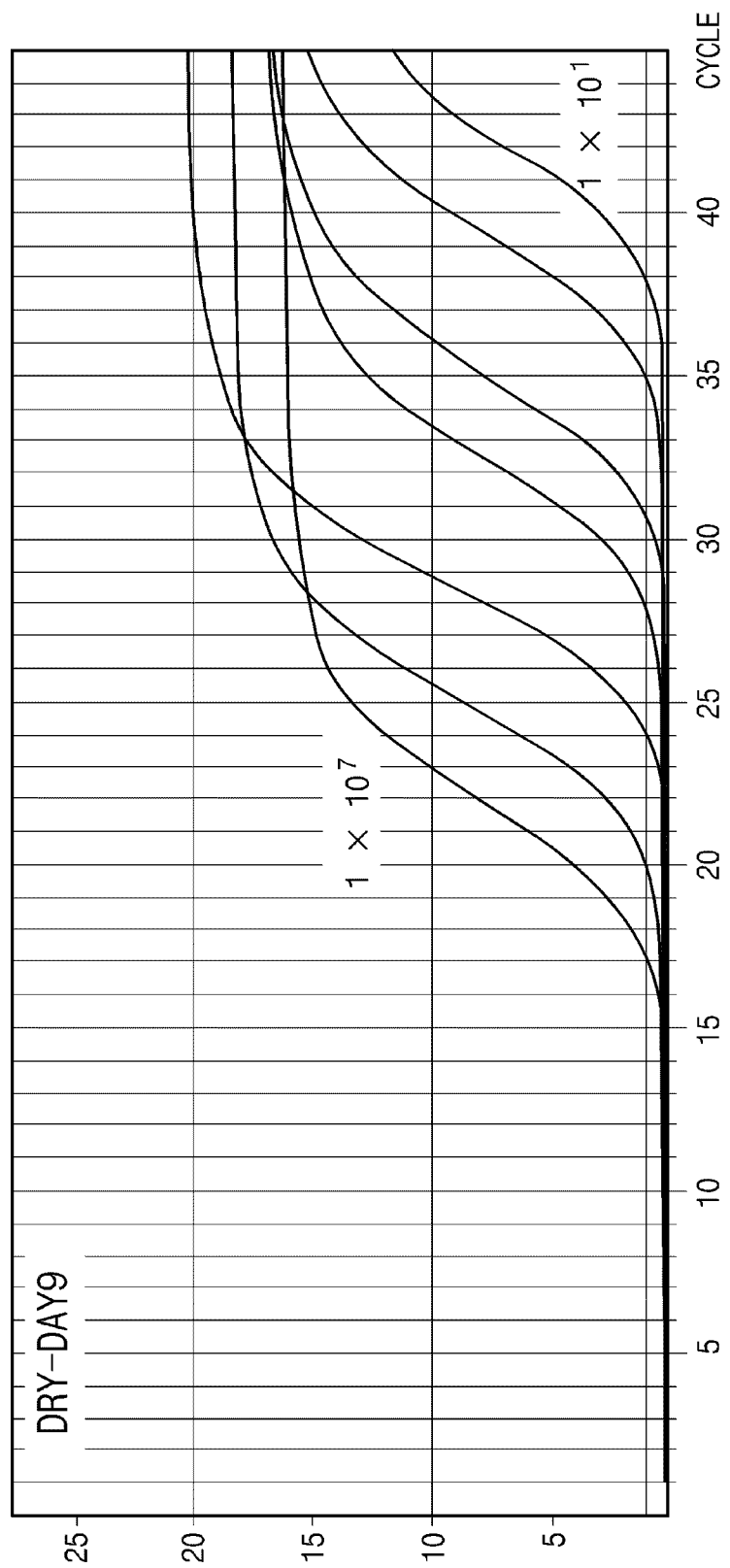
Figure 32:
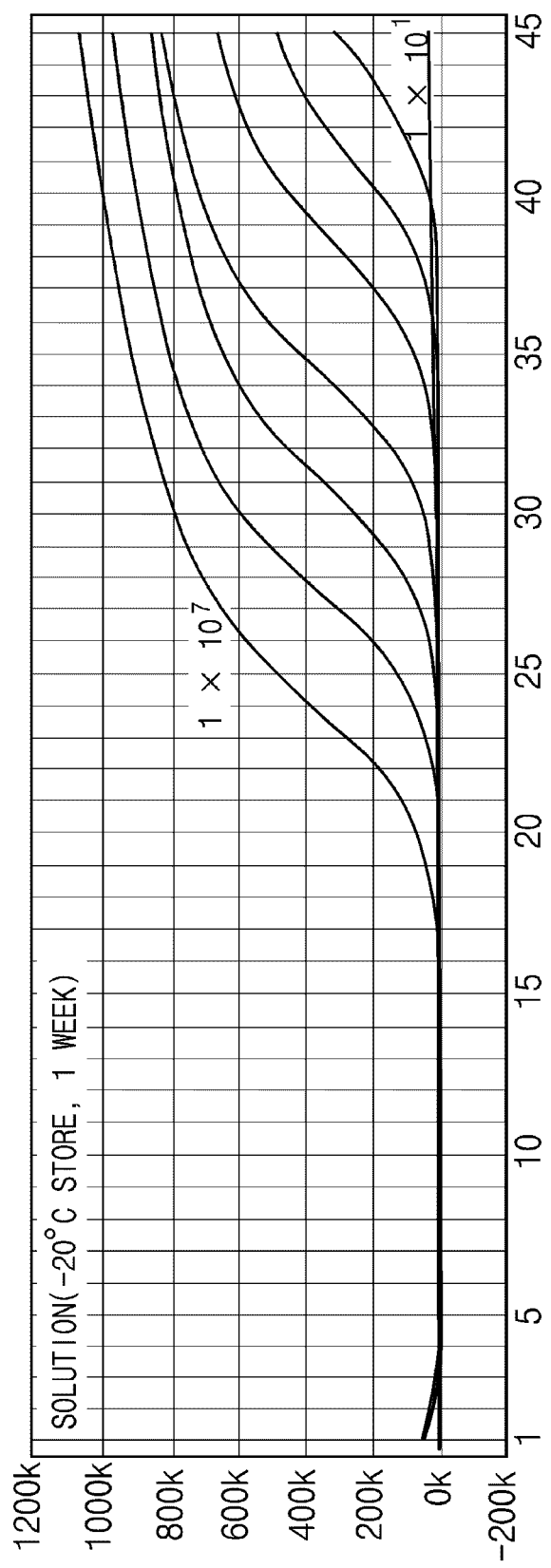
FIG. 32-FIG. 40 are graphs illustrating the results of real-time PCR with samples obtained from the dried premix composition of the present invention stored at 4° C. or at −20° C. every week until the 7$^{th}$ week from preparation. For the control group, a solution having the same composition as the dried premix of the present invention was used.
Figure 33:
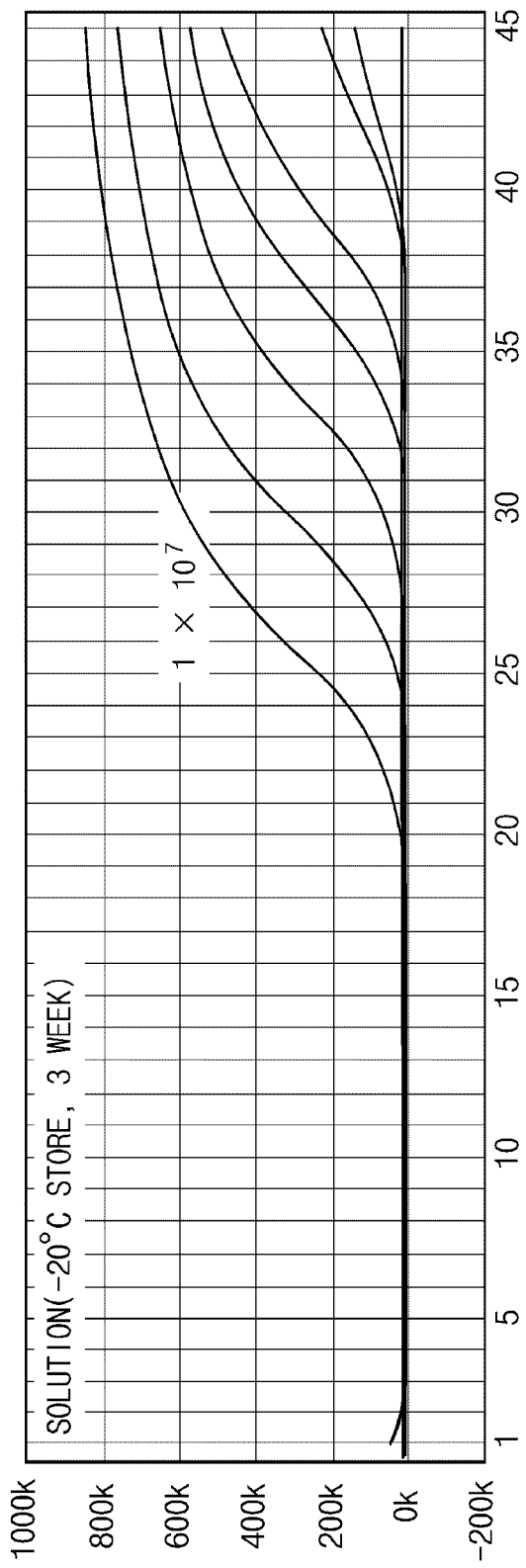
Figure 34:
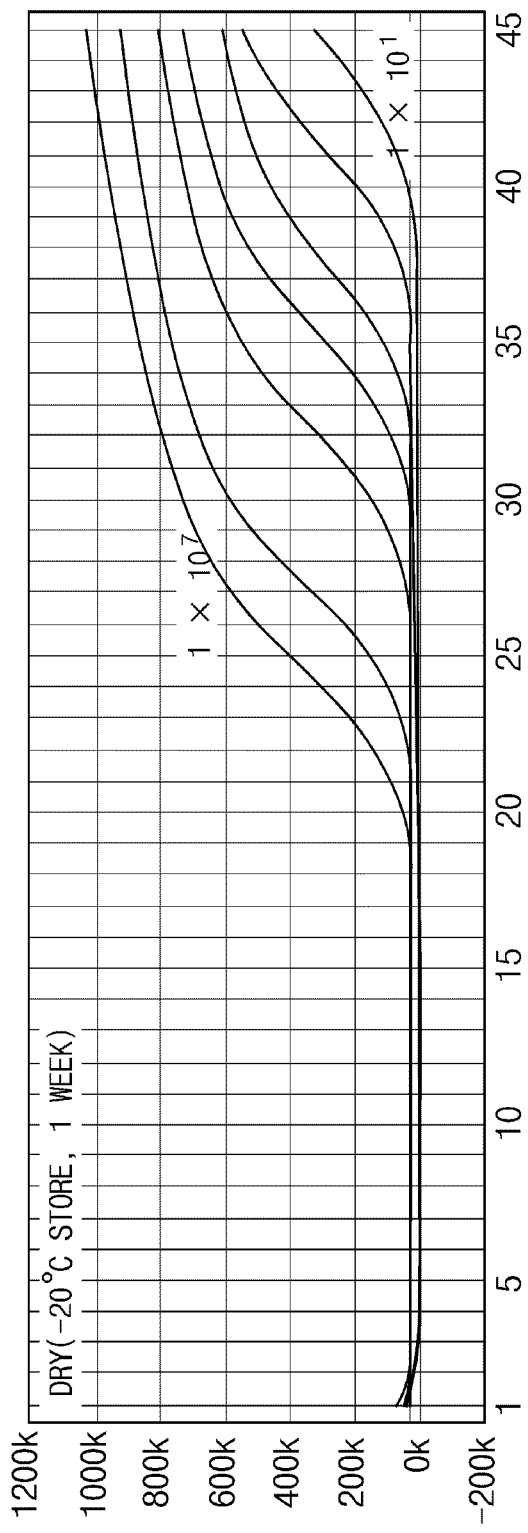
Figure 35:
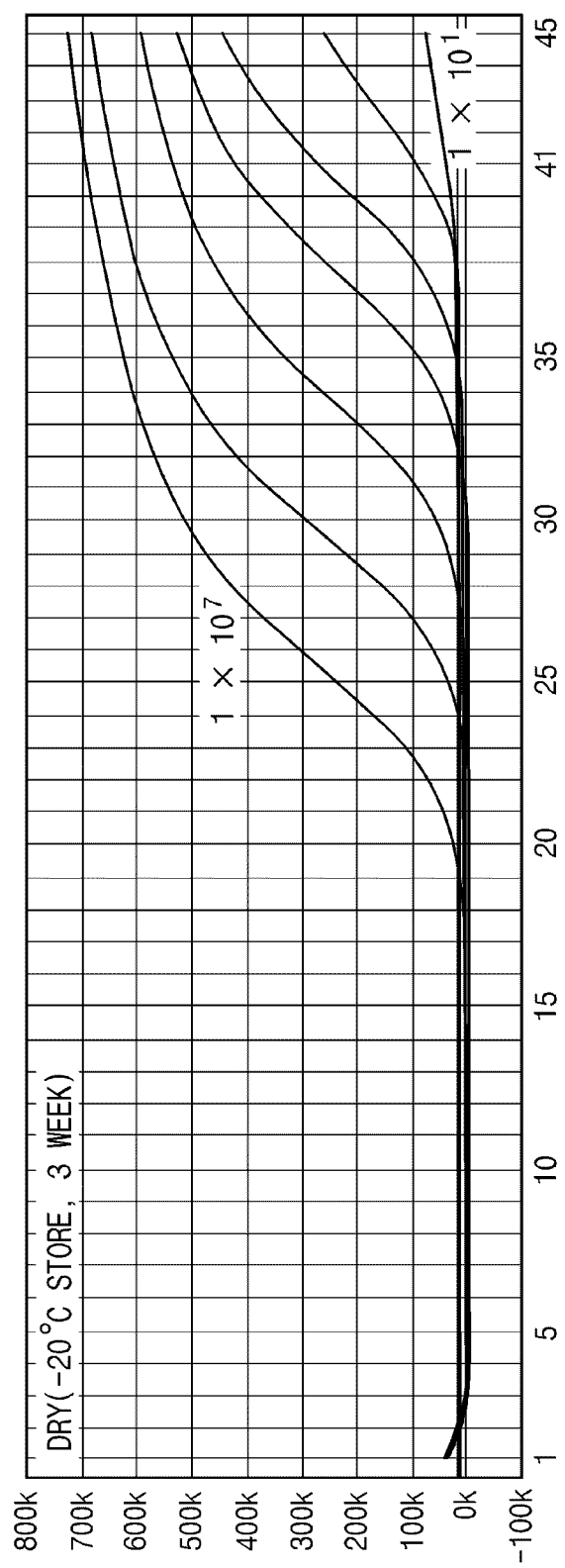
Figure 36:
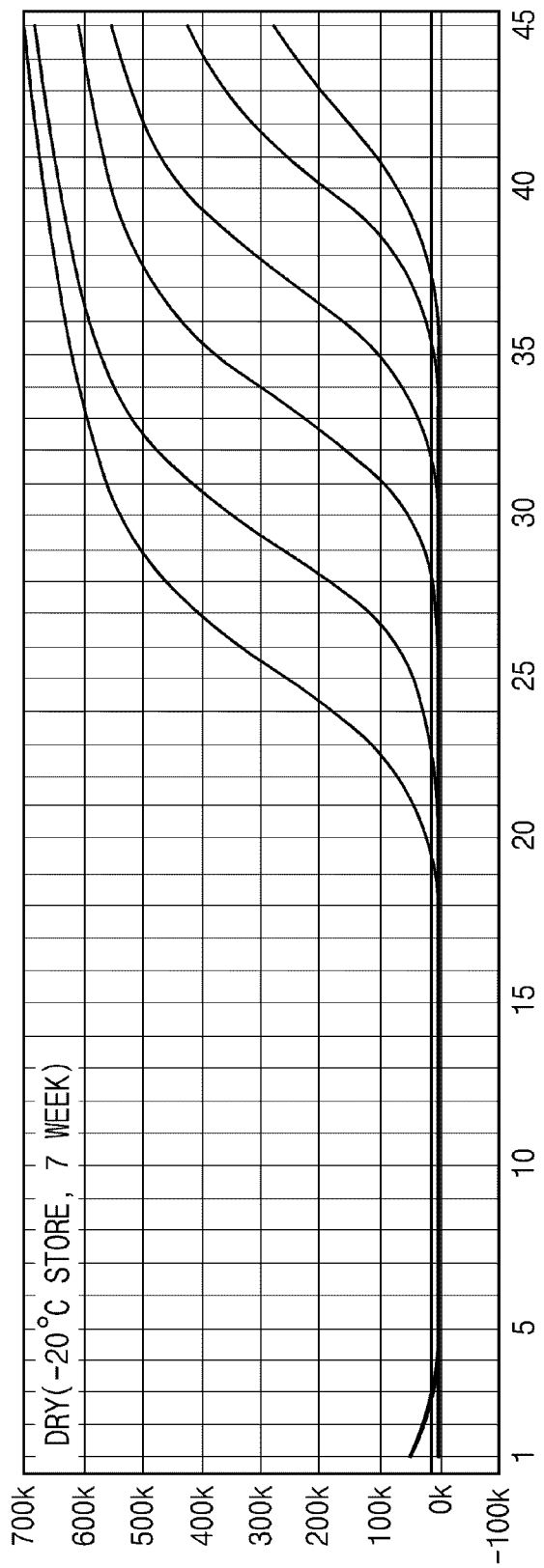

As a result, when the premix containing 2.0 mM PPi, 80 mU PPase and Top DNA polymerase was used, PCR reactivity and specificity was excellent under each of the experimental conditions to amplify 100 bp-1.6 kbp DNA even after pre-treatment for 4 hours (lanes 1-7, FIG. 24). On the other hand, when the premix containing Top DNA polymerase was used alone, a non-specific reaction was detected or reaction itself was not successful under each of the conditions to amplify 100 bp-1.6 kbp DNA (lanes 8-14, FIG. 24). From the above results, significant inhibition of a non-specific reaction and high PCR reactivity, the hot-start effect, were confirmed when the premix containing Top DNA polymerase, PPi and PPase was used.

Example 10

Storage Stability of the Dried Hot-Start Premix Composition Containing PPi and PPase To investigate storage stability of the hot-start premix composition containing PPi and PPase (Bioneer corporation, republic of Korea), the dried premix comprising 10 mM Tris-HCl pH 9.2, 60 mM KCl, 1.5 mM $MgCl_2$, 4 dNTPs (250 μM each), 1 U wTfi DNA polymerase, 0.01% Tween 20, 2.0 mM PPi, 92.5 mU PPase, 1.2 μg BSA and a stabilizer (Methyl-α-D-Gluco-Pyranoside: α-MG) was prepared. For the control, the solution having the same composition as the above was prepared prior to use. Drying was performed in SuperCentra (Bioneer corporation, republic of Korea) in which the temperature outside of the device was set at 40° C. and the temperature inside of the device was set at 36° C., for 50 minutes. The prepared premix was stored in a 50° C. reactor. From day 0 to day 7, 8 well strip containing the premix was taken every day. The strip was stored in a deep-freezer until real-time PCR or used for real-time PCR on the day of sampling under the same conditions as provided for the control.

Primer, probe and standard template DNA for real-time PCR were as follows. As a template DNA, plasmid DNA containing the sequence of Varicella-zoster virus ORF gene was used. The template DNA having the copy number of $1\times10^0 \sim 1\times10^6$ copy/µl was added to each well by 10 µl. DEPC treated distilled water was used for the control by the same volume as the template DNA. The primer set composed of the forward primer represented by SEQ. ID. NO: 25 (5'-TGGAT-GTGGTGTTCCCAAT-3') and the reverse primer represented by SEQ. ID. NO: 26 (5'-GTTCAGGCAAC-CGTTTTGA-3') generating 80 bp PCR product was used. As a probe, TaqMan based probe represented by SEQ. ID. NO: 27 (5'-CTCATACCGAGTTGCATCCAACG-3') in which FAM was labeled at 5' end and TAMRA was labeled at 3' end was used. The primers represented by SEQ. ID. NO: 25 and NO: 26 were added at the concentration of 10 pmol per 50 µl reaction. The probe represented by SEQ. ID. NO: 27 was added at the concentration of 7.5 pmol per 50 µl reaction. DEPC treated distilled water was added to each well to make the total reaction solution 50 µl. The solution having the same composition as that of the dried premix was used for the control to compare the reactivity during drying and storage, which was prepared prior to use. Real-time PCR was performed under the same conditions as given for the real-time PCR with the dried premix.

Exicycler version 3.0 (Bioneer corporation, republic of Korea) was used for real-time PCR. The operation program and analysis program were executed according to the manufacturer's instructions. Real-time PCR was performed as follow: predenaturation at 95° C. for 5 minutes, denaturation at 95° C. for 20 seconds, annealing/extension at 55° C. for 40 seconds, and detection of fluorescence (45 cycles). Upon completion of the PCR, the PCR product was examined by the analysis program operating in the Excicycler real-time PCR device.

As a result, the reactivity of the dried premix stored for 8 days at 50° C. was similar to that of the primary dried premix. The Rn value subsequent to drying was compared with those of until 9 days at 50° C. As a result, 85% of fluorescence was maintained (FIGS. 25-31). The result of 50° C. experiment was re-calculated to investigate reactivity under −20° C. storage. As a result, the dried premix was expected to retain its reactivity similar to that of the control until 1,152 days (3.1 year) (Lee sangyong, Reliability engineering, 1999, Hyungseul Publishing Company).

Example 11

Comparison of Stability During Cold Storage and Freezing Storage Between the Dried Hot-Start Premix Containing PPi and PPase and the Hot-Start Solution having the Same Composition as the Premix To compare the stability during cold storage (4° C.) and freezing storage (−20° C.) between the dried hot-start premix containing PPi and PPase (Bioneer corporation, republic of Korea) and the hot-start solution having the same composition as the above premix, the dried premix was prepared in the same manner as described in Example 10. The prepared premix was stored in a refrigerator (4° C.) or a deep-freezer (−20° C.). A Strip was taken every week for 7 week storage. The strip was stored in a deep-freezer until real-time PCR or used for real-time PCR on the day of sampling under the same conditions as provided for the control. For the control, the hot-start solution having the same composition as the above was prepared prior to use.

Primer, probe and standard template DNA for real-time PCR were as follows. As a template DNA, plasmid DNA containing the sequence of HBV surface antigen gene (large surface gene) was used. The template DNA having the copy number of $1\times10^0 \sim 1\times10^6$ copy/µl was added to each well by 10 µl. The primer set composed of the forward primer represented by SEQ. ID. NO: 28 (5'-CCAATCACTCACCAAC-CTCTTGT-3') and the reverse primer represented by SEQ. ID. NO: 29 (5'-AGCAGGATGAAGAGGAATATGATAAA-3') generating 91 bp PCR product was used. As a probe, TaqMan based probe represented by SEQ. ID. NO: 30 (5'-TCCTGGCTATCGCTGGATGTGTCTGC-3') in which FAM was labeled at 5' end and TAMRA was labeled at 3' end was used. Real-time PCR was performed in the same manner as described in Example 10.

7500 Fast system (Applied Biosystem) was used for real-time PCR. The operation program and analysis program were executed according to the manufacturer's instructions. Real-time PCR was performed as follow: predenaturation at 95° C. for 5 minutes, denaturation at 95° C. for 20 seconds, annealing/extension at 55° C. for 40 seconds, and detection of fluorescence (45 cycles).

Figure 37:
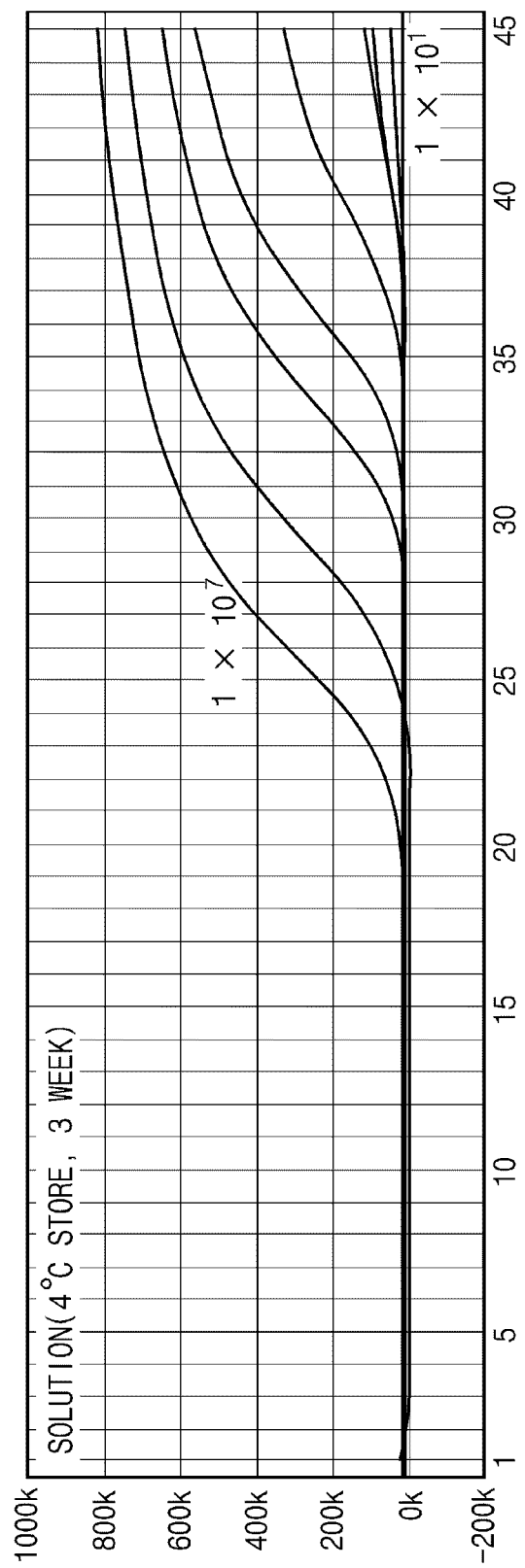
Figure 38:
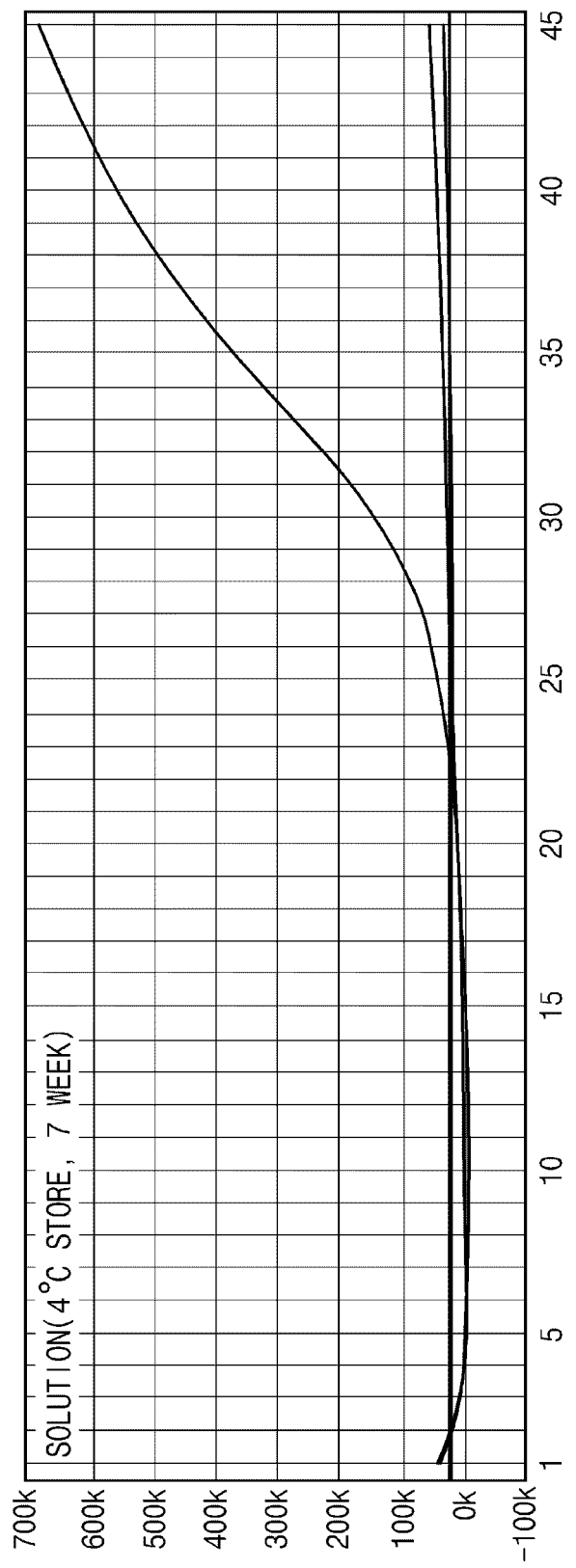
Figure 39:
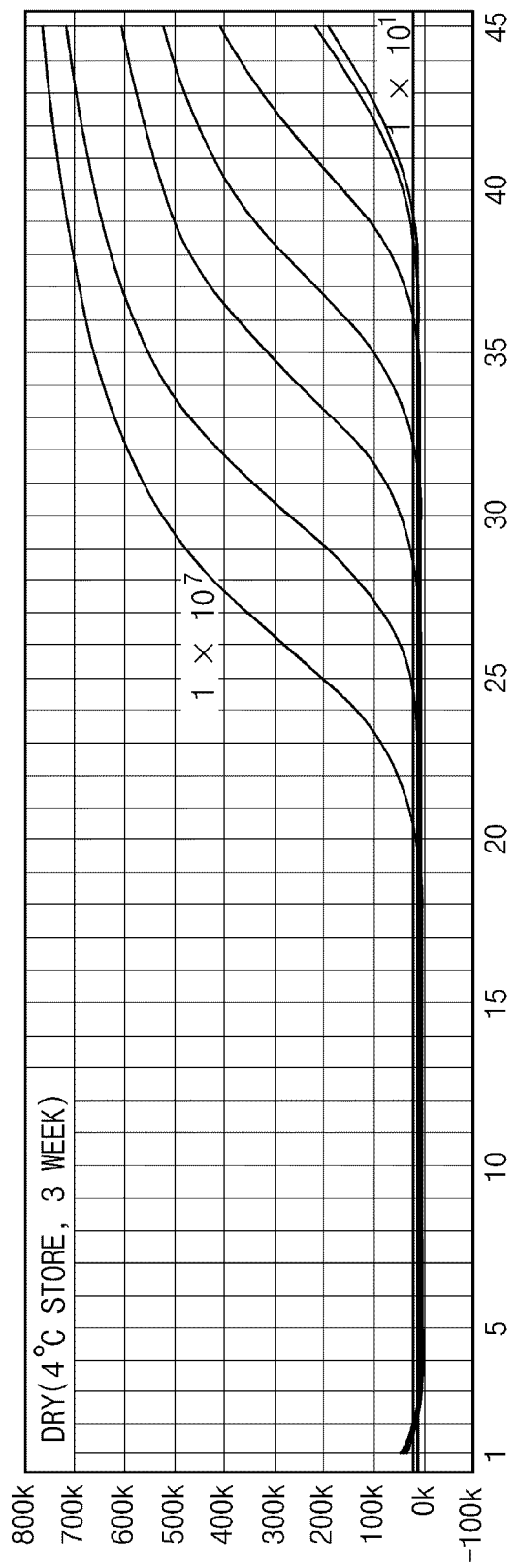
Figure 40:
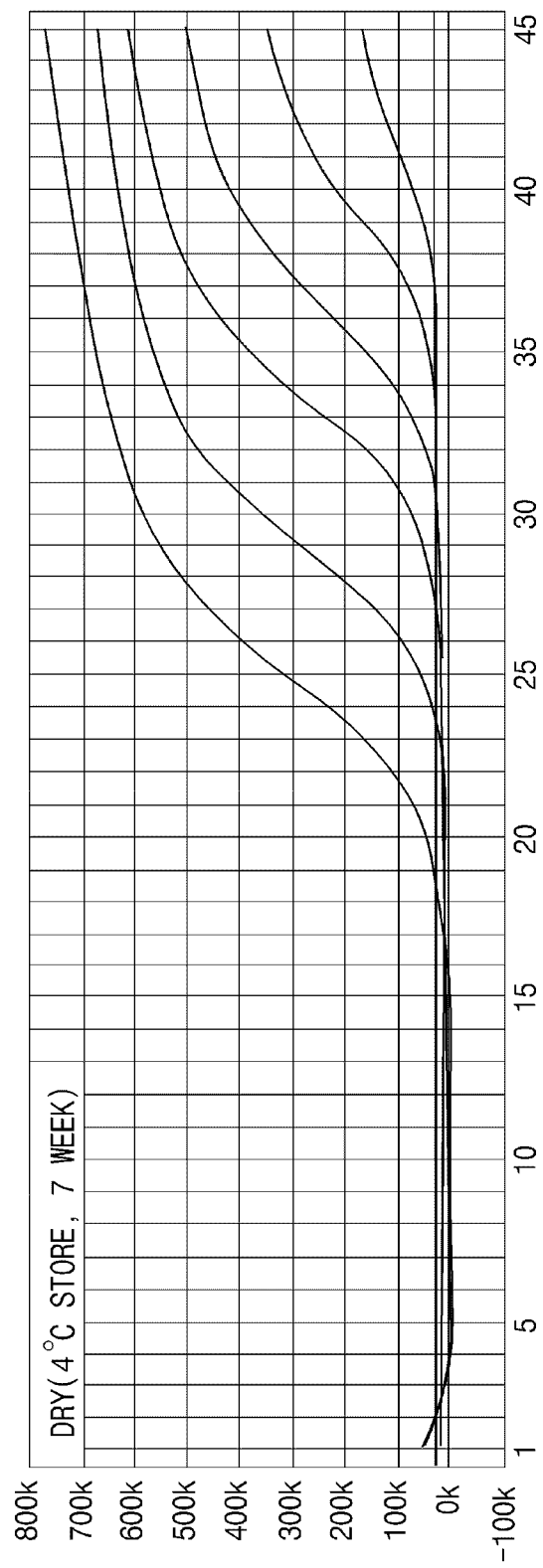

As a result, the dried hot-start premix of the present invention retained reactivity until 7 weeks of cold storage (4° C.) or freezing storage (−20° C.) (FIG. 32-FIG. 36, FIG. 39 and FIG. 40). In the meantime, the control hot-start solution having the same composition as the said premix demonstrated similar reactivity until 3 weeks of cold storage (4° C.) but lost reactivity after 7 week of cold storage (FIG. 37 and FIG. 38). The above results indicate that when the master mix is stored as a solution, reactivity is rapidly lost from the $3^{rd}$ week of cold storage (4° C.), but when it is prepared as a dried hot-start premix, reactivity can be maintained over a long period.

Example 12

PCR Reactivity of the Dried Premix Containing PPi and PPase and the Conventional Hot-Start Premix To compare reactivity between the dried hot-start premix containing PPi and PPase and the conventional hot-start premix, TaKaRa Premix Ex Taq™ (Takara, Cat#: RR039A), Qiagen QuantiFast™ Probe PCR+ROX Vial Kit (Qiagen, Cat#: 204352) and Invitrogen Platinum Quantitative PCR SuperMix-U (Invitrogen, Cat#: 11730-017) were selected for the comparative groups. PCR reactivity was compared between the dried hot-start premix of the present invention and the selected ones. Drying was performed in the same manner as described in Example 10 to prepare the dried hot-start premix containing PPi and PPase.

Primer, probe and standard template DNA for real-time PCR were as follows. As a template DNA, plasmid DNA containing the sequence of West Nile virus E gene was used. The template DNA having the copy number of $2\times10^0 \sim 2\times10^6$ copy/µl was added to each well by 5 µl. The primer set composed of the forward primer represented by SEQ. ID. NO: 31 (5'-GTGGAGGAACAGAGAGACGTTAA TG-3') and the reverse primer represented by SEQ. ID. NO: 32 (5'-TCCCTCTTGTGAGCCC AATG-3') generating 85 bp PCR product was used. As a probe, TaqMan based probe represented by SEQ. ID. NO: 33 (5'-TGAG GAACCACACGC-CACGAAGC-3') in which FAM was labeled at 5' end and TAMRA was labeled at 3' end was used. Real-time PCR was performed by the same manner as described in Example 10. The same primers, probes and standard template DNA samples were used for those three premix products from three different companies and at this time the conditions for real-time PCR and mastermix preparation were set according to the manufacturer's instructions.

7500 Fast system (Applied Biosystem) was used for real-time PCR. The operation program and analysis program were executed according to the manufacturer's instructions. Upon completion of the PCR, the PCR product was examined by the analysis program operating in the 7500 Fast system.

Figure 41:
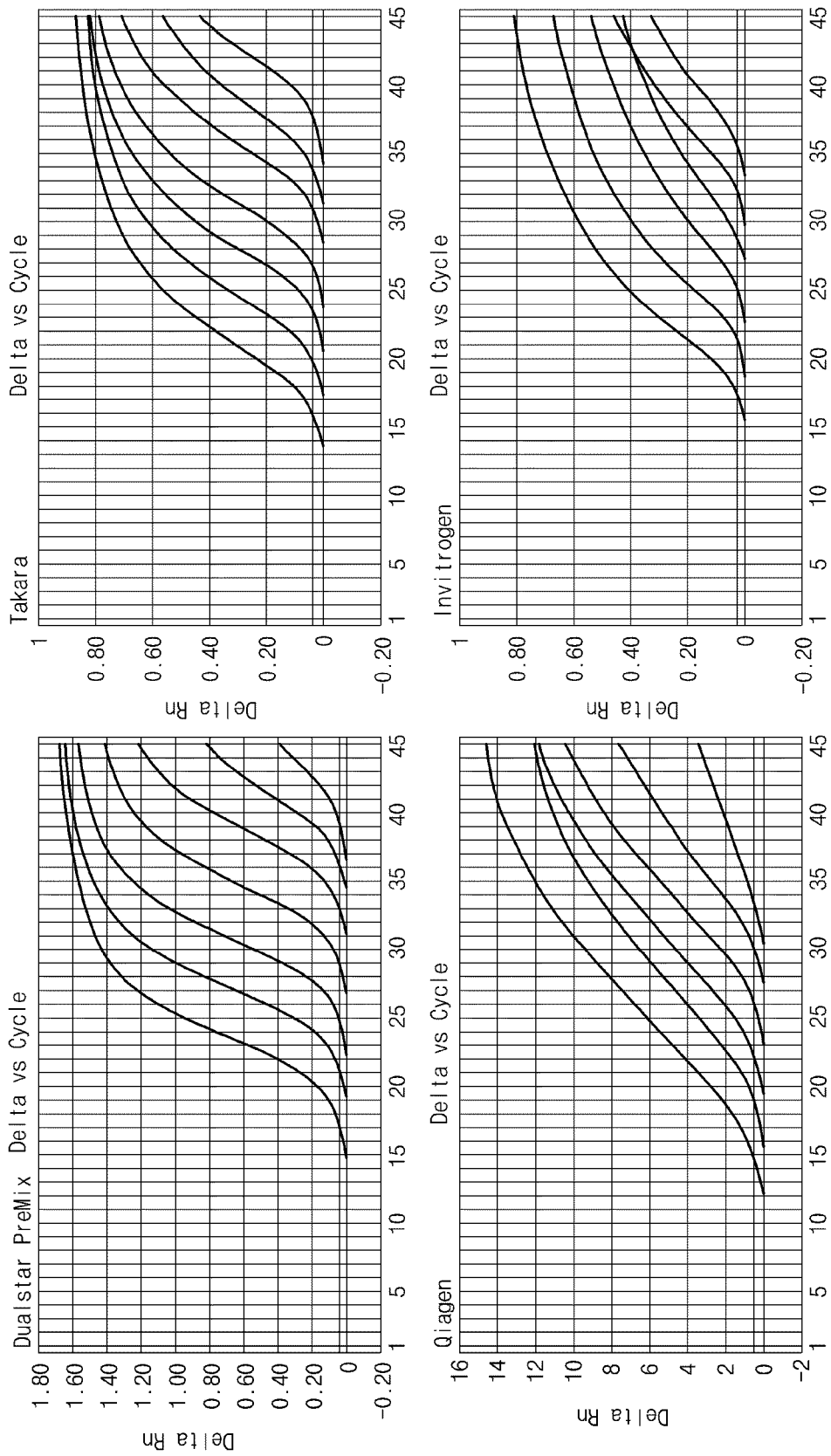
FIG. 41 is a graph illustrating the results of PCR using standard DNA template respectively with the dried premix for hot-start PCR of the present invention containing PPi/PPase and with three other premixes from different manufacturers in the presence of the same probes and primers.
Figure 42:
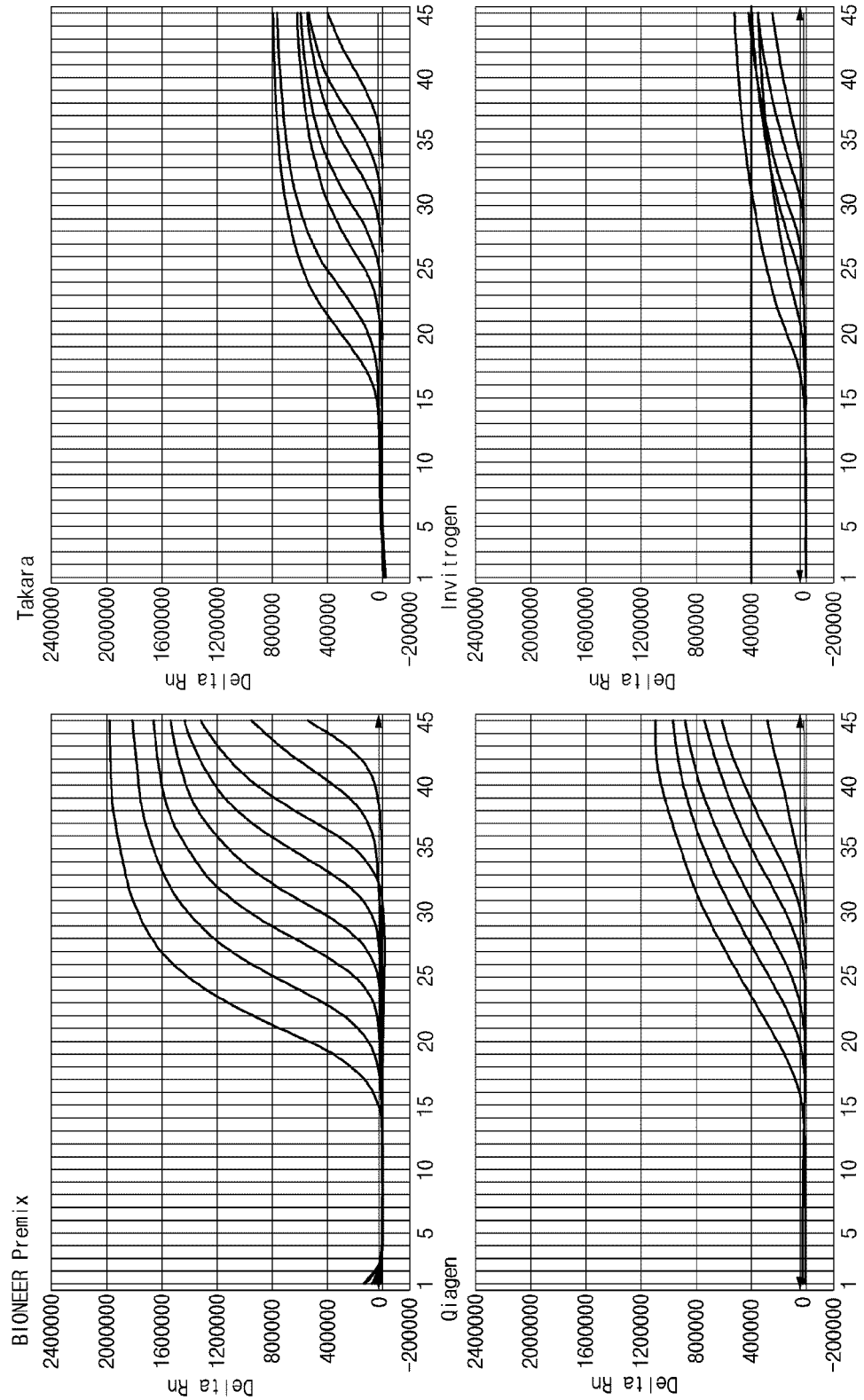
FIG. 42 is a graph illustrating the fluorescence of the dried premix for hot-start PCR of the present invention containing PPi/PPase and of three other premixes, which are presented by the same scale Y. In this graph, differences of fluorescence among products are presented.

As a result, when the dried premix containing PPi/PPase of the present invention (Dualstar™ Premix, Bioneer corporation) and the premix of Takara were used, up to 10 copies of West Nile virus could be detected. When the other two products were used, up to 100 copies of West Nile virus could be detected (FIG. 41). Fluorescence levels were also compared. As a result, when the dried premix of the present invention was used, fluorescence was at least two times as high as fluorescence obtained when Takara premix was used (FIG. 42). The above results indicate that the dried hot-start premix containing PPi/PPase of the present invention demonstrated significantly higher PCR reactivity than other products provided from three different companies.

Example 13

PCR Reactivity of the Dried Hot-Start Premix Containing PPi and PPase but not Containing a Stabilizer To investigate PCR reactivity and stability of the dried hot-start premix containing PPi and PPase (Bioneer corporation, republic of Korea) but not containing the stabilizer Methyl-α-D-Gluco-Pyranoside (α-MG), the dried premix was first prepared by the same manner as described in Example 10. The control premix had the same composition as the above but 0.1 M of α-MG was eliminated therefrom. Drying conditions to prepare those dried premixes were the same as described in Example 10. Real-time PCRs with the dried premix and the control premix were performed under the same conditions.

Primer, probe and standard template DNA sample sequence for real-time PCR were the same as described in Example 11. As a template DNA, plasmid DNA containing the sequence of HBV surface antigen gene (large surface gene) was used. The template DNA having the copy number of $1 \times 10^0 \sim 1 \times 10^6$ copy/µl was added to each well by 10 µl. Conditions for real-time PCR were the same as described in Example 10.

7500 Fast system (Applied Biosystem) was used for real-time PCR. The operation program and analysis program were executed according to the manufacturer's instructions. Real-time PCR was performed as follow: predenaturation at 95° C. for 5 minutes, denaturation at 95° C. for 20 seconds, annealing/extension at 55° C. for 40 seconds, and detection of fluorescence (45 cycles). Upon completion of the PCR, the PCR product was examined by the analysis program operating in the 7500 Fast system.

Figure 43:
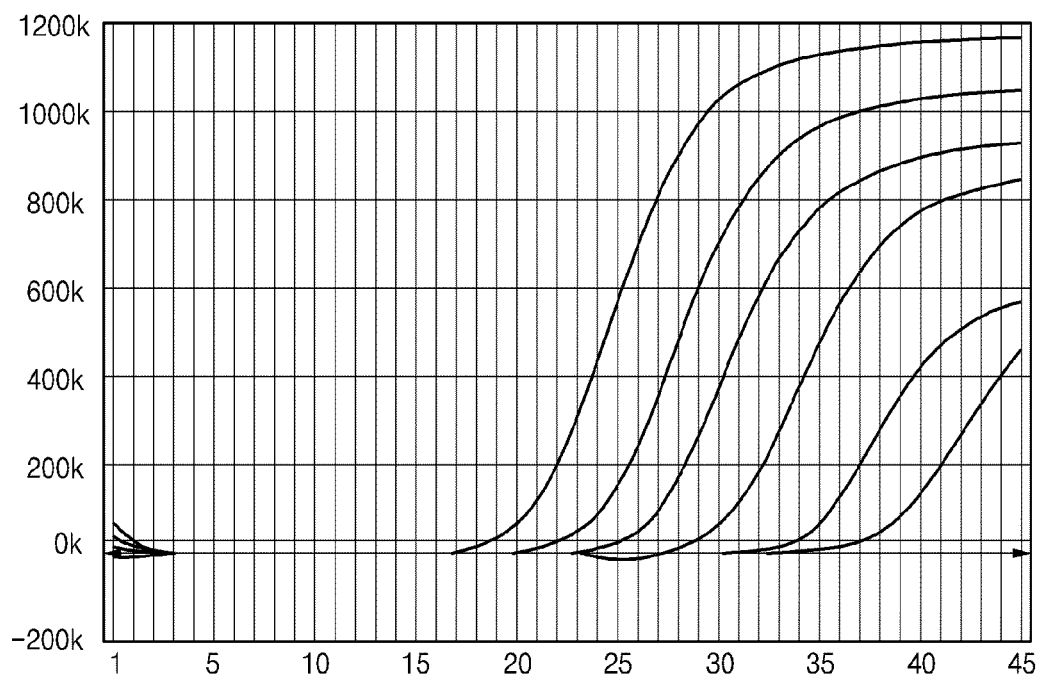
FIG. 43 is a graph illustrating the result of real-time PCR performed with the dried premix containing PPi and PPase but not containing a stabilizer.
Figure 43:
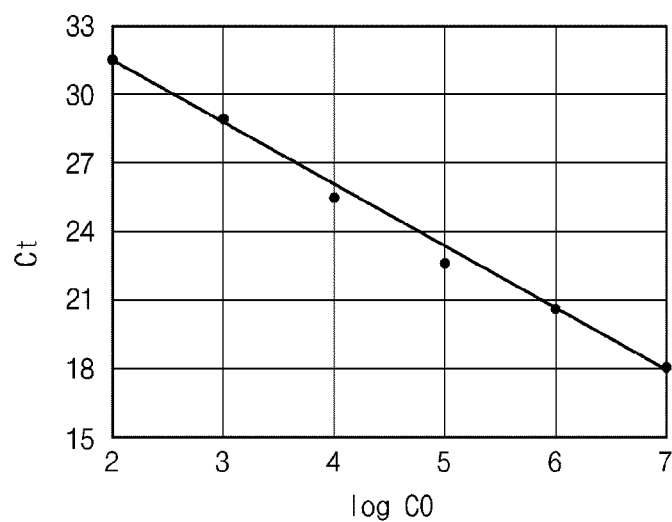
Figure 44:
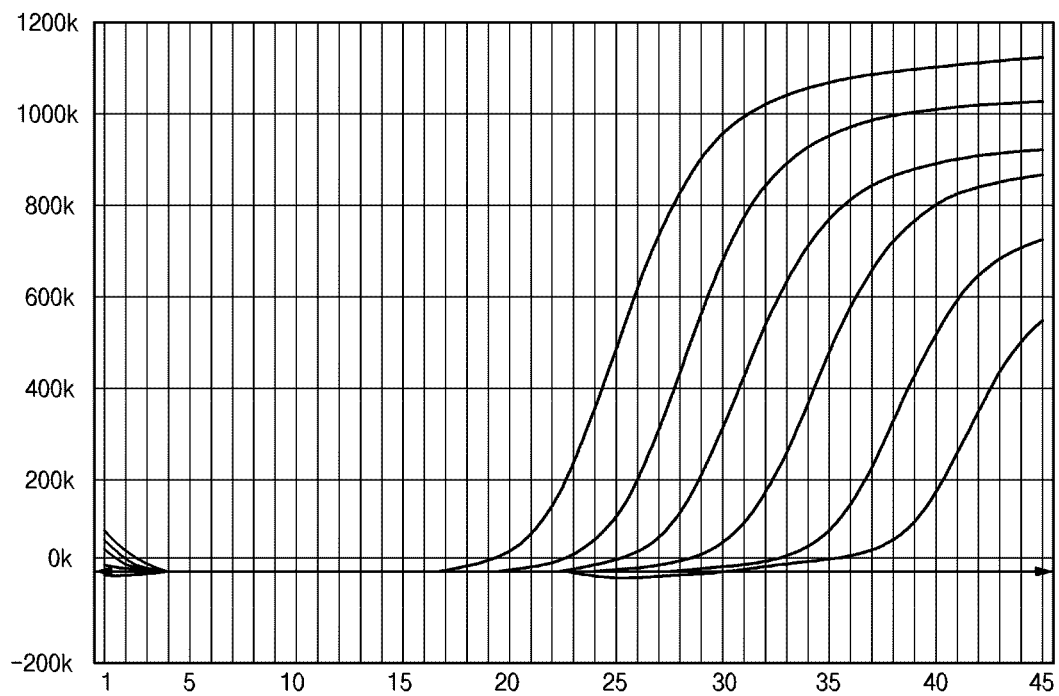
FIG. 44 is a graph illustrating the result of real-time PCR performed with the dried premix containing PPi, PPase and a stabilizer as well under the same conditions.
Figure 44:
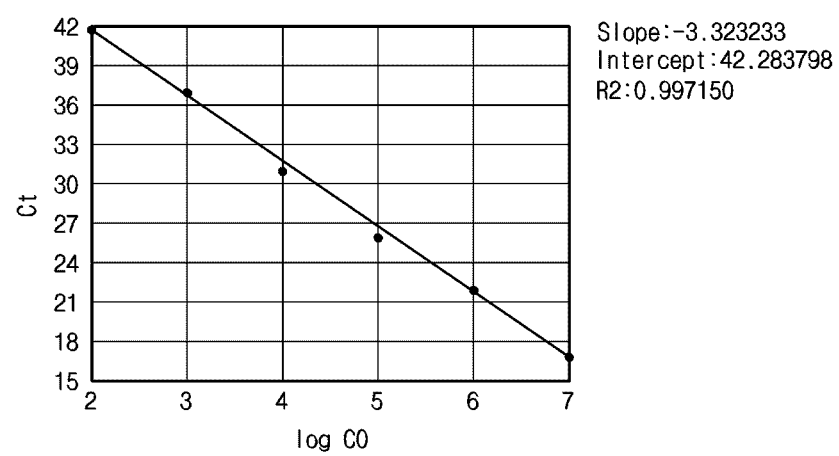
Figure 45:
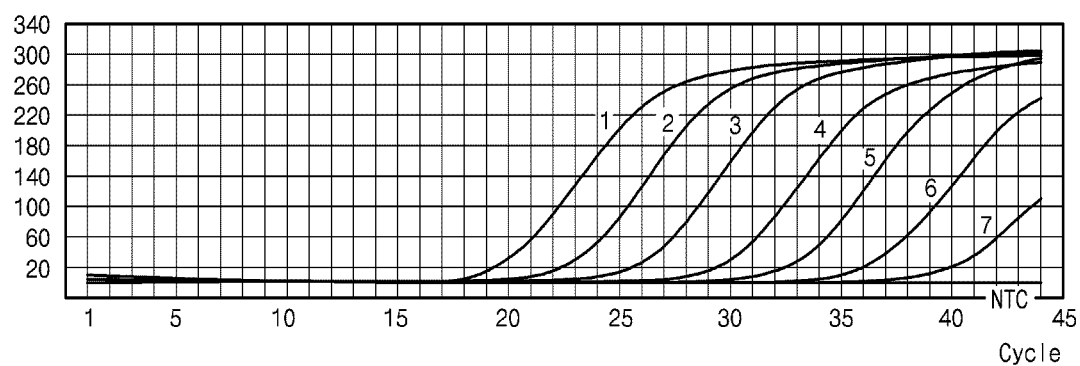
FIG. 45 is a graph illustrating the result of PCR using Exicycler version 3 real-time PCR machine (Bioneer corporation, republic of Korea).
Figure 45:
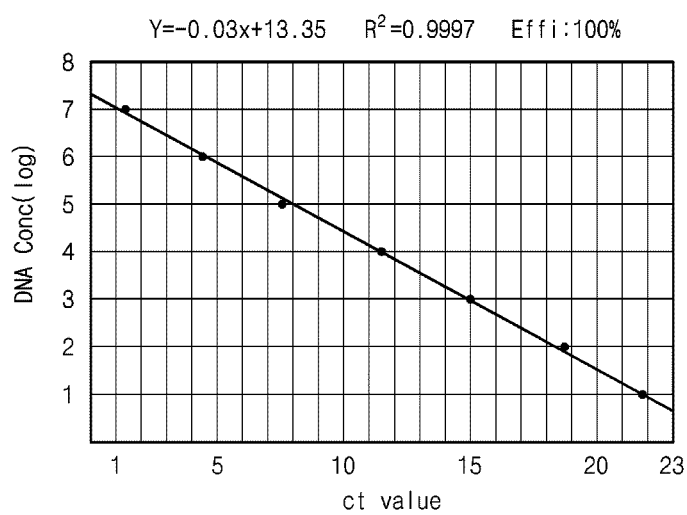
Figure 46:
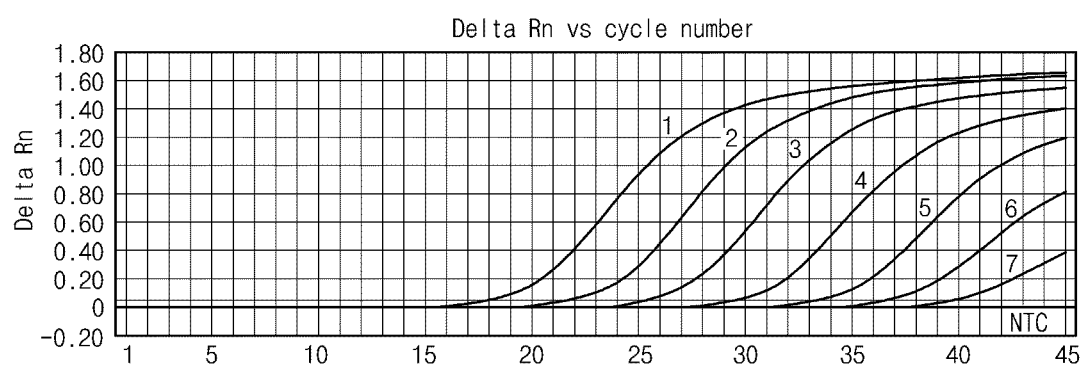
FIG. 46 illustrates the result of PCR using 7500 Fast (Applied Biosystems).
Figure 46:
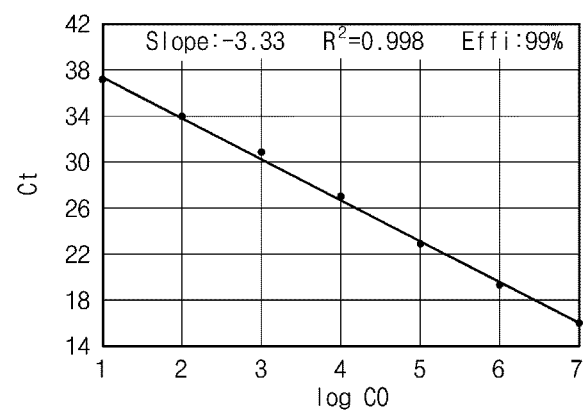
Figure 47:
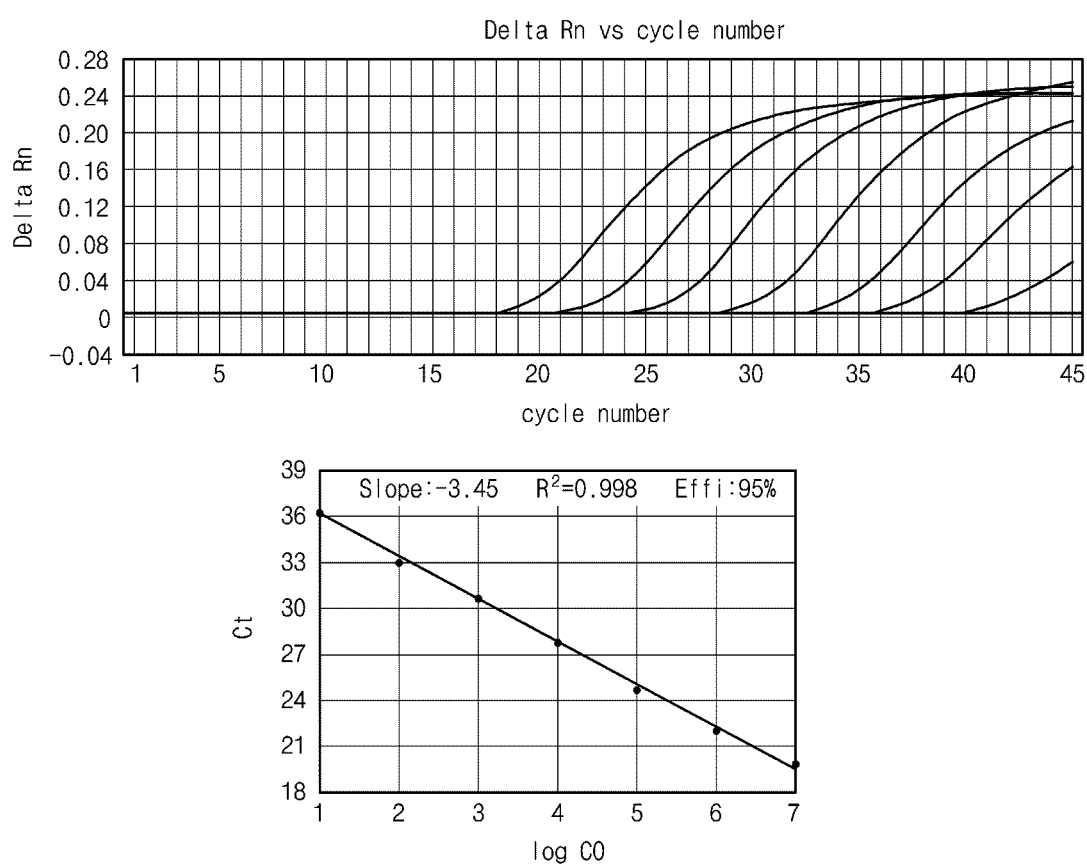
FIG. 47 illustrates the result of PCR using 7500 (Applied Biosystems).
Figure 48:
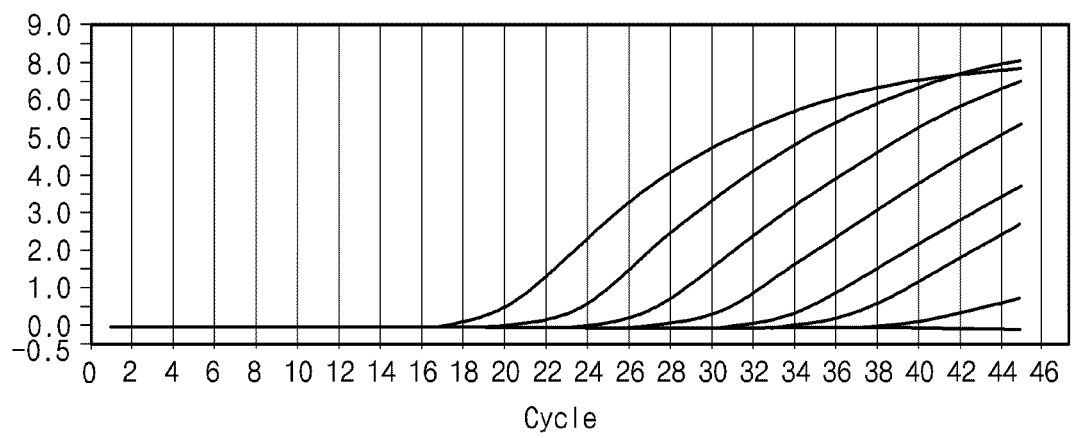
FIG. 48 illustrates the result of PCR using Step-One (Applied Biosystems).
Figure 48:
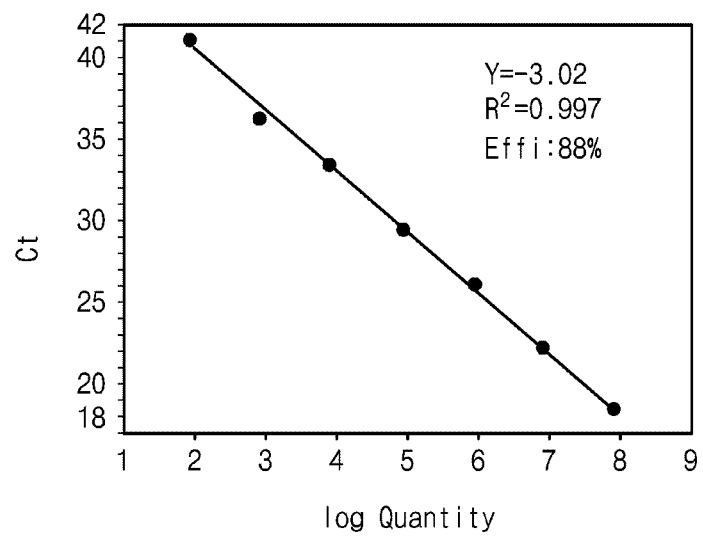
Figure 49:
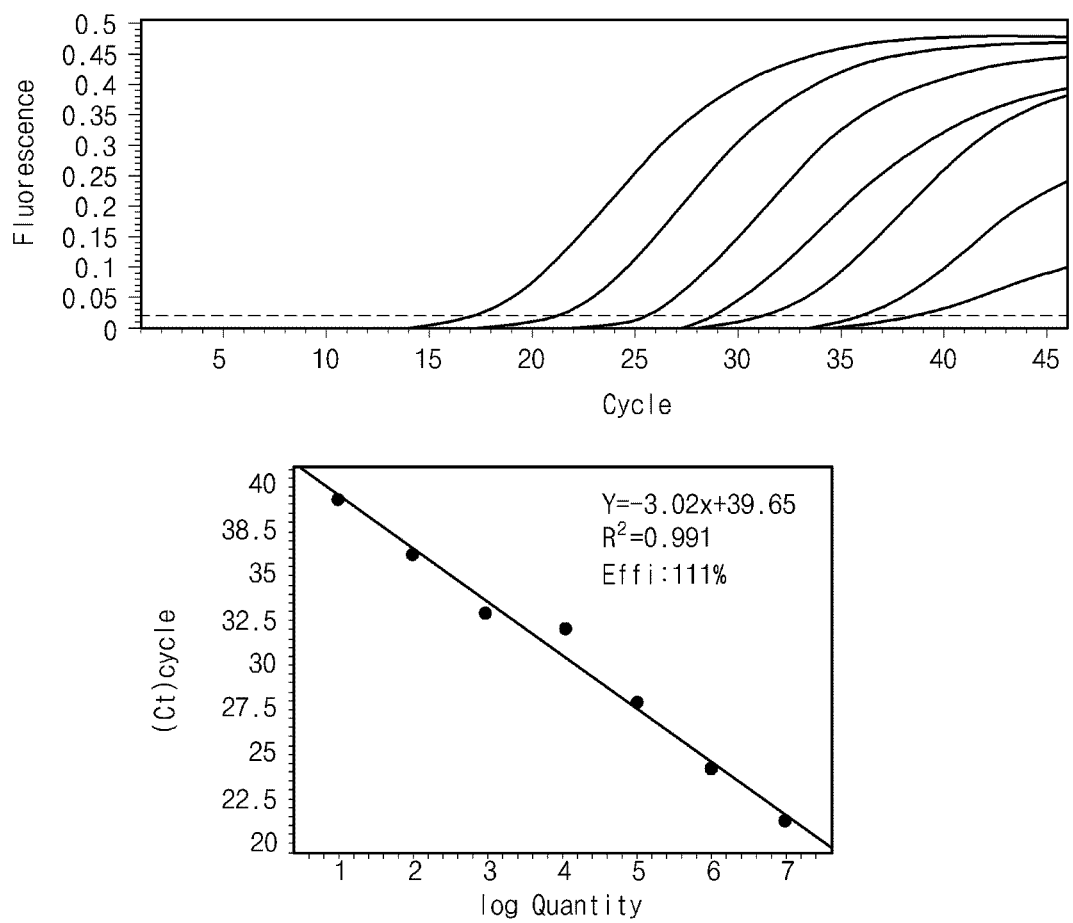
FIG. 49 illustrates the result of PCR using DNA engine opticon (MJ Research Inc.).

As a result, the reactivity of the dried hot-start premix not-containing a stabilizer was not much different from the reactivity of the control premix containing a stabilizer. In particular, Ct values were similar for the same standard sample (FIGS. 43 and 44). The above results indicate that the addition of a stabilizer does not affect PCR reactivity of the dried hot-start premix.

Example 14

Reactivity of the Dried Hot-Start Premix Containing PPi and PPase According to the Real-Time PCR Devices To investigate whether reactivity of the dried hot-start premix containing PPi and PPase (Bioneer corporation, republic of Korea) could be different by real-time PCR devices, 5 different real-time PCR devices provided from three companies were used. Composition of the dried premix and conditions for drying were the same as described in Example 10. Real-time PCRs were performed with the dried premix using the 5 PCR devices. The real-time PCR devices used in this invention were as follows: Exicycler version 3 (Bioneer corporation, republic of Korea), Applied Biosystem 7500, 7500 Fast system, Stepone system (Applied Biosystem) and DNA engine opticon (MJ Research Inc.). Operation program and analysis program were executed according to the manufacturer's instructions. Real-time PCR was performed in the same manner as described in Example 10. Upon completion of the PCR, the PCR product was examined by the analysis program operating in each PCR device.

Primer, probe and standard template DNA sample sequence for real-time PCR were the same as described in Example 12. As a template DNA, plasmid DNA containing the sequence of West Nile virus E gene was used. The template DNA having the copy number of $2 \times 10^0 \sim 2 \times 10^6$ copy/µl was added to each well by 5 µl. Conditions for real-time PCR were the same as described in Example 10.

As a result, the dried hot-start premix showed consistent results with different PCR devices (FIGS. 45-49). Therefore, it was confirmed that the dried composition of the present invention is not limited to a specific device but applied in diverse general devices.

Example 15

PCR Reactivity of the Dried Hot-Start Premix Containing PPi and PPase Examined by Using Diverse Target Genes To investigate whether PCR reactivity of the dried hot-start premix containing PPi and PPase could be varied from different target genes or not, three different target genes (West Nile virus E gene, Varicella-zoster virus ORF gene and HBV surface antigen gene antigen gene) were used. Conditions for the preparation of the dried hot-start premix containing PPi and PPase were the same as described in Example 10.

Primer, probe and standard template DNA sample sequence for real-time PCR were the same as described in Examples 10, 11 and 12. As a template DNA, plasmid DNA containing the sequence of West Nile virus E gene, Varicella-zoster virus ORF gene or HBV surface antigen gene was used. The template DNA having the copy number of $2 \times 10^0 \sim 2 \times 10^6$ copy/µl was added to each well by 5 µl. Conditions for real-time PCR were the same as described in Example 10.

Exicycler version 3.0 (Bioneer corporation, republic of Korea) was used for real-time PCR. The operation program and analysis program were executed according to the manufacturer's instructions. Real-time PCR was performed as follow: predenaturation at 95° C. for 5 minutes, denaturation at 95° C. for 20 seconds, annealing/extension at 55° C. for 40 seconds, and detection of fluorescence (45 cycles). Upon completion of the PCR, the PCR product was examined by the analysis program operating in the Excicycler real-time PCR device.

Figure 50:
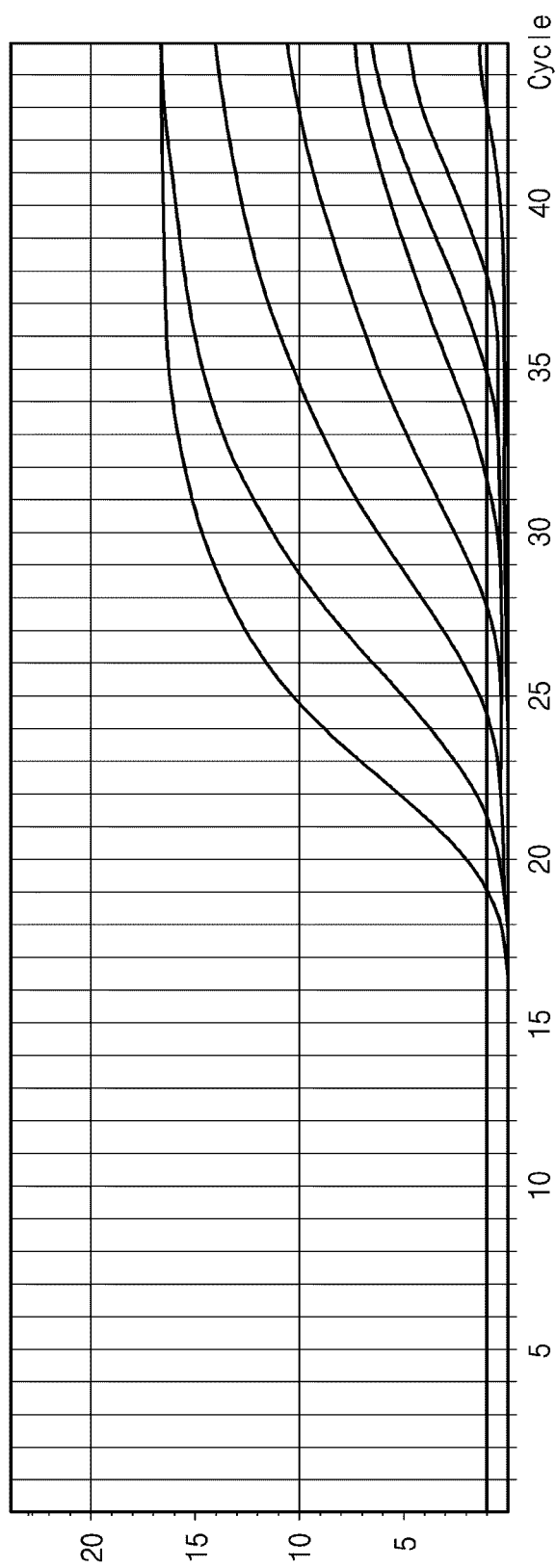
FIG. 50 is a graph illustrating the result of real-time PCR using DNA template containing West Nile virus E gene.
Figure 51:
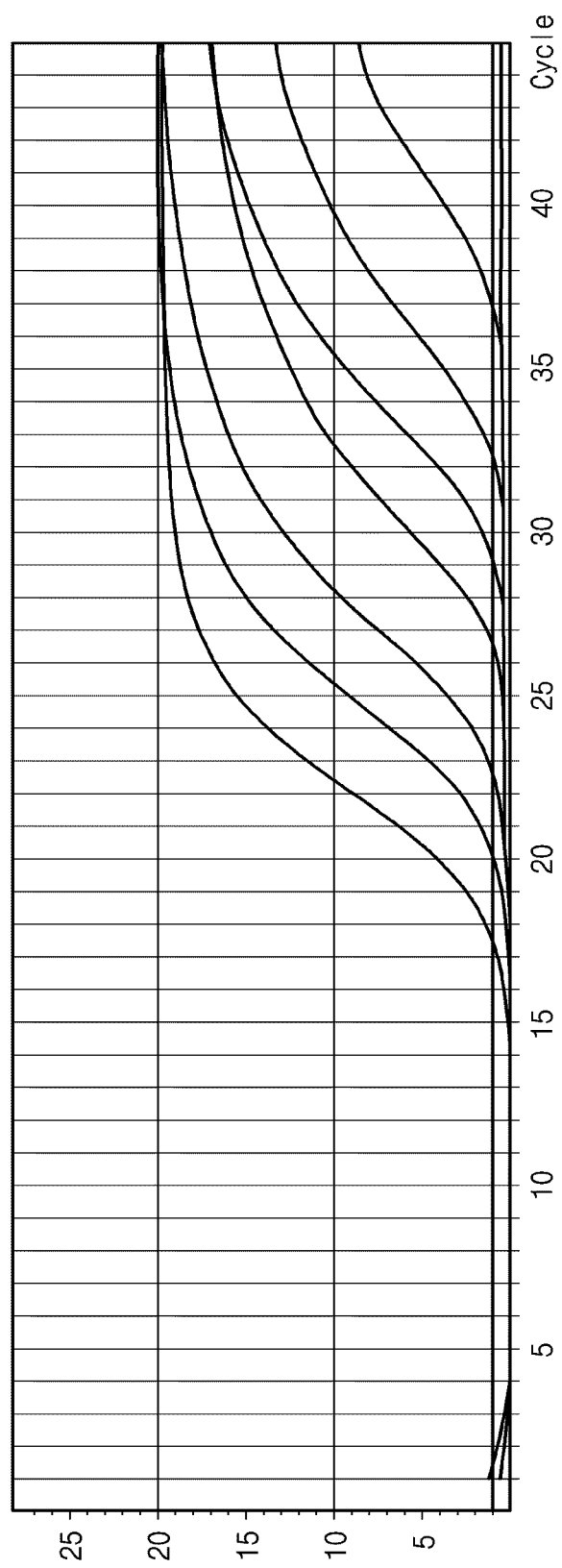
FIG. 51 is a graph illustrating the result of real-time PCR using DNA template containing Varicella-zoster virus ORF gene.
Figure 52:
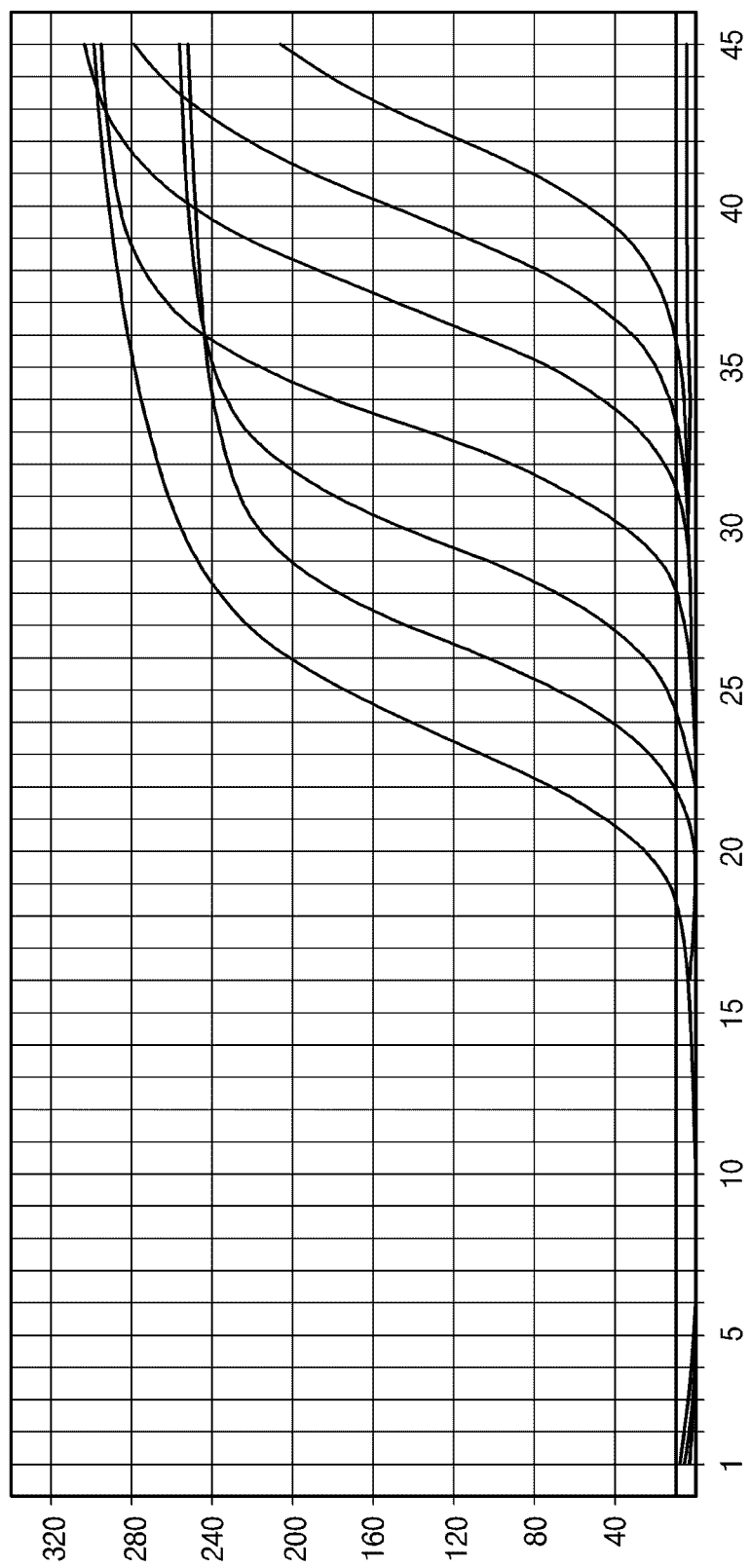
FIG. 52 is a graph illustrating the result of real-time PCR using DNA template containing HBV surface antigen gene.

As a result, reactivity was all consistent with three different target genes having different gene sequences, different nucleotide compositions and different lengths of target sequences amplified (FIGS. 50-52). The above results indicate that the dried hot-start premix of the present invention can be applied in a variety of target genes.

Example 16

Real-Time PCR Using the Dried Hot-Start Premix Containing PPi, PPase and CyBr Green Fluorescent Dye To investigate reactivity of the dried hot-start premix containing PPi, PPase and CyBr green fluorescent dye, 10× CyBr green fluorescent material (Greenstar™, Bioneer corporation, republic of Korea) was added at the final concentration of 0.6× to 50 µl of reaction mixture comprising 10 mM Tris-HCl pH 9.0, 40 mM KCl, 2.0 mM $MgCl_2$, 4 dNTPs (250 µM each, final concentration: 0.25 mM), 2.5 U Top DNA polymerase, 0.01% Tween 20 and a stabilizer, to which PPi and PPase (Bioneer corporation, republic of Korea) were added by respectively 2.0 mM and 92.5 mU, resulting in the preparation of a composition. Drying of the hot-start premix was performed in the same manner as described in Example 10. For the control, a mastermix solution having the same composition was prepared prior to use. The fluorescent material herein facilitates analysis without a sequence specific fluorescent probe simply by measuring fluorescence generated from double-stranded DNA where the fluorescent material was intercalated during the template DNA amplification.

Lambda DNA (Bioneer corporation, republic of Korea) was used as a template at different concentrations from 0.1 ng to 0.1 pg. L127_F primer represented by SEQ. ID. NO: 34 (5'-GAACTGATGAGCGATCCGAATAG-3') and L127_R primer represented by SEQ. ID. NO: 35 (5'-CCACCACT-GATTAGCGAATGC-3') generating 127 bp PCR product were used at the concentration of 10 pmol per 50 µl reaction. PCR was performed by using ABI 7500 Fast system (Applied Biosystems) as follows; predenaturation at 95° C. for 1 minute, denaturation at 95° C. for 5 seconds, annealing at 55° C. for 35 seconds simultaneously with extension (40 cycles). After dissociation step, the melting curve of the amplified product was made to confirm PCR reactivity and specificity.

Figure 53:
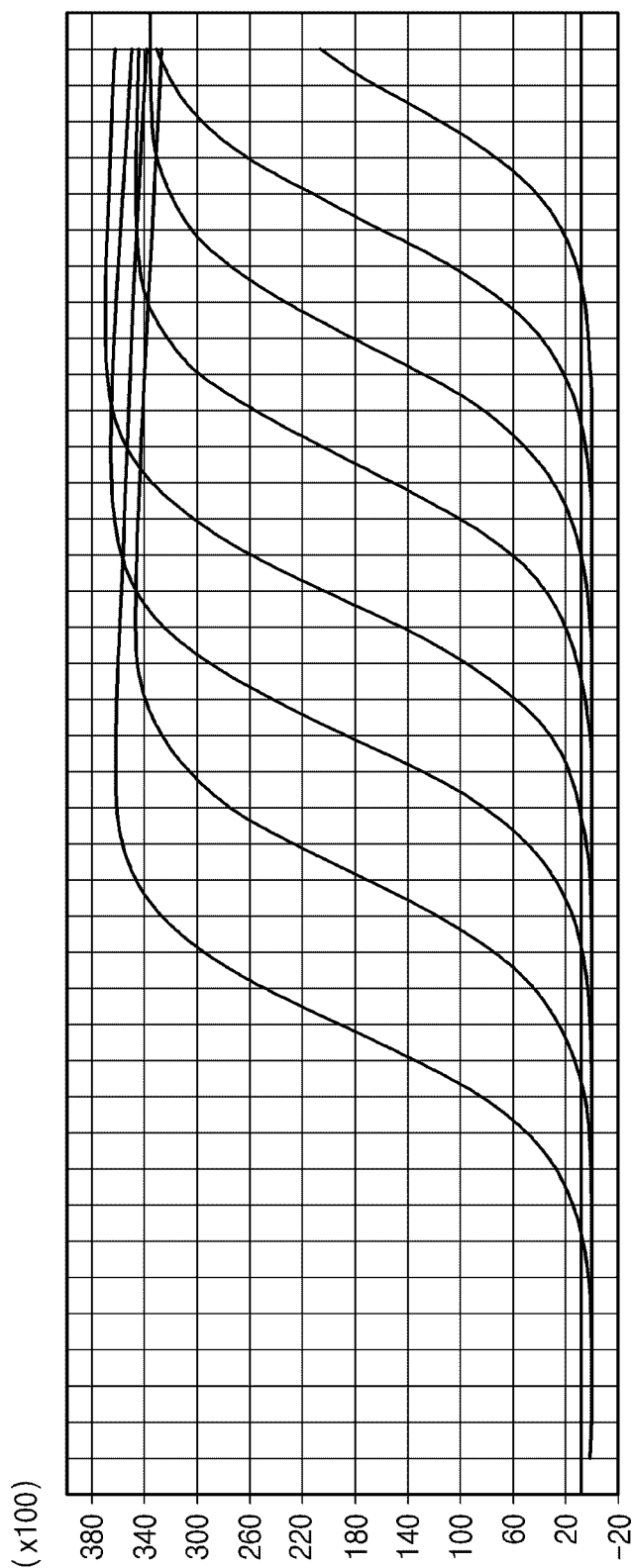
FIG. 53 is a graph illustrating the result of real-time PCR using the dried premix for hot-start PCR.
Figure 54:
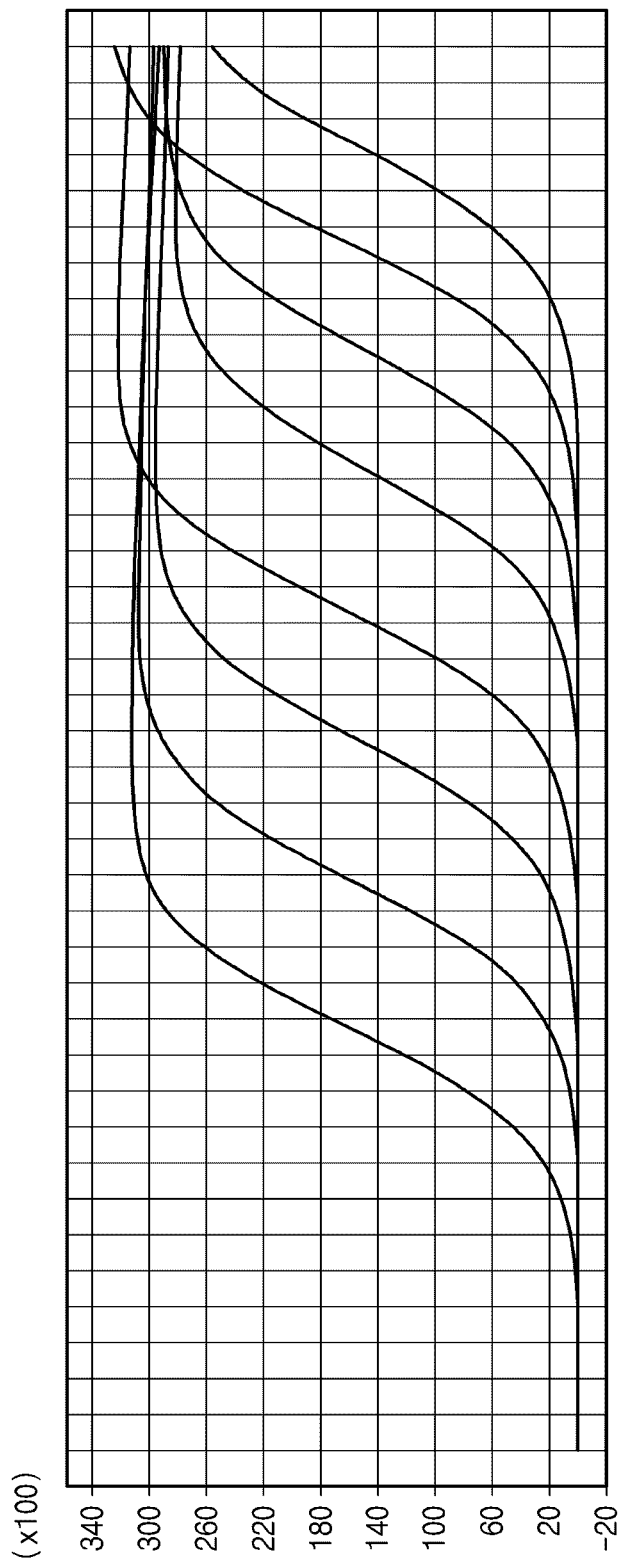
FIG. 54 is a graph illustrating the result of real-time PCR using the master mix solution (control) having the same composition as the dried premix.
Figure 55:
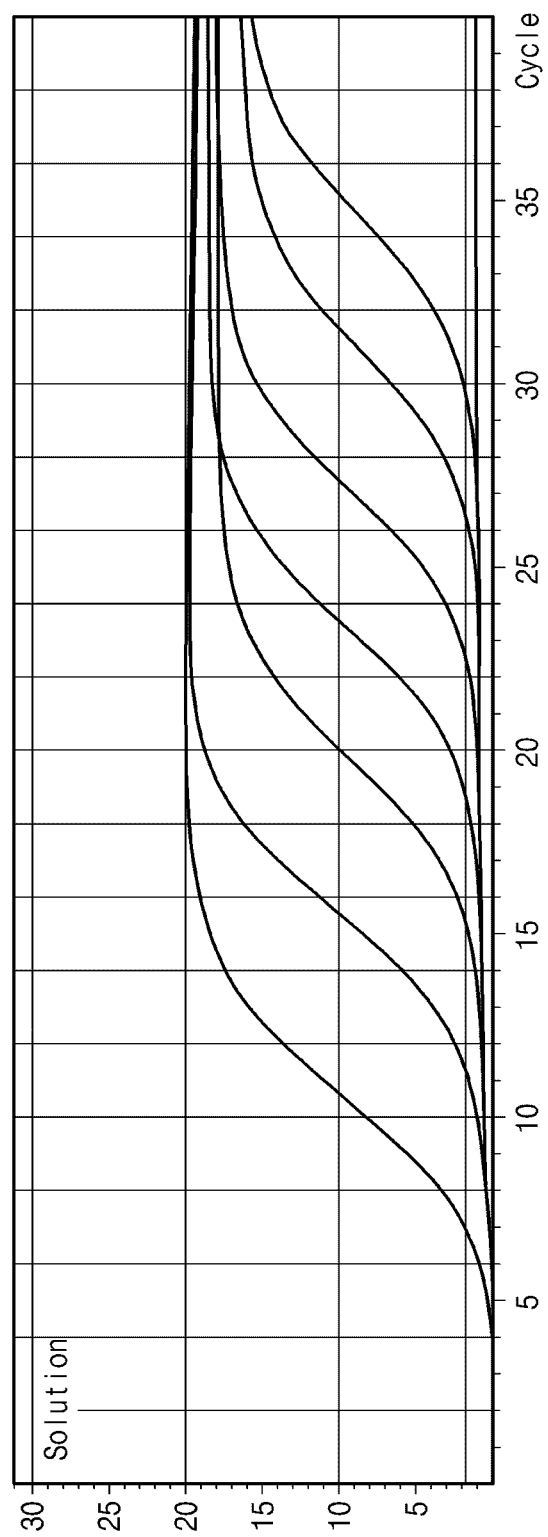
FIG. 55-FIG. 60 are graphs illustrating the results of real-time PCR with the samples obtained from the dried premix stored at 50° C. every 1-2 days until the $9^{th}$ day from preparation. For the control, a solution having the same composition as the premix was used.
Figure 56:
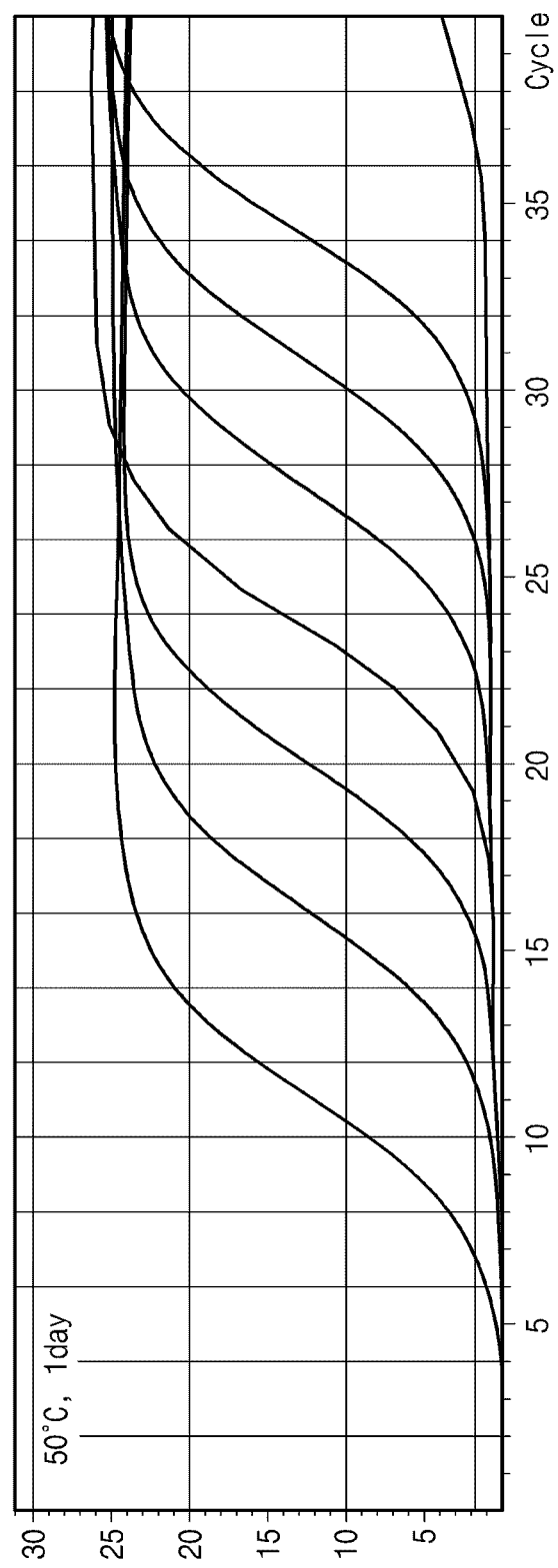
Figure 57:
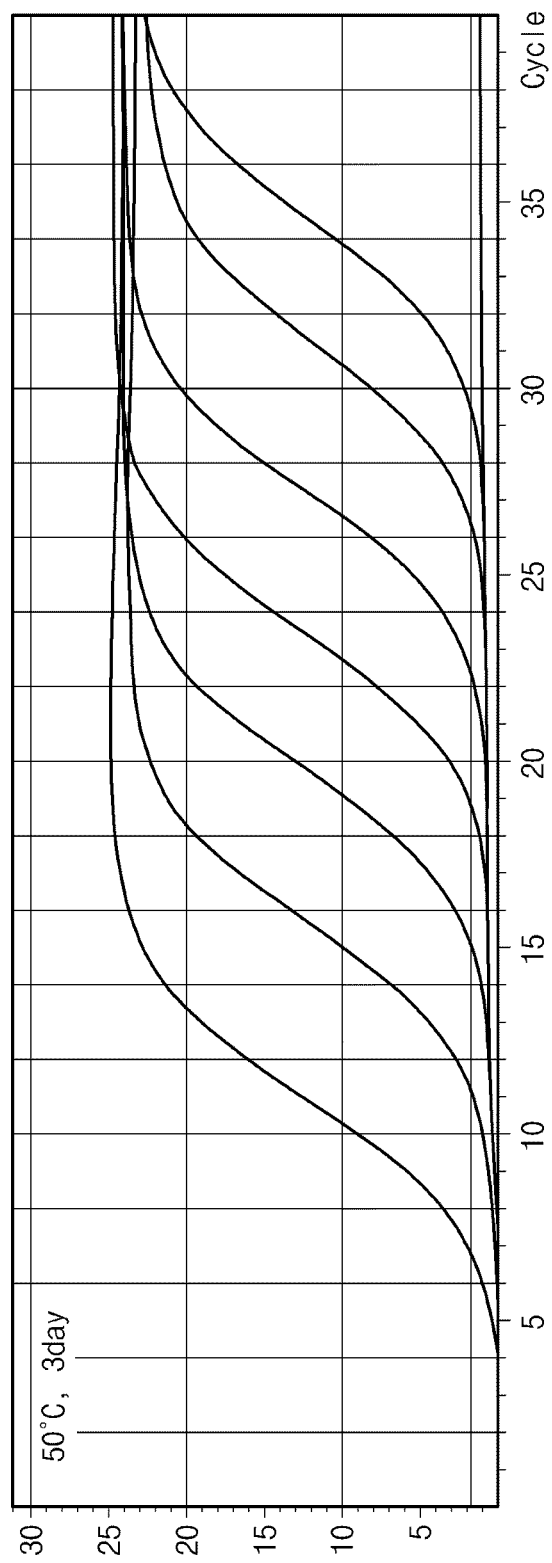
Figure 58:
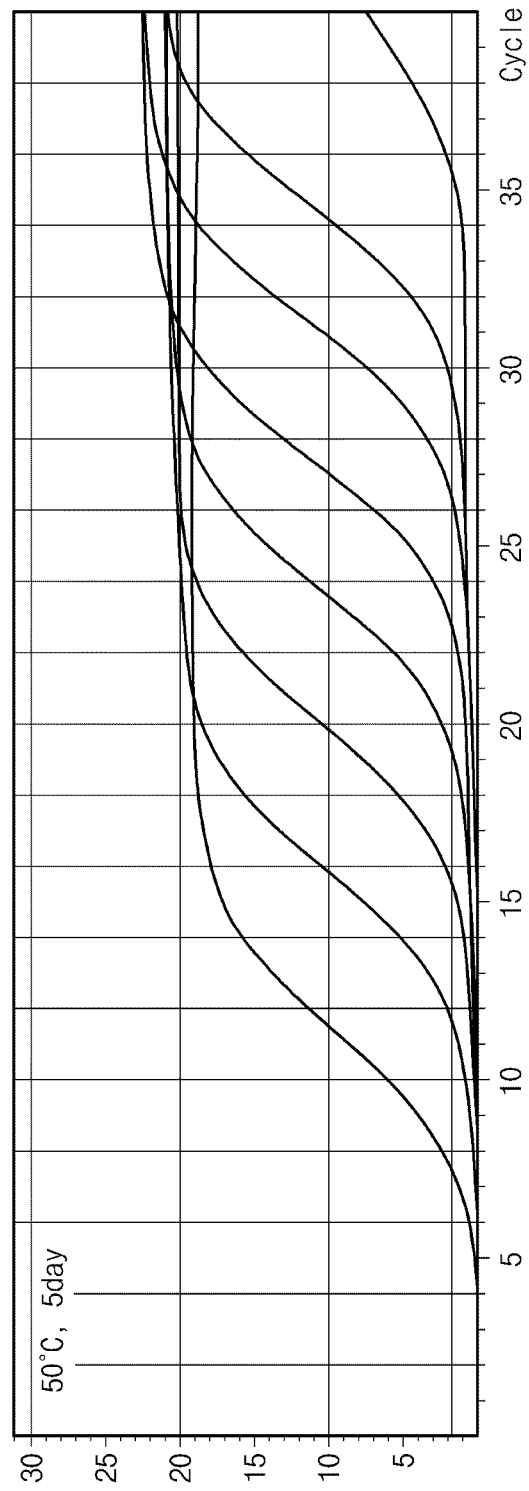
Figure 59:
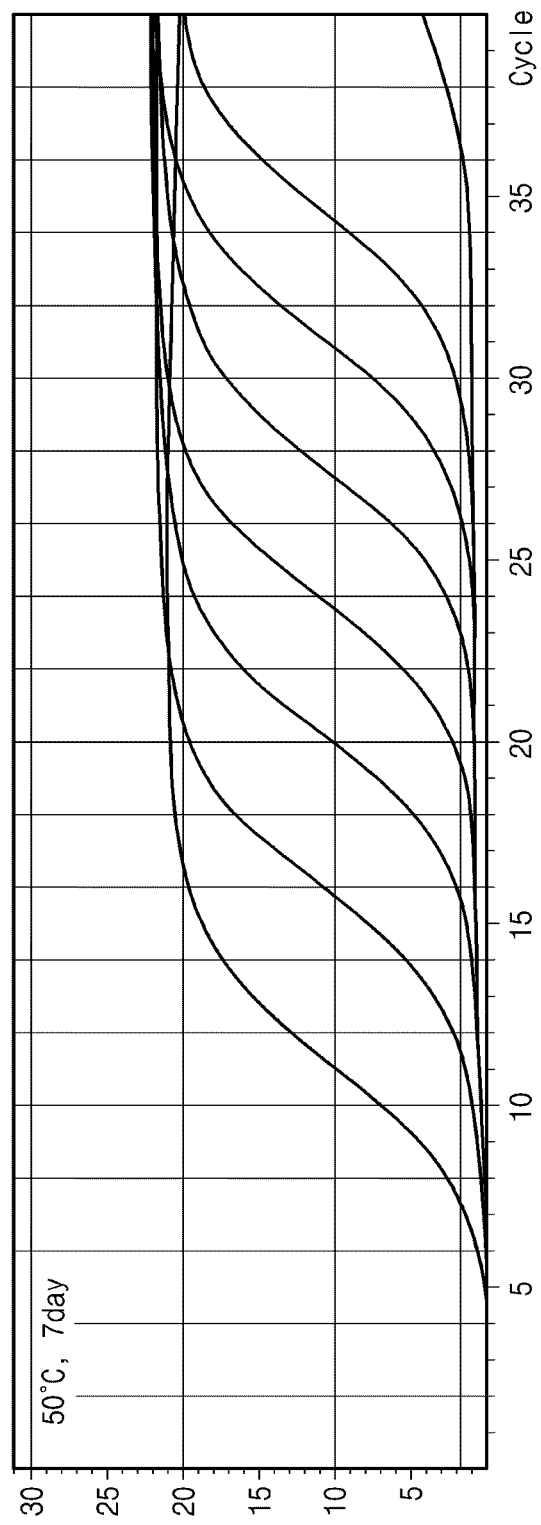
Figure 60:
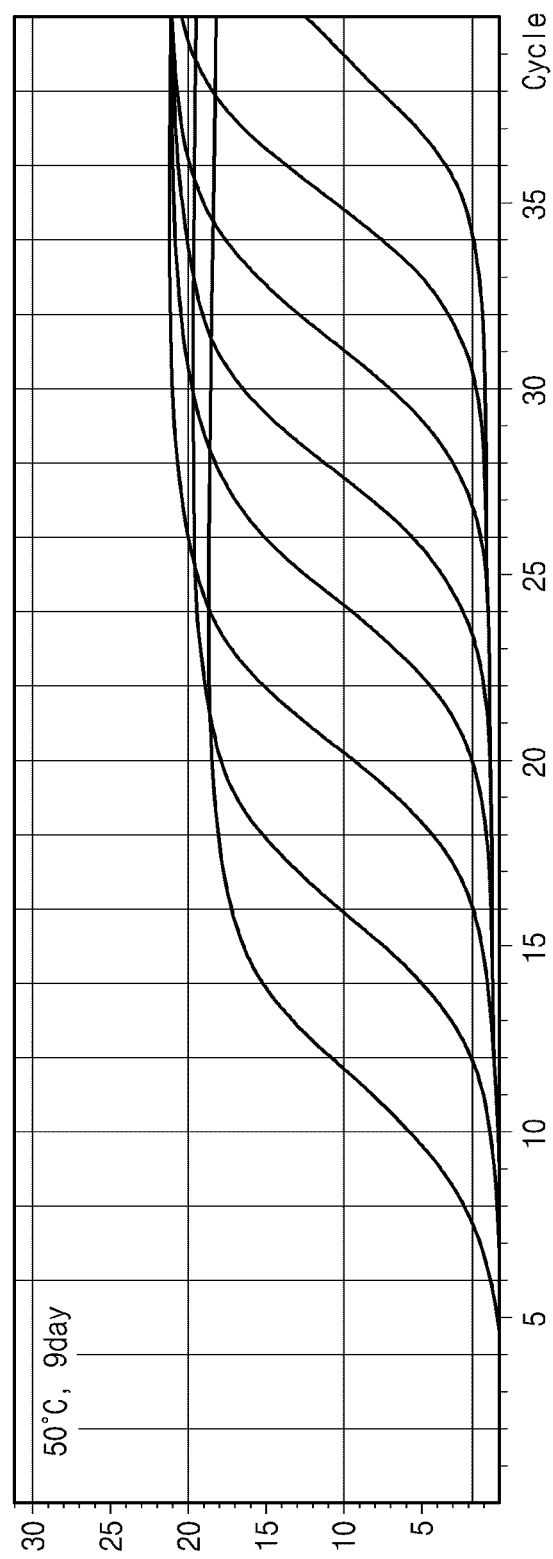

As a result, the results of PCR using the dried hot-start premix were similar to that of PCR using the control premix (FIGS. 53 and 54). Therefore, it was confirmed that PCR reactivity of the dried hot-start premix containing PPi, PPase and CyBr green fluorescent dye was maintained in real-time PCR.

Example 17

Storage Stability of the Dried Premix Containing PPi, PPase and CyBr Green Fluorescent Material To investigate storage stability of the dried hot-start premix containing PPi, PPase and CyBr green fluorescent material, the dried premix was first prepared in the same manner as described in Example 16. For the control, the solution having the same composition was prepared prior to use. Drying was performed in SuperCentra (Bioneer corporation, republic of Korea) in which the temperature outside of the device was set at 40° C. and the temperature inside of the device was set at 36° C., for 50 minutes after pre-heating for 5 minutes. The prepared premix was stored in a 50° C. reactor, during which an 8-well strip containing the dried premix was taken every day from day 0 to day 9. The strip was stored in a deep-freezer until real-time PCR or used for real-time PCR on the day of sampling under the same conditions as provided for the control. The same template DNA as used in Example 16 was used. Experimental conditions were also the same as described in Example 16. PCR and analysis of the results were performed in the same manner as described in Example 16.

As a result, the dried composition of the present invention demonstrated similar reactivity as that of the primary premix composition even after 7 day-storage at 50° C. On the $9^{th}$ day of storage at 50° C., fluorescence was compared with that of the primary dried composition. As a result, fluorescence was lightly reduced, but this reduction was not so strong as to affect the reactivity (FIGS. 55-60). The result of 50° C. experiment was re-calculated to investigate reactivity under −20° C. storage. As a result, the dried premix was expected to retain its reactivity similar to that of the control until 1,152 days (3.1 year) (Lee sangyong, Reliability engineering, 1999, Hyungseul Publishing Company).

Example 18

PCR Reactivity of the Dried Hot-Start Premix Containing CyBr Green Fluorescent Dye, PPi and PPase and the Conventional Hot-Start Premix To compare reactivity between the dried hot-start premix containing CyBr green fluorescent dye, PPi and PPase of the present invention and the conventional hot-start premix, Takara SYBR Premix Ex Taq™ (Takara, Cat#:RR041), ABI SYBR® Green PCR Master Mix (ABI, Cat#:4309155) and Invitrogen SYBR GreenER™ qPCR SuperMix Universal (Invitrogen, Cat#:11762-100) were selected for the comparative groups. Drying was performed in the same manner as described in Example 16 to prepare the dried hot-start premix containing CyBr green fluorescent dye, PPi and PPase.

Primer, probe and standard template DNA for real-time PCR were the same as described in Example 16. Real-time PCR was performed in the same manner as described in Example 16. The same primers, probes and standard template DNA samples were used for those three premix products from three different companies and at this time the conditions for real-time PCR and mastermix preparation were set according to the manufacturer's instructions.

7500 Fast system (Applied Biosystem) was used for real-time PCR. The operation program and analysis program were executed according to the manufacturer's instructions. Upon completion of the PCR, the PCR product was examined by the analysis program operating in the 7500 Fast system.

Figure 61:
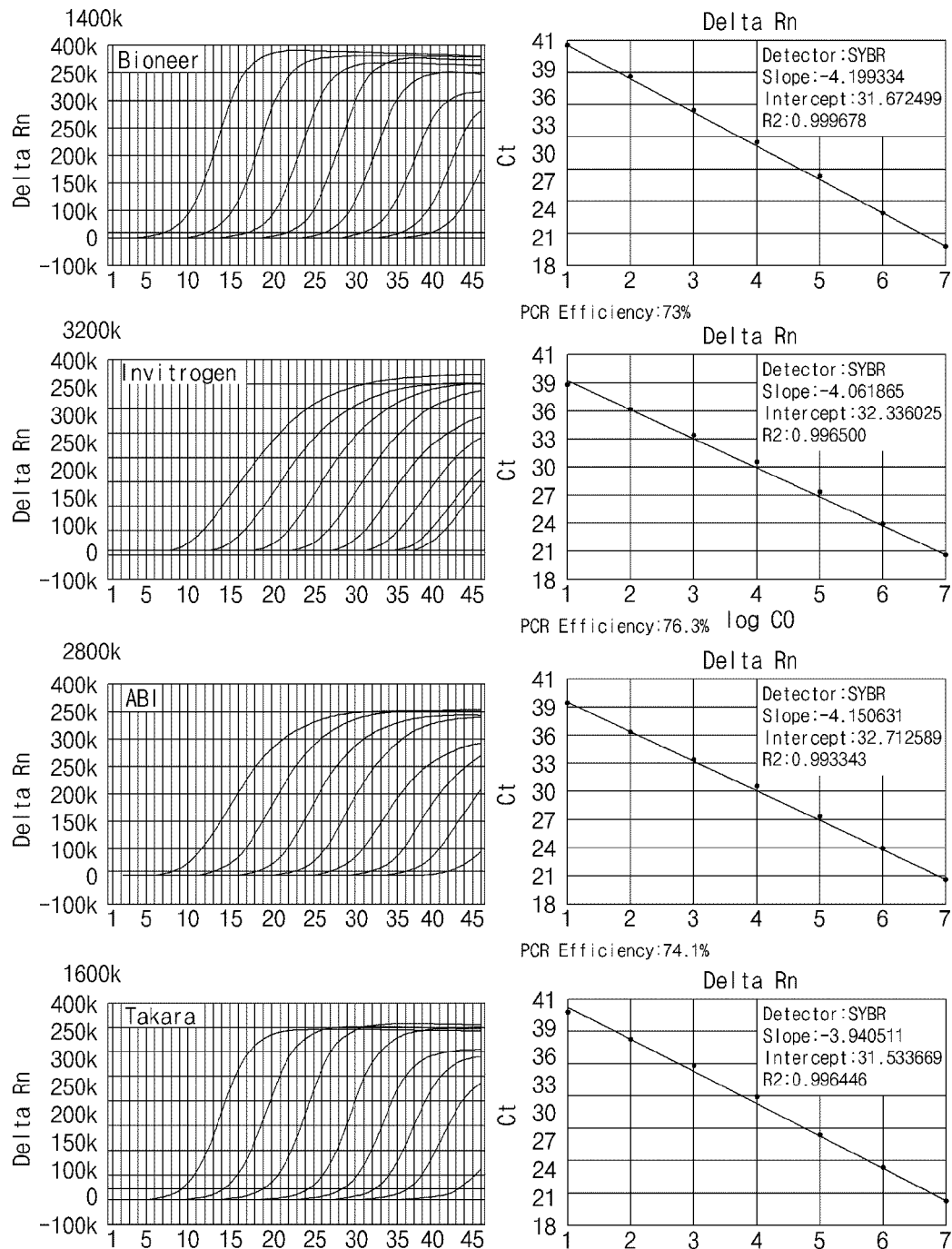
FIG. 61 is a set of graphs illustrating the results of PCR using standard DNA template respectively with the dried premix for hot-start PCR containing PPi/PPase and a fluorescent material (Greenstar™), and with three other premixes from different manufacturers in the presence of the same probes and primers. In this figure, amplification curves are presented.

As a result, the dried hot-start premix containing CyBr green fluorescent dye, PPi and PPase demonstrated similar PCR efficiency and amplification curve with the three conventional premixes provided from three different companies (FIG. 61).

Example 19

PCR Reactivity of the Dried Hot-Start Premix Comprising PPi, PPase, Primer Set and Probe Labeled with Fluorescent Dye PCR reactivity of the dried hot-start premix comprising PPi, PPase (Bioneer corporation, republic of Korea), target specific primer set and probe labeled with fluorescent dye was investigated. 10 pmol of target specific primer set comprising a forward primer (1 μl/20 μl reaction volume) and a reverse primer (1 μl/20 μl reaction volume) and 10 pmole of probe labeled with fluorescent dye (1 μl/20 μl reaction volume) were added to the reaction mixture comprising 10 mM Tris-HCl pH 9.2, 60 mM KCl, 1.5 mM MgCl$_2$, 4 dNTPs (250 μM each), 1 U wTfi DNA polymerase, 0.01% Tween 20, 2.0 mM PPi, 37 mU PPase, 1.2 μg BSA and a stabilizer (Methyl-α-D-Gluco-Pyranoside: α-MG) to prepare the dried premix. For the control, the dried premix having the same composition as the above but not containing a primer set and a probe was prepared. Drying was performed in SuperCentra (Bioneer corporation, republic of Korea) in which the temperature outside of the device was set at 40° C. and the temperature inside of the device was set at 36° C., for 25 minutes. Real-time PCR was performed under the same conditions.

Primer, probe and standard template DNA sample sequence for real-time PCR were the same as described in Example 11. As a template DNA, plasmid DNA containing the sequence of HBV surface antigen gene (large surface gene) was used. The template DNA having the copy number of $1\times10^0 \sim 1\times10^6$ copy/μl was added to each well by 5 μl. The control premix that did not contain the primer set and the probe was added with 10 pmole of the primer set comprising a forward primer (1 μl/20 μl reaction volume) and a reverse primer (1 μl/20 μl reaction volume) and 10 pmole of probe labeled with fluorescent dye (1 μl/20 μl reaction volume). 12 μl of DEPC treated distilled water was added to make the final volume to be 20 μl/well. To the hot-start premix containing the same concentration, the same sequence primer set and probe from the beginning of the drying process was added with 15 μl of DEPC treated distilled water to make the final reaction volume to be 20 μl/well. Rest of the real-time PCR conditions was the same as described in Example 10.

7500 Fast system (Applied Biosystem) was used for real-time PCR. The operation program and analysis program were executed according to the manufacturer's instructions. Real-time PCR was performed as follow: predenaturation at 95° C. for 5 minutes, denaturation at 95° C. for 20 seconds, annealing/extension at 55° C. for 40 seconds, and detection of fluorescence (45 cycles). Upon completion of the PCR, the PCR product was examined by the analysis program operating in the 7500 Fast system.

Figure 62:
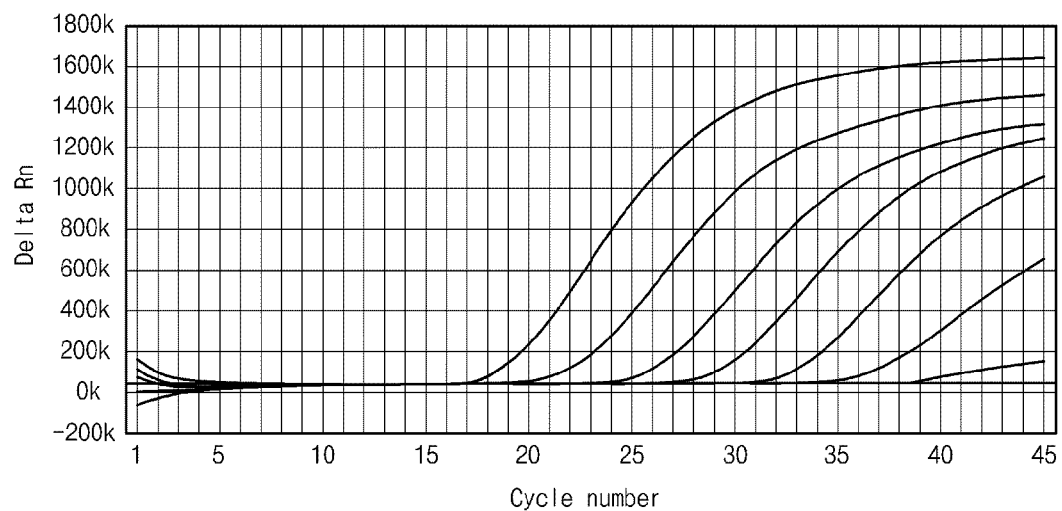
FIG. 62 presents amplification curves and a standard line illustrating the result of real-time PCR with the dried premix containing PPi and PPase but not containing a target specific primer set and probe performed in the same manner as described above.
Figure 62:
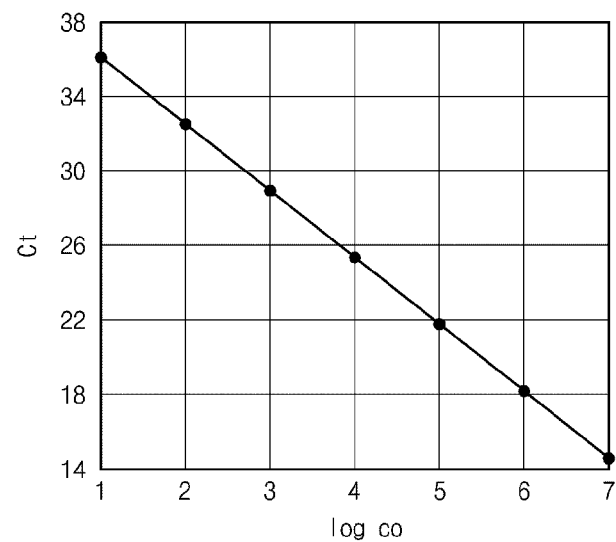
Figure 63:
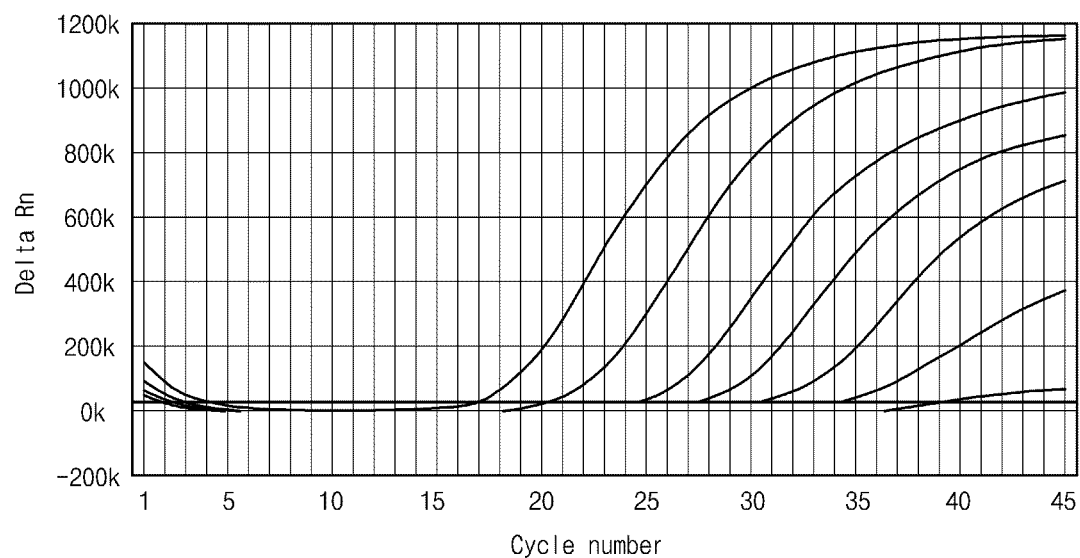
FIG. 63 presents amplification curves and a standard line illustrating the result of real-time PCR with the dried premix containing the same composition of PPi and PPase and also containing a target specific primer set and probe as well performed in the same manner as described above.
Figure 63:
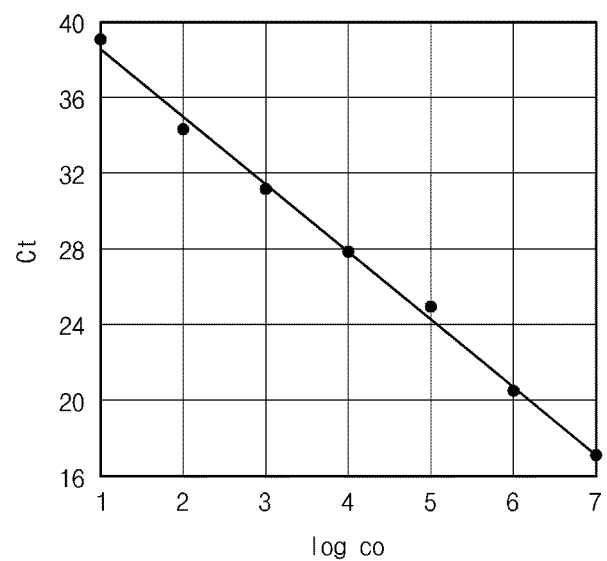

As a result, reactivity of the dried hot-start premix containing target specific primer set and probe was similar to that of the control dried hot-start premix prepared without the target specific primer and probe but containing PPi and PPase (FIGS. 62 and 63). The above results indicate that even if the hot-start premix is prepared by adding target specific primer set and probe during the drying process, PCR reactivity is not changed. Therefore, it shows the possibility of application in the production of a diagnostic kit for diverse diseases by containing a target specific primer set and probe in the premix.

SEQUENCE LISTING

Sequence listing is attached herewith.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

What is claimed is:

1. A dried composition in a reaction tube for hot-start PCR comprising reaction buffer, $MgCl_2$, 4 types of dNTPs, DNA polymerase, pyrophosphate, pyrophosphatase which converts inorganic pyrophosphate to two phosphate ions, and one or more stabilizer selected from the group consisting of polyol, gelatin, bovine serum albumin (BSA), Thesit, and PET-8000.

2. The dried composition in a reaction tube for hot-start PCR according to claim 1, wherein the composition further comprises a primer set or a probe.

3. The dried composition in a reaction tube for hot-start PCR according to claim 1, wherein the composition further comprises a fluorescent dye binding to DNA.

4. The dried composition in a reaction tube for hot-start PCR according to claim 3, wherein the fluorescent dye is selected from the group consisting of SyBr Green, EtBr and HRdye.

5. The dried composition in a reaction tube for hot-start PCR according to claim 1, wherein the composition further comprises template nucleic acid.

6. The dried composition in a reaction tube for hot-start PCR according to claim 1, wherein the pyrophosphate is included at the concentration of 0.3-5 mM in the final reaction solution and the pyrophosphatase is included at the concentration more than 30 to 200 mU in 20 µl d of the final reaction solution.

7. The dried composition in a reaction tube for hot-start PCR according to claim 6, wherein the pyrophosphate is included at the concentration of 0.95-3.0 mM in the final reaction solution.

8. The dried composition in a reaction tube for hot-start PCR according to claim 6, wherein the pyrophosphatase is included at the concentration of 50-100 mU in 20 µl of the final reaction solution.

9. The dried composition in a reaction tube for hot-start PCR according to claim 1, wherein the DNA polymerase is one or more polymerases selected from the group consisting of the polymerase having the activity of 5'→3' exonuclease, the polymerase having the activity of 3'→5' exonuclease, and the polymerase having none of the activities of 5'→3' exonuclease and 3'→5' exonuclease.

10. The dried composition in a reaction tube for hot-start PCR according to claim 1, wherein the composition further comprises a dye which is not reactive to nucleic acid.

11. The dried composition in a reaction tube for hot-start PCR according to claim 10, wherein the dye is one or more materials selected from the group consisting of rhodamine, tamra, lax, bromophenol blue, xylene cyanole, bromocresol red, and cresol red.

12. The dried composition in a reaction tube for hot-start PCR according to claim 1, wherein the composition is used for multiplex PCR, real time PCR or real-time quantitative PCR.

13. A kit for hot-start PCR comprising one of the dried compositions for hot-start PCR of claim 1.

14. A method for amplifying nucleic acid using one of the dried compositions for hot-start PCR of claim 1.

15. The method for amplifying nucleic acid according to claim 14, wherein the method comprises the following steps: mixing a sample containing template nucleic acid with the dried composition for hot-start PCR; performing a reaction to amplify the reaction mixture; and analyzing the amplified product of the template nucleic acid.

16. The method for amplifying nucleic acid according to claim 14, wherein the PCR is selected from the group consisting of multiplex PCR, real-time PCR and real-time quantitative PCR.

\* \* \* \* \*